US011821046B2

(12) United States Patent
Gao et al.

(10) Patent No.: US 11,821,046 B2
(45) Date of Patent: Nov. 21, 2023

(54) COMPOSITIONS AND METHODS FOR DETECTING ZIKA VIRUS NUCLEIC ACID

(71) Applicant: GEN-PROBE INCORPORATED, San Diego, CA (US)

(72) Inventors: Kui Gao, San Diego, CA (US); Jeffrey M. Linnen, Poway, CA (US)

(73) Assignee: Gen-Probe Incorporated, San Diego, CA (US)

( * ) Notice: Subject to any disclaimer, the term of this patent is extended or adjusted under 35 U.S.C. 154(b) by 545 days.

(21) Appl. No.: 17/032,310

(22) Filed: Sep. 25, 2020

(65) Prior Publication Data

US 2021/0010093 A1 Jan. 14, 2021

Related U.S. Application Data

(60) Division of application No. 16/659,375, filed on Oct. 21, 2019, now Pat. No. 11,332,798, which is a continuation of application No. 15/618,834, filed on Jun. 9, 2017, now Pat. No. 10,508,312.

(60) Provisional application No. 62/348,563, filed on Jun. 10, 2016.

(51) Int. Cl.
*C12Q 1/70* (2006.01)

(52) U.S. Cl.
CPC ....... *C12Q 1/701* (2013.01); *C12Q 2600/158* (2013.01); *C12Q 2600/16* (2013.01)

(58) Field of Classification Search
CPC ..................................................... C12Q 1/701
See application file for complete search history.

(56) References Cited

U.S. PATENT DOCUMENTS

| | | | | |
|---|---|---|---|---|
| 10,508,312 | B2 * | 12/2019 | Gao | C12Q 1/701 |
| 11,332,798 | B2 * | 5/2022 | Gao | C12Q 1/701 |
| 2003/0050470 | A1 * | 3/2003 | An | C07H 21/00 |
| | | | | 435/6.14 |
| 2004/0023207 | A1 * | 2/2004 | Polansky | A61K 48/005 |
| | | | | 435/456 |
| 2006/0263806 | A1 * | 11/2006 | Ma | G01N 33/57496 |
| | | | | 435/6.14 |
| 2011/0081646 | A1 * | 4/2011 | Carrick | C12Q 1/701 |
| | | | | 435/5 |
| 2018/0135140 | A1 * | 5/2018 | Gao | C12Q 1/701 |
| 2020/0040411 | A1 * | 2/2020 | Gao | C12Q 1/701 |
| 2021/0010093 | A1 * | 1/2021 | Gao | C12Q 1/701 |

FOREIGN PATENT DOCUMENTS

| | | | | |
|---|---|---|---|---|
| WO | WO-9612040 | A2 * | 4/1996 | C12Q 1/689 |
| WO | WO-9622392 | A2 * | 7/1996 | C12Q 1/689 |
| WO | WO-2017214511 | A2 * | 12/2017 | C12Q 1/701 |
| WO | 2018005357 | A1 | 1/2018 | |

OTHER PUBLICATIONS

Faye et al., 2013. Quantitative real-time PCR detection of Zika virus and evaluation with field-caught mosquitoes. Virology journal, 10, pp. 1-8. (Year: 2013).*
Gadberry et al., 2005. Primaclade—a flexible tool to find conserved PCR primers across multiple species. Bioinformatics, 21(7), pp. 1263-1264. (Year: 2005).*
Genbank Accession No. AY632535 Zika virus strain MR 766, complete genome (submitted Aug. 1, 2006, retrieved on Mar. 11, 2023 from http://www.ncbi.nlm.nih.gov/nuccore/AY632535). (Year: 2006).*
Genbank Accession No. EU545988 Zika virus polyprotein gene, complete cds (submitted Mar. 5, 2008, retrieved on Mar. 11, 2023 from http://www.ncbi.nlm.nih.gov/nuccore/EU545988). (Year: 2008).*
Genbank Accession No. NC_012532 Zika virus, complete genome (submitted May 21, 2004, retrieved on Mar. 11, 2023 from http://www.ncbi.nlm.nih.gov/nuccore/NC_012532). (Year: 2004).*
SantaLucia Jr, John. Physical principles and visual-OMP software for optimal PCR design. PCR Primer Design. Humana Press, 2007: pp. 3-33. (Year: 2007).*
Sarrazin et al., 2000. Detection of residual hepatitis C virus RNA by transcription-mediated amplification in patients with complete virologic response according to polymerase chain reaction-based assays. Hepatology, 32(4), pp. 818-823. (Year: 2000).*
Tappe et al. 2014. First case of laboratory-confirmed Zika virus infection imported into Europe, Nov. 2013. Eurosurveillance, 19(4), 20685, pp. 1-4. (Year: 2014).*
PCT Communication Relating to the Results of the Partial International Search, International Application No. PCT/US2017/036764, dated Oct. 19, 2017.
Balm et al., "A Diagnostic Polymerase Chain Reaction Assay for Zika Virus," Journal of Medical Virology, 2012, vol. 84, No. 9, pp. 1501-1505.
Faye et al., "Quantitative real-time PCR detection of Zika virus and evaluation with field-caught Mosquitoes," Virology Journal, 2013, vol. 10, No. 1, pp. 2-8.
Lanciotti et al., "Genetic and Serologic Properties of Zika Virus Associated with an Epidemic, Yap State, Micronesia, 2007," Emerging Infectious Diseases, 2008, vol. 14, No. 8, pp. 1232-1239.
Pessoa et al., "Investigation into an Outbreak of Dengue-like Illness in Pernambuco, Brazil, Revealed a Cocirculation of Zika, Chikungunya, and Dengue Virus Type 1," Medicine, 2016, vol. 95, No. 12, pp. e3201.
Pyke et al., "Imported Zika Virus Infection from the Cook Islands into Australia, 2014," PLoS Currents, 2014.
PCT International Search Report & Written Opinion, International Application No. PCT/US2017/036764, dated Dec. 13, 2017.
PCT International Preliminary Report on Patentability & Written Opinion, International Application No. PCT/US2017/036764, dated Dec. 11, 2018.
CIPO Examiner's Requisition, Canadian Application No. 3,026,723, dated Oct. 1, 2019.

* cited by examiner

*Primary Examiner* — Teresa E Strzelecka
*Assistant Examiner* — Olayinka A Oyeyemi
(74) *Attorney, Agent, or Firm* — Christensen O'Connor Johnson Kindness PLLC; Jeffrey E. Landes

(57) ABSTRACT

Disclosed are nucleic acid oligomers, including amplification oligomers, capture probes, and detection probes, for detection of Zika virus nucleic acid. Also disclosed are methods of specific nucleic acid amplification and detection using the disclosed oligomers, as well as corresponding reaction mixtures and kits.

20 Claims, No Drawings

Specification includes a Sequence Listing.

COMPOSITIONS AND METHODS FOR DETECTING ZIKA VIRUS NUCLEIC ACID

CROSS-REFERENCE TO RELATED APPLICATIONS

This application is a divisional of U.S. patent application Ser. No. 16/659,375, filed Oct. 21, 2019, now issued as U.S. Pat. No. 11,332,798, which is a continuation of U.S. patent application Ser. No. 15/618,834, filed Jun. 9, 2017, now issued as U.S. Pat. No. 10,508,312, which claims benefit of priority under 35 U.S.C § 119(e) to U.S. Provisional Application No. 62/348,563, filed Jun. 10, 2016, each of which is incorporated herein by reference.

REFERENCE TO SEQUENCE LISTING

The instant application contains a Sequence Listing which has been submitted in ASCII format via EFS-Web and is hereby incorporated by reference in its entirety. Said ASCII Copy, created on Sep. 25, 2020, is named "DIA-0025-05-DV1_SeqList_ST25.txt" and is 57,994 bytes in size.

BACKGROUND

Zika virus is a mosquito-borne Flavivirus that has been associated with human disease ranging from subclinical to mild illnesses. Clinical characteristics of Zika virus infection include fever, headache, malaise, stomach ache, dizziness, anorexia, and maculopapular rash. Zika virus infection has also been associated with serious and sometimes fatal cases of Guillain-Barré syndrome. Additionally, there is mounting evidence indicating that Zika virus infection can cause microcephaly and other birth defects in infants born to infected mothers. Although the primary route of infection is through the bite of a mosquito, sexual transmission and possible transfusion transmission of Zika virus have been reported.

SUMMARY

Disclosed herein is a combination of at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence. In some aspects of the combination of at least two amplification oligomers, the first amplification oligomer is contained within SEQ ID NO:24 and contains SEQ ID NO:25. In some aspects, the first amplification oligomer comprises a sequence that is selected from the group consisting of: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:49, SEQ ID NO:50, SEQ ID NO:51, SEQ ID NO:52, and SEQ ID NO:53. In some aspects, the target hybridizing region of the second amplification oligomer is contained within SEQ ID NO:150. In some aspects, the target hybridizing region of the second amplification oligomer is 19 contiguous nucleobases in length or is 20 contiguous nucleobases in length. In some aspects, the target hybridizing sequence of the second amplification oligomer is selected from the group consisting of: SEQ ID NO:112, SEQ ID NO:113, SEQ ID NO:114, SEQ ID NO:119, SEQ ID NO:121, SEQ ID NO:125, SEQ ID NO:126, SEQ ID NO:127, SEQ ID NO:128, SEQ ID NO:129, SEQ ID NO:130, SEQ ID NO:131, and SEQ ID NO:134. In some aspects, the second amplification oligomer is joined at its 5' end to a promoter sequence that is a T7 promoter sequence. In some aspects, the T7 promoter sequence consists of SEQ ID NO:179. In some aspects, the second amplification oligomer comprises a sequences selected from the group consisting of: SEQ ID NOs:74 to 89, SEQ ID NO:107, and SEQ ID NO:108.

In some aspects of the combination of at least two amplification oligomers, the combination of first amplification oligomer and second amplification oligomer comprise nucleic acid sequences selected from one of the following groups (i) SEQ ID NO:16 and SEQ ID NO:78; (ii) SEQ I DNO:16 and SEQ ID NO:80; (iii) SEQ ID NO:16 and SEQ ID NO:75; (iv) SEQ ID NO:16 and SEQ ID NO:89; (v) SEQ ID NO:16 and SEQ ID NO:74; (vi) SEQ ID NO:11 and SEQ ID NO:78; (vii) SEQ ID NO:11 and SEQ ID NO:80; (viii) SEQ ID NO:11 and SEQ ID NO:75; (ix) SEQ ID NO:11 and SEQ ID NO:89; (x) SEQ ID NO:11 and SEQ ID NO:74; (xi) SEQ ID NO:12 and SEQ ID NO:79; (xii) SEQ ID NO:12 and SEQ ID NO:87; (xiii) SEQ ID NO:12 and SEQ ID NO:89; (xiv) SEQ ID NO:12 and SEQ ID NO:74; (xv) SEQ ID NO:17 and SEQ ID NO:79; (xvi) SEQ ID NO:17 and SEQ ID NO:87; (xvii) SEQ ID NO:17 and SEQ ID NO:89; (xviii) SEQ ID NO:17 and SEQ ID NO:74; (xix) SEQ ID NO:53 and SEQ ID NO:78; (xx) SEQ I DNO:53 and SEQ ID NO:80; (xxi) SEQ ID NO:53 and SEQ ID NO:75; (xxii) SEQ ID NO:53 and SEQ ID NO:89; (xxiii) SEQ ID NO:53 and SEQ ID NO:74; (xxiv) SEQ ID NO:18 and SEQ ID NO:78; (xxv) SEQ I DNO:18 and SEQ ID NO:80; (xxvi) SEQ ID NO:18 and SEQ ID NO:75; (xxvii) SEQ ID NO:18 and SEQ ID NO:89; or (xxviii) SEQ ID NO:18 and SEQ ID NO:74.

In some aspects of the combination of at least two amplification oligomers, the combination comprises a third amplification oligomer for amplifying a target sequence of a Zika virus nucleic acid, wherein the third amplification oligomer comprises a target hybridizing sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:49, SEQ ID NO:50, SEQ ID NO:51, SEQ ID NO:52, and SEQ ID NO:53, and wherein the target hybridizing sequence of the first amplification oligomer and the target hybridizing sequence of the third amplification oligomer are different sequences. In some aspects, the combination of first amplification oligomer, second amplification oligomer and third amplification oligomer is one of: (i) a first amplification oligomer comprising a nucleic acid sequence consisting of SEQ ID NO:16; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:11, 12, 17, 18, & 53; (ii) a first amplification oligomer comprising a nucleic acid sequence consisting of SEQ ID NO:11; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:12, 17, 18, & 53; (iii) a first amplification oligomer comprising a nucleic acid sequence consisting of SEQ ID NO:12; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:17, 18, & 53; (iv) a first amplification oligomer comprising a nucleic acid sequence consisting of SEQ ID NO:17; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:18, & 53; or (v) a first amplification oligomer comprising a nucleic acid sequence consisting of SEQ ID NO:18; a second amplification oligomer comprising a nucleic acid sequence selected from the group consisting of SEQ ID NOs:74, 75, 78, 80, & 89; and a third amplification oligomer comprising a nucleic acid sequence consisting of SEQ ID NO:53. In some aspects of the combination of at least two amplification oligomers, the combination comprises a fourth amplification oligomer for amplifying a target sequence of a Zika nucleic acid, wherein the fourth amplification oligomer comprises a target hybridizing sequence selected from the group consisting of: SEQ ID NO113, SEQ ID NO:114, SEQ ID NO:115, SEQ ID NO:125, SEQ ID NO:127, SEQ ID NO:128, & SEQ ID NO:134, and wherein the target hybridizing sequence of the fourth amplification oligomer is optionally joined at its 5' end to a promoter sequence, and wherein the target hybridizing sequence of the second amplification oligomer and the target hybridizing sequence of the fourth amplification oligomer are different sequences. In some aspects, the target hybridizing sequence of the fourth amplification oligomer is joined to a promoter sequence is a T7 promoter sequence. In some aspects, the promoter sequence consists of SEQ ID NO:179. In some aspects, the fourth amplification oligomer comprises a sequence that is selected from the group consisting of: SEQ ID NO:74, SEQ ID NO:75, SEQ ID NO:78, SEQ ID NO:79, SEQ ID NO:80, SEQ ID NO:87, and SEQ ID NO:89.

Further disclosed herein is a combination of at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence.

In some aspects of the combination of at least two amplification oligomers, the target hybridizing sequence of the first amplification oligomer is contained within SEQ ID NO:4. In some aspects, the target hybridizing sequence of the first amplification oligomer contains SEQ ID NO:2. In some aspects, the first amplification oligomer comprises a sequence selected from the group consisting of: SEQ ID NO:2, SEQ ID NO:3, SEQ ID NO:4, SEQ ID NO:5, SEQ ID NO:28, SEQ ID NO:29, SEQ ID NO:30, SEQ ID NO:31, SEQ ID NO:32, SEQ ID NO:33, SEQ ID NO:34, and SEQ ID NO:35. In some aspects, the target hybridizing sequence of the second amplification oligomer is contained within SEQ ID NO:152. In some aspects, the target hybridizing sequence of the second amplification oligomer contains SEQ ID NO:148. In some aspects, the target hybridizing sequence of the second amplification oligomer contains SEQ ID NO:149. In some aspects, the second amplification oligomer is joined at its 5' end to a promoter sequence that is a T7 promoter sequence. In some aspects, the T7 promoter sequence consists of SEQ ID NO:179. In some aspects, the target hybridizing sequence of the second amplification oligomer is selected from the group consisting of: SEQ ID NO:111, SEQ ID NO:116, SEQ ID NO:117, SEQ ID NO:122, SEQ ID NO:135, SEQ ID NO:136, SEQ ID NO:137, and SEQ ID NO:138. In some aspects, the second amplification oligomer comprises a sequence selected from the group consisting of: SEQ ID NO:90, SEQ ID NO:91, SEQ ID NO:92, SEQ ID NO:93, SEQ ID NO:94, SEQ ID NO:95, SEQ ID NO:96, and SEQ ID NO:97.

In some aspects of the combination of at least two amplification oligomers, the combination of first amplification oligomer and second amplification oligomer comprise nucleic acid sequences selected from one of the following groups: (i) SEQ ID NO:30 and SEQ ID NO:92; (ii) SEQ ID NO:30 and SEQ ID NO:94; (iii) SEQ ID NO:30 and SEQ ID NO:95 (iv) SEQ ID NO:35 and SEQ ID NO:92; (v) SEQ ID NO:35 and SEQ ID NO:94; and vi) SEQ ID NO:35 and SEQ ID NO:95. In some aspects, the combination further comprises a third amplification oligomer for amplifying a target sequence of a Zika virus nucleic acid, wherein the third amplification oligomer comprises a target hybridizing sequence selected from the group consisting of: SEQ ID NO:111, SEQ ID NO:116, SEQ ID NO:117, SEQ ID NO:122, SEQ ID NO:135, SEQ ID NO:136, SEQ ID NO:137, & SEQ ID NO:138, wherein, optionally, the target hybridizing sequence of the third amplification oligomer is joined at it 5' end to a promoter sequence, and wherein the target hybridizing sequence of the second amplification oligomer and the target hybridizing sequence of the third amplification oligomer are different sequences. In some aspects, the target hybridizing sequence of the third amplification oligomer is joined at its 5' end to a promoter sequence that is a T7 promoter sequence. In some aspects, the promoter sequence consists of SEQ ID NO:179. In some aspects, the third amplification oligomer comprises a sequence selected from the group consisting of: SEQ ID NO:90, SEQ ID NO:91, SEQ ID NO:92, SEQ ID NO:93, SEQ ID NO:94, SEQ ID NO:95, SEQ ID NO:96, and SEQ ID NO:97.

Further disclosed herein is a combination of at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence.

In some aspects of the combination of at least two amplification oligomers, the target hybridizing sequence of the first amplification oligomer is contained within SEQ ID NO:6. In some aspects, the target hybridizing sequence of the first amplification oligomer contains SEQ ID NO:7. In some aspects, the target hybridizing sequence of the first amplification oligomer contains SEQ ID NO:8. In some aspects, the first amplification oligomer comprises a target hybridizing sequence that is selected from the group consisting of: SEQ ID NOs:36 to 48. In some aspects, the target hybridizing sequence of the second amplification oligomer is selected from the group consisting of: SEQ ID NO:123, SEQ ID NO:124, SEQ ID NO:139, SEQ ID NO:140, SEQ ID NO:141, SEQ ID NO:142, SEQ ID NO:143, SEQ ID NO:144, SEQ ID NO:145, SEQ ID NO:146, & SEQ ID NO:147. In some aspects, the second amplification oligomer is joined at its 5' end to a promoter sequence that is a T7 promoter sequence. In some aspects, the T7 promoter sequence consists of SEQ ID NO:179. In some aspects, the second amplification oligomer comprises a sequence selected from the group consisting of: SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:109, and SEQ ID NO:110.

In some aspects of the combination of at least two amplification oligomers, the combination of first amplification oligomer and second amplification oligomer comprise nucleic acid sequences selected from one of the following groups: (i) SEQ ID NO:36 and SEQ ID NO:103; (ii) SEQ ID NO:36 and SEQ ID NO:104; (iii) SEQ ID NO:36 and SEQ ID NO:105; (iv) SEQ ID NO:37 and SEQ ID NO:102; (v) SEQ ID NO:37 and SEQ ID NO:103; (vi) SEQ ID NO:37 and SEQ ID NO:105; (vii) SEQ ID NO:38 and SEQ ID NO:105; (viii) SEQ ID NO:39 and SEQ ID NO:104; (ix) SEQ ID NO:39 and SEQ ID NO:105; (x) SEQ ID NO:39 and SEQ ID NO:106; (xi) SEQ ID NO:41 and SEQ ID NO:104; (xii) SEQ ID NO:41 and SEQ ID NO:106; (xiii) SEQ ID NO:43 and SEQ ID NO:106; (xiv) SEQ ID NO:45 and SEQ ID NO:103; (xv) SEQ ID NO:45 and SEQ ID NO:105; (xvi) SEQ ID NO:45 and SEQ ID NO:106; (xvii) SEQ ID NO:46 and SEQ ID NO:106; (xviii) SEQ ID NO:47 and SEQ ID NO:104; and (xix) SEQ ID NO:47 and SEQ ID NO:106.

Further disclosed herein is a detection probe oligomer for the detection of a Zika virus nucleic acid, wherein the detection probe oligomer comprises: (i) a target hybridizing sequence configured to hybridize under stringent conditions to a target sequence of a Zika virus nucleic acid, and, optionally, one or more nucleobases that are not complementary to the Zika virus target nucleic acid, and (ii) a detectable label, wherein the Zika virus target nucleic acid sequence is selected from the group consisting of: SEQ ID NO:187, SEQ ID NO:188, & SEQ ID NO:189, including a complement thereof, and/or an RNA equivalent thereof. In some aspects, the detection probe oligomer comprises a target hybridizing sequence that is configured to selectively hybridize a sequence selected from the group consisting of: SEQ ID NO:194, SEQ ID NO:195, SEQ ID NO:196, SEQ ID NO:197, & SEQ ID NO:198, including a complement thereof, and/or an RNA equivalent thereof. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NOs:54 to 63 and 66 to 73. In some aspects, the target hybridizing sequence of the detection probe oligomer comprises the one or more nucleobases that are not complementary to the target nucleic acid. In some aspects, the target hybridizing sequence of the detection probe oligomer comprises from 3 to 7 contiguous nucleobases that are not complementary to the target nucleic acid and that are joined to one of the 3' end or the 5' end of the target hybridizing sequence. In some aspects, the 3 to 7 contiguous nucleobases that are not complementary to the target nucleic acid, are complementary to a portion of the target hybridizing sequence of the detection probe oligomer. In some aspects, the detection probe oligomer comprises a detectable label that is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and the detection probe oligomer further comprises a quenching compound. In some aspects, the detection probe oligomer is selected from the group consisting of TaqMan detection probes, molecular beacons, and molecular torches. In some aspects, the target hybridizing sequence of the detection probe oligomer does not comprise the one or more nucleobases that are not complementary to the target nucleic acid.

Further disclosed herein is an amplification reaction mixture comprising a buffered aqueous solution comprising any of the above described combinations of at least two amplification oligomers. Further disclosed herein is an amplification reaction mixture, comprising a dried composition comprising any of the above described combinations of at least two amplification oligomers. In some aspects, the dried composition comprises a bulking agent. In some aspects, the dried composition comprises less than 5% (w/w) of a bulking agent. In some aspects, the bulking agent is a disaccharide form of an amorphous sugar. In some aspects, the bulking agent is one or more of mannitol, trehalose sucrose, lactose, sorbitol, raffinose, and glucose. In some aspects, the dried composition further comprises at least one polymerase enzyme.

Further disclosed herein is a multiplex amplification reaction mixture, wherein the mixture is a buffered aqueous solution comprising at least two combinations of at least two amplification oligomers selected from the group consisting of: (A) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence; (B) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; (C) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; and (D) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence.

Further disclosed herein is a multiplex amplification reaction mixture, wherein the mixture is a dried composition comprising at least two combinations of at least two amplification oligomers selected from the group consisting of: (A) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence; (B) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; (C) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; and (D) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence, and combined with at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence. In some aspects, the dried composition comprises a bulking agent. In some aspects, the dried composition comprises less than 5% (w/w) of a bulking agent. In some aspects, the bulking agent is a disaccharide form of an amorphous sugar. In some aspects, the bulking agent is one or more of mannitol, trehalose sucrose, lactose, sorbitol, raffinose, and glucose. In some aspects, the dried composition further comprises at least one polymerase enzyme.

Further disclosed herein is a kit comprising any of the at least two amplification oligomers described herein. In some aspects, the first amplification oligomer is in a first container within the kit and the second amplification oligomer is in a second container within the kit. In one aspect, the kit further comprises a detection probe oligomer. In one aspect, the detection probe oligomer is any detection probe oligomer described herein.

Further disclosed herein is a detection reaction mixture comprising a buffered aqueous solution and a detection probe oligomer for the detection of a Zika virus nucleic acid, wherein the detection probe oligomer comprises: (i) a target hybridizing sequence configured to hybridize under stringent conditions to a target sequence of a Zika virus nucleic acid, and, optionally, one or more nucleobases that are not complementary to the Zika virus target nucleic acid, and (ii) a detectable label, wherein the Zika virus target nucleic acid sequence is selected from the group consisting of: SEQ ID NO:187, SEQ ID NO:188, & SEQ ID NO:189, including a complement thereof, and/or an RNA equivalent thereof. In some aspects, the detection probe oligomer comprises a target hybridizing sequence that is configured to selectively hybridize a sequence selected from the group consisting of: SEQ ID NO:194, SEQ ID NO:195, SEQ ID NO:196, SEQ ID NO:197, & SEQ ID NO:198, including a complement thereof, and/or an RNA equivalent thereof. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NOs:54 to 63 and 66 to 73. In some aspects, the target hybridizing sequence of the detection probe oligomer comprises the one or more nucleobases that are not complementary to the target nucleic acid. In some aspects, the target hybridizing sequence of the detection probe oligomer comprises from 3 to 7 contiguous nucleobases that are not complementary to the target nucleic acid and that are joined to one of the 3' end or the 5' end of the target hybridizing sequence. In some aspects, the 3 to 7 contiguous nucleobases that are not complementary to the target nucleic acid, are complementary to a portion of the target hybridizing sequence of the detection probe oligomer. In some aspects, the detection probe oligomer comprises a detectable label that is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and the detection probe oligomer further comprises a quenching compound. In some aspects, the detection probe oligomer is selected from the group consisting of TaqMan detection probes, molecular beacons, and molecular torches. In some aspects, the target hybridizing sequence of the detection probe oligomer does not comprise the one or more nucleobases that are not complementary to the target nucleic acid.

Further disclosed herein is a dried composition comprising a detection probe oligomer for the detection of a Zika virus nucleic acid, wherein the detection probe oligomer comprises: (i) a target hybridizing sequence configured to hybridize under stringent conditions to a target sequence of a Zika virus nucleic acid, and, optionally, one or more nucleobases that are not complementary to the Zika virus target nucleic acid, and (ii) a detectable label, wherein the Zika virus target nucleic acid sequence is selected from the group consisting of: SEQ ID NO:187, SEQ ID NO:188, & SEQ ID NO:189, including a complement thereof, and/or an RNA equivalent thereof. In some aspects, the detection probe oligomer comprises a target hybridizing sequence that is configured to selectively hybridize a sequence selected from the group consisting of: SEQ ID NO:194, SEQ ID NO:195, SEQ ID NO:196, SEQ ID NO:197, & SEQ ID NO:198, including a complement thereof, and/or an RNA equivalent thereof. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NOs:54 to 63 and 66 to 73. In some aspects, the target hybridizing sequence of the detection probe oligomer comprises the one or more nucleobases that are not complementary to the target nucleic acid. In some aspects, the target hybridizing sequence of the detection probe oligomer comprises from 3 to 7 contiguous nucleobases that are not complementary to the target nucleic acid and that are joined to one of the 3' end or the 5' end of the target hybridizing sequence. In some aspects, the 3 to 7 contiguous nucleobases that are not complementary to the target nucleic acid, are complementary to a portion of the target hybridizing sequence of the detection probe oligomer. In some aspects, the detection probe oligomer comprises a detectable label that is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and the detection probe oligomer further comprises a quenching compound. In some aspects, the detection probe oligomer is selected from the group consisting of TaqMan detection probes, molecular beacons, and molecular torches. In some aspects, the target hybridizing sequence of the detection probe oligomer does not comprise the one or more nucleobases that are not complementary to the target nucleic acid. In some aspects, the dried composition comprises a bulking agent. In some aspects, the dried composition comprises less than 5% (w/w) of a bulking agent. In some aspects, the bulking agent is a disaccharide form of an amorphous sugar. In some aspects, the bulking agent is one or more of mannitol, trehalose sucrose, lactose, sorbitol, raffinose, and glucose. In some aspects, the dried composition further comprises at least one polymerase enzyme. In some aspects, the dried composition further comprises one or more of the combinations of at least two amplification oligomers described herein.

Further disclosed herein are methods for determining the presence or absence of a Zika virus nucleic acid in a sample, the method comprising the steps of: (A) contacting a sample with a combination of at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence; (B) performing an in vitro nucleic acid amplification reaction, wherein any Zika virus target sequence present in the sample is used as a template for generating an amplification product; and (C) detecting the presence or absence of the amplification product, thereby determining the presence or absence of the Zika virus nucleic acid in the sample. In some aspects, the target hybridizing sequence of the first amplification oligomer is contained within SEQ ID NO:24 and contains SEQ ID NO:25. In some aspects, the first amplification oligomer comprises a sequence that is selected from the group consisting of: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:49, SEQ ID NO:50, SEQ ID NO:51, SEQ ID NO:52, and SEQ ID NO:53. In some aspects, the target hybridizing region of the second amplification oligomer is contained within SEQ ID NO:150. In some aspects, the target hybridizing region of the second amplification oligomer is 19 contiguous nucleobases in length or is 20 contiguous nucleobases in length. In some aspects, the target hybridizing sequence of the second amplification oligomer is selected from the group consisting of: SEQ ID NO:113, SEQ ID NO:119, SEQ ID NO:125, SEQ ID NO:126, SEQ ID NO:127, SEQ ID NO:130, and SEQ ID NO:131. In some aspects, the target hybridizing sequence of the second amplification oligomer is selected from the group consisting of: SEQ ID NO:112, SEQ ID NO:113, SEQ ID NO:114, SEQ ID NO:119, SEQ ID NO:121, SEQ ID NO:125, SEQ ID NO:126, SEQ ID NO:127, SEQ ID NO:128, SEQ ID NO:129, SEQ ID NO:130, SEQ ID NO:131, and SEQ ID NO:134. In some aspects, the second amplification oligomer is joined at its 5' end to a promoter sequence that is a T7 promoter sequence. In some aspects, the T7 promoter sequence consists of SEQ ID NO:179. In some aspects, the second amplification oligomer comprises a sequences selected from the group consisting of: SEQ ID NOs:74 to 89, SEQ ID NO:107, and SEQ ID NO:108. In some aspects, the combination of first amplification oligomer and second amplification oligomer comprise nucleic acid sequences selected from the group consisting of: (i) SEQ ID NO:16 and SEQ ID NO:78; (ii) SEQ I DNO:16 and SEQ ID NO:80; (iii) SEQ ID NO:16 and SEQ ID NO:75; (iv) SEQ ID NO:16 and SEQ ID NO:89; (v) SEQ ID NO:16 and SEQ ID NO:74; (vi) SEQ ID NO:11 and SEQ ID NO:78; (vii) SEQ ID NO:11 and SEQ ID NO:80; (viii) SEQ ID NO:11 and SEQ ID NO:75; (ix) SEQ ID NO:11 and SEQ ID NO:89; (x) SEQ ID NO:11 and SEQ ID NO:74; (xi) SEQ ID NO:12 and SEQ ID NO:79; (xii) SEQ ID NO:12 and SEQ ID NO:87; (xiii) SEQ ID NO:12 and SEQ ID NO:89; (xiv) SEQ ID NO:12 and SEQ ID NO:74; (xv) SEQ ID NO:17 and SEQ ID NO:79; (xvi) SEQ ID NO:17 and SEQ ID NO:87; (xvii) SEQ ID NO:17 and SEQ ID NO:89; (xviii) SEQ ID NO:17 and SEQ ID NO:74; (xix) SEQ ID NO:53 and SEQ ID NO:78; (xx) SEQ I DNO:53 and SEQ ID NO:80; (xxi) SEQ ID NO:53 and SEQ ID NO:75; (xxii) SEQ ID NO:53 and SEQ ID NO:89; (xxiii) SEQ ID NO:53 and SEQ ID NO:74; (xxiv) SEQ ID NO:18 and SEQ ID NO:78; (xxv) SEQ I DNO:18 and SEQ ID NO:80; (xxvi) SEQ ID NO:18 and SEQ ID NO:75; (xxvii) SEQ ID NO:18 and SEQ ID NO:89; and (xxviii) SEQ ID NO:18 and SEQ ID NO:74. In one aspect, the combination of at least two amplification oligomers comprises a third amplification oligomer for amplifying a target sequence of a Zika virus nucleic acid, wherein the third amplification oligomer comprises a target hybridizing sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:49, SEQ ID NO:50, SEQ ID NO:51, SEQ ID NO:52, and SEQ ID NO:53, and wherein the target hybridizing sequence of the first amplification oligomer and the target hybridizing sequence of the third amplification oligomer are different sequences. In one aspect, the combination of first amplification oligomer, second amplification oligomer and third amplification oligomer is: (i) a first amplification oligomer comprising a nucleic acid sequence consisting of SEQ ID NO:16; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:11, 12, 17, 18, & 53; (ii) a first amplification oligomer comprising a nucleic acid sequence consisting of SEQ ID NO:11; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:12, 17, 18, & 53; (iii) a first amplification oligomer comprising a nucleic acid sequence consisting of SEQ ID NO:12; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:17, 18, & 53; (iv) a first amplification oligomer comprising a nucleic acid sequence consisting of SEQ ID NO:17; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:18, & 53; or (v) a first amplification oligomer comprising a nucleic acid sequence consisting of SEQ ID NO:18; a second amplification oligomer comprising a nucleic acid sequence selected from the group consisting of SEQ ID NOs:74, 75, 78, 80, & 89; and a third amplification oligomer comprising a nucleic acid sequence consisting of SEQ ID NO:53. In some aspects, the combination of at least two amplification oligomers comprises a fourth amplification oligomer for amplifying a target sequence of a Zika nucleic acid, wherein the fourth amplification oligomer comprises a target hybridizing sequence selected from the group consisting of: SEQ ID NO113, SEQ ID NO:114, SEQ ID NO:115, SEQ ID NO:125, SEQ ID NO:127, SEQ ID NO:128, & SEQ ID NO:134, and wherein the target hybridizing sequence of the fourth amplification oligomer is optionally joined at its 5' end to a promoter sequence, and wherein the target hybridizing sequence of the second amplification oligomer and the target hybridizing sequence of the fourth amplification oligomer are different sequences. In some aspects, the target hybridizing sequence of the fourth amplification oligomer is joined to a promoter sequence is a T7 promoter sequence, wherein preferably the promoter sequence consists of SEQ ID NO:179. In some aspects, the fourth amplification oligomer comprises a sequence that is selected from the group consisting of: SEQ ID NO:74, SEQ ID NO:75, SEQ ID NO:78, SEQ ID NO:79, SEQ ID NO:80, SEQ ID NO:87, and SEQ ID NO:89. In some aspects, the detecting step comprises contacting the in vitro amplification reaction with at least one detection probe oligomer, wherein the detection probe oligomer comprises: (i) a target hybridizing sequence and, optionally, one or more nucleobases that are not complementary to the Zika virus target nucleic acid, and (ii) a detectable label. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NO:56, SEQ ID NO:57, and SEQ ID NOs:66 to 73. In some aspects, the target hybridizing sequence of the detection probe oligomer comprises the one or more nucleobases that are not complementary to the target nucleic acid. In some aspects, the target hybridizing sequence of the detection probe oligomer comprises at either its 3' end or its 5' end from 3 to 7 contiguous nucleobases that are not complementary to the target sequence of the Zika virus nucleic acid. In some aspects, the 3 to 7 contiguous nucleobases that are not complementary to the target sequence, are complementary to a portion of the target hybridizing sequence of the detection probe oligomer. In some aspects, the detectable label is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and wherein the detection probe oligomer further comprises a quenching compound. In some aspects, the detection probe oligomer is selected from the group consisting of TaqMan detection probes, molecular beacons, and molecular torches. In some aspects, the target hybridizing sequence does not comprise the one or more nucleobases that are not complementary to the target nucleic acid. In some aspects, the combination of the first amplification oligomer and the second amplification oligomer is selected from the group consisting of: (i) SEQ ID NO:16 and SEQ ID NO:78; (ii) SEQ I DNO:16 and SEQ ID NO:80; (iii) SEQ ID NO:16 and SEQ ID NO:75; (iv) SEQ ID NO:16 and SEQ ID NO:89; (v) SEQ ID NO:16 and SEQ ID NO:74; (vi) SEQ ID NO:11 and SEQ ID NO:78; (vii) SEQ ID NO:11 and SEQ ID NO:80; (viii) SEQ ID NO:11 and SEQ ID NO:75; (ix) SEQ ID NO:11 and SEQ ID NO:89; (x) SEQ ID NO:11 and SEQ ID NO:74; (xi) SEQ ID NO:12 and SEQ ID NO:79; (xii) SEQ ID NO:12 and SEQ ID NO:87; (xiii) SEQ ID NO:12 and SEQ ID NO:89; (xiv) SEQ ID NO:12 and SEQ ID NO:74; (xv) SEQ ID NO:17 and SEQ ID NO:79; (xvi) SEQ ID NO:17 and SEQ ID NO:87; (xvii) SEQ ID NO:17 and SEQ ID NO:89; (xviii) SEQ ID NO:17 and SEQ ID NO:74; (xix) SEQ ID NO:53 and SEQ ID NO:78; (xx) SEQ I DNO:53 and SEQ ID NO:80; (xxi) SEQ ID NO:53 and SEQ ID NO:75; (xxii) SEQ ID NO:53 and SEQ ID NO:89; (xxiii) SEQ ID NO:53 and SEQ ID NO:74; (xxiv) SEQ ID NO:18 and SEQ ID NO:78; (xxv) SEQ I DNO:18 and SEQ ID NO:80; (xxvi) SEQ ID NO:18 and SEQ ID NO:75; (xxvii) SEQ ID NO:18 and SEQ ID NO:89; and (xxviii) SEQ ID NO:18 and SEQ ID NO:74, and wherein the detection probe oligomer comprises a target hybridizing sequence consisting of SEQ ID NO:69, and the detectable label consists of an acridinium ester label. In some aspects, the combination comprises a third amplification oligomer for amplifying a target sequence of a Zika virus nucleic acid, wherein the third amplification oligomer comprises a target hybridizing sequence selected from the group consisting of: SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26, SEQ ID NO:27, SEQ ID NO:49, SEQ ID NO:50, SEQ ID NO:51, SEQ ID NO:52, and SEQ ID NO:53, and wherein the target hybridizing sequence of the first amplification oligomer and the target hybridizing sequence of the third amplification oligomer are different sequences. In some aspects, the combination of first amplification oligomer, second amplification oligomer and third amplification oligomer is: (i) a first amplification oligomer comprising a nucleic acid sequence consisting of SEQ ID NO:16; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:11, 12, 17, 18, & 53; (ii) a first amplification oligomer comprising a nucleic acid sequence consisting of SEQ ID NO:11; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:12, 17, 18, & 53; (iii) a first amplification oligomer comprising a nucleic acid sequence consisting of SEQ ID NO:12; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:17, 18, & 53; (iv) a first amplification oligomer comprising a nucleic acid sequence consisting of SEQ ID NO:17; a second amplification oligomer comprising a nucleic acid sequence selected from the group consisting of SEQ ID NOs:74, 75, 78, 80, & 89; and a third amplification oligomer comprising a nucleic acid sequence selected from the group consisting of SEQ ID NOs:18, & 53; or (v) a first amplification oligomer comprising a nucleic acid sequence consisting of SEQ ID NO:18; a second amplification oligomer comprising a nucleic acid sequence selected from the group consisting of SEQ ID NOs:74, 75, 78, 80, & 89; and a third amplification oligomer comprising a nucleic acid sequence consisting of SEQ ID NO:53. In some aspects, the combination comprises a fourth amplification oligomer for amplifying a target sequence of a Zika nucleic acid, wherein the fourth amplification oligomer comprises a target hybridizing sequence selected from the group consisting of: SEQ ID NO113, SEQ ID NO:114, SEQ ID NO:115, SEQ ID NO:125, SEQ ID NO:127, SEQ ID NO:128, & SEQ ID NO:134, and wherein the target hybridizing sequence of the fourth amplification oligomer is optionally joined at its 5' end to a promoter sequence, and wherein the target hybridizing sequence of the second amplification oligomer and the target hybridizing sequence of the fourth amplification oligomer are different sequences. In some aspects, the target hybridizing sequence of the fourth amplification oligomer is joined to a promoter sequence is a T7 promoter sequence, preferably wherein the promoter sequence consists of SEQ ID NO:179. In some aspects, the fourth amplification oligomer comprises a sequence that is selected from the group consisting of: SEQ ID NO:74, SEQ ID NO:75, SEQ ID NO:78, SEQ ID NO:79, SEQ ID NO:80, SEQ ID NO:87, and SEQ ID NO:89. In some aspects, the amplification step (b) is performed with the detection step (c). In some aspects, before the amplification step (b), the method further comprises purifying the Zika virus target sequence away from one or more components of the sample. In some aspects, the purifying step comprises contacting the sample with at least one capture probe oligomer comprising a target-hybridizing sequence covalently attached to a moiety that binds to an immobilized probe, wherein the target-hybridizing sequence is selected from the group consisting of SEQ ID NOs:166 to 178. In some aspects, the moiety comprises a nucleic acid sequence selected from the group consisting of SEQ ID NO:181 and SEQ ID NO:182. In some aspects, the immobilized probe comprises a nucleic acid sequence consisting of SEQ ID NO:180. In some aspects, the capture probe oligomer comprises a nucleic acid sequence selected from the group consisting of SEQ ID NOs:153 to 165. In some aspects, the in vitro amplification reaction is an isothermal amplification reaction. In some aspects, the in vitro amplification reaction is a TMA reaction.

Further disclosed herein are methods for determining the presence or absence of a Zika virus nucleic acid in a sample, the method comprising the steps of: (A) contacting a sample with a combination of at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence; (B) performing an in vitro nucleic acid amplification reaction, wherein any Zika virus target sequence present in the sample is used as a template for generating an amplification product; and (C) detecting the presence or absence of the amplification product, thereby determining the presence or absence of the Zika virus nucleic acid in the sample. In some aspects, the target hybridizing sequence of the first amplification oligomer is contained within SEQ ID NO:4. In some aspects, the target hybridizing sequence of the first amplification oligomer contains SEQ ID NO:2. In some aspects, the first amplification oligomer comprises a sequence selected from the group consisting of: SEQ ID NO:2, SEQ ID NO:3, SEQ ID NO:4, SEQ ID NO:5, SEQ ID NO:28, SEQ ID NO:29, SEQ ID NO:30, SEQ ID NO:31, SEQ ID NO:32, SEQ ID NO:33, SEQ ID NO:34, and SEQ ID NO:35. In some aspects, the target hybridizing sequence of the second amplification oligomer is contained within SEQ ID NO:152. In some aspects, the target hybridizing sequence of the second amplification oligomer contains SEQ ID NO:148. In some aspects, the target hybridizing sequence of the second amplification oligomer contains SEQ ID NO:149. In some aspects, the second amplification oligomer is joined at its 5' end to a promoter sequence that is a T7 promoter sequence. In some aspects, the T7 promoter sequence consists of SEQ ID NO:179. In some aspects, the target hybridizing sequence of the second amplification oligomer is selected from the group consisting of: SEQ ID NO:111, SEQ ID NO:116, SEQ ID NO:117, SEQ ID NO:122, SEQ ID NO:135, SEQ ID NO:136, SEQ ID NO:137, and SEQ ID NO:138. In some aspects, the second amplification oligomer comprises a sequence selected from the group consisting of: SEQ ID NO:90, SEQ ID NO:91, SEQ ID NO:92, SEQ ID NO:93, SEQ ID NO:94, SEQ ID NO:95, SEQ ID NO:96, and SEQ ID NO:97. In some aspects, the combination of first amplification oligomer and second amplification oligomer comprise nucleic acid sequences selected from the group consisting of: (i) SEQ ID NO:30 and SEQ ID NO:92; (ii) SEQ ID NO:30 and SEQ ID NO:94; (iii) SEQ ID NO:30 and SEQ ID NO:95 (iv) SEQ ID NO:35 and SEQ ID NO:92; (v) SEQ ID NO:35 and SEQ ID NO:94; and (vi) SEQ ID NO:35 and SEQ ID NO:95. In some aspects, the combination further comprises a third amplification oligomer for amplifying a target sequence of a Zika virus nucleic acid, wherein the third amplification oligomer comprises a target hybridizing sequence selected from the group consisting of: SEQ ID NO:111, SEQ ID NO:116, SEQ ID NO:117, SEQ ID NO:122, SEQ ID NO:135, SEQ ID NO:136, SEQ ID NO:137, & SEQ ID NO:138, wherein, optionally, the target hybridizing sequence of the third amplification oligomer is joined at it 5' end to a promoter sequence, and wherein the target hybridizing sequence of the second amplification oligomer and the target hybridizing sequence of the third amplification oligomer are different sequences. In some aspects, the target hybridizing sequence of the third amplification oligomer is joined at its 5' end to a promoter sequence that is a T7 promoter sequence, preferably wherein the promoter sequence consists of SEQ ID NO:179. In some aspects, the third amplification oligomer comprises a sequence selected from the group consisting of: SEQ ID NO:90, SEQ ID NO:91, SEQ ID NO:92, SEQ ID NO:93, SEQ ID NO:94, SEQ ID NO:95, SEQ ID NO:96, and SEQ ID NO:97. In some aspects, the detecting step comprises contacting the in vitro amplification reaction with at least one detection probe oligomer, wherein the detection probe oligomer comprises: (i) a target hybridizing sequence and, optionally, one or more nucleobases that are not complementary to the Zika virus target nucleic acid, and (ii) a detectable label. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NO:54, SEQ ID NO:55, and SEQ ID NO:58. In some aspects, the target hybridizing sequence of the detection probe oligomer comprises the one or more nucleobases that are not complementary to the target nucleic acid. In some aspects, the target hybridizing sequence of the detection probe oligomer comprises at either its 3' end or its 5' end from 3 to 7 contiguous nucleobases that are not complementary to the target sequence of the Zika virus nucleic acid. In some aspects, the 3 to 7 contiguous nucleobases that are not complementary to the target sequence, are complementary to a portion of the target hybridizing sequence of the detection probe oligomer. In some aspects, the detectable label is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and wherein the detection probe oligomer further comprises a quenching compound. In some aspects, the detection probe oligomer is selected from the group consisting of TaqMan detection probes, molecular beacons, and molecular torches. In some aspects, the detection probe oligomer comprises a sequence selected from the group consisting of: SEQ ID NO:54, SEQ ID NO:55, & SEQ ID NO:58. In some aspects, the combination of the first amplification oligomer and the second amplification oligomer is selected from the group consisting of: (i) SEQ ID NO:30 and SEQ ID NO:92; (ii) SEQ ID NO:30 and SEQ ID NO:94; (iii) SEQ ID NO:30 and SEQ ID NO:95 (iv) SEQ ID NO:35 and SEQ ID NO:92; (v) SEQ ID NO:35 and SEQ ID NO:94; and (vi) SEQ ID NO:35 and SEQ ID NO:95, and wherein the detection probe oligomer comprises a target hybridizing sequence consisting of SEQ ID NO:58, and the detectable label consists of an acridinium ester label. In some aspects, the combination further comprises a third amplification oligomer for amplifying a target sequence of a Zika virus nucleic acid, wherein the third amplification oligomer comprises a target hybridizing sequence selected from the group consisting of: SEQ ID NO:111, SEQ ID NO:116, SEQ ID NO:117, SEQ ID NO:122, SEQ ID NO:135, SEQ ID NO:136, SEQ ID NO:137, & SEQ ID NO:138, wherein, optionally, the target hybridizing sequence of the third amplification oligomer is joined at it 5' end to a promoter sequence, and wherein the target hybridizing sequence of the second amplification oligomer and the target hybridizing sequence of the third amplification oligomer are different sequences. In some aspects, the target hybridizing sequence of the third amplification oligomer is joined at its 5' end to a promoter sequence that is a T7 promoter sequence, preferably wherein the promoter sequence consists of SEQ ID NO:179. In some aspects, the third amplification oligomer comprises a sequence selected from the group consisting of: SEQ ID NO:90, SEQ ID NO:91, SEQ ID NO:92, SEQ ID NO:93, SEQ ID NO:94, SEQ ID NO:95, SEQ ID NO:96, and SEQ ID NO:97. In some aspects, the amplification step (b) is performed with the detection step (c). In some aspects, before the amplification step (b), the method further comprises purifying the Zika virus target sequence away from one or more components of the sample. In some aspects, the purifying step comprises contacting the sample with at least one capture probe oligomer comprising a target-hybridizing sequence covalently attached to a moiety that binds to an immobilized probe, wherein the target-hybridizing sequence is selected from the group consisting of SEQ ID NOs:166 to 178. In some aspects, the moiety comprises a nucleic acid sequence selected from the group consisting of SEQ ID NO:181 and SEQ ID NO:182. In some aspects, the immobilized probe comprises a nucleic acid sequence consisting of SEQ ID NO:180. In some aspects, the capture probe oligomer comprises a nucleic acid sequence selected from the group consisting of SEQ ID NOs:153 to 165. In some aspects, the in vitro amplification reaction is an isothermal amplification reaction. In some aspects, the in vitro amplification reaction is a TMA reaction.

Further disclosed herein are methods for determining the presence or absence of a Zika virus nucleic acid in a sample, the method comprising the steps of: (A) contacting a sample with a combination of at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; (B) performing an in vitro nucleic acid amplification reaction, wherein any Zika virus target sequence present in the sample is used as a template for generating an amplification product; and (C) detecting the presence or absence of the amplification product, thereby determining the presence or absence of the Zika virus nucleic acid in the sample. In some aspects, the target hybridizing sequence of the first amplification oligomer is contained within SEQ ID NO:6. In some aspects, the target hybridizing sequence of the first amplification oligomer contains SEQ ID NO:7. In some aspects, the target hybridizing sequence of the first amplification oligomer contains SEQ ID NO:8. In some aspects, the first amplification oligomer comprises a target hybridizing sequence selected from the group consisting of: SEQ ID NOs:36 to 48. In some aspects, the target hybridizing sequence of the second amplification oligomer is selected from the group consisting of: SEQ ID NO:123, SEQ ID NO:124, SEQ ID NO:139, SEQ ID NO:140, SEQ ID NO:141, SEQ ID NO:142, SEQ ID NO:143, SEQ ID NO:144, SEQ ID NO:145, SEQ ID NO:146, & SEQ ID NO:147. In some aspects, the second amplification oligomer is joined at its 5' end to a promoter sequence that is a T7 promoter sequence. In some aspects, the T7 promoter sequence consists of SEQ ID NO:179. In some aspects, the second amplification oligomer comprises a sequence selected from the group consisting of: SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:109, and SEQ ID NO:110. In some aspects, the combination of first amplification oligomer and second amplification oligomer comprise nucleic acid sequences selected from the group consisting of: (i) SEQ ID NO:36 and SEQ ID NO:103; (ii) SEQ ID NO:36 and SEQ ID NO:104; (iii) SEQ ID NO:36 and SEQ ID NO:105; (iv) SEQ ID NO:37 and SEQ ID NO:102; (v) SEQ ID NO:37 and SEQ ID NO:103; (vi) SEQ ID NO:37 and SEQ ID NO:105; (vii) SEQ ID NO:38 and SEQ ID NO:105; (viii) SEQ ID NO:39 and SEQ ID NO:104; (ix) SEQ ID NO:39 and SEQ ID NO:105; (x) SEQ ID NO:39 and SEQ ID NO:106; (xi) SEQ ID NO:41 and SEQ ID NO:104; (xii) SEQ ID NO:41 and SEQ ID NO:106; (xiii) SEQ ID NO:43 and SEQ ID NO:106; (xiv) SEQ ID NO:45 and SEQ ID NO:103; (xv) SEQ ID NO:45 and SEQ ID NO:105; (xvi) SEQ ID NO:45 and SEQ ID NO:106; (xvii) SEQ ID NO:46 and SEQ ID NO:106; (xviii) SEQ ID NO:47 and SEQ ID NO:104; and (xix) SEQ ID NO:47 and SEQ ID NO:106. In some aspects, the detecting step comprises contacting the in vitro amplification reaction with at least one detection probe oligomer, wherein the detection probe oligomer comprises: (i) a target hybridizing sequence and, optionally, one or more nucleobases that are not complementary to the Zika virus target nucleic acid, and (ii) a detectable label. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NO:56, SEQ ID NO:57, and SEQ ID NOs:66 to 73. In some aspects, the target hybridizing sequence of the detection probe oligomer comprises the one or more nucleobases that are not complementary to the target nucleic acid. In some aspects, the target hybridizing sequence of the detection probe oligomer comprises at either its 3' end or its 5' end from 3 to 7 contiguous nucleobases that are not complementary to the target sequence of the Zika virus nucleic acid. In some aspects, the 3 to 7 contiguous nucleobases that are not complementary to the target sequence, are complementary to a portion of the target hybridizing sequence of the detection probe oligomer. In some aspects, the detectable label is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and wherein the detection probe oligomer further comprises a quenching compound. In some aspects, the detection probe oligomer is selected from the group consisting of TaqMan detection probes, molecular beacons, and molecular torches. In some aspects, the target hybridizing sequence does not comprise the one or more nucleobases that are not complementary to the target nucleic acid. In some aspects, the combination of the first amplification oligomer and the second amplification oligomer is selected from the group consisting of: (i) SEQ ID NO:36 and SEQ ID NO:103; (ii) SEQ ID NO:36 and SEQ ID NO:104; (iii) SEQ ID NO:36 and SEQ ID NO:105; (iv) SEQ ID NO:37 and SEQ ID NO:102; (v) SEQ ID NO:37 and SEQ ID NO:103; (vi) SEQ ID NO:37 and SEQ ID NO:105; (vii) SEQ ID NO:38 and SEQ ID NO:105; (viii) SEQ ID NO:39 and SEQ ID NO:104; (ix) SEQ ID NO:39 and SEQ ID NO:105; (x) SEQ ID NO:39 and SEQ ID NO:106; (xi) SEQ ID NO:41 and SEQ ID NO:104; (xii) SEQ ID NO:41 and SEQ ID NO:106; (xiii) SEQ ID NO:43 and SEQ ID NO:106; (xiv) SEQ ID NO:45 and SEQ ID NO:103; (xv) SEQ ID NO:45 and SEQ ID NO:105; (xvi) SEQ ID NO:45 and SEQ ID NO:106; (xvii) SEQ ID NO:46 and SEQ ID NO:106; (xviii) SEQ ID NO:47 and SEQ ID NO:104; and (xix) SEQ ID NO:47 and SEQ ID NO:106, and wherein the detection probe oligomer comprises a target hybridizing sequence consisting of SEQ ID NO:61, and the detectable label consists of an acridinium ester label. In some aspects, the amplification step (b) is performed with the detection step (c). In some aspects, before the amplification step (b), the method further comprises purifying the Zika virus target sequence away from one or more components of the sample. In some aspects, the purifying step comprises contacting the sample with at least one capture probe oligomer comprising a target-hybridizing sequence covalently attached to a moiety that binds to an immobilized probe, wherein the target-hybridizing sequence is selected from the group consisting of SEQ ID NOs:166 to 178. In some aspects, the moiety comprises a nucleic acid sequence selected from the group consisting of SEQ ID NO:181 and SEQ ID NO:182. In some aspects, the immobilized probe comprises a nucleic acid sequence consisting of SEQ ID NO:180. In some aspects, the capture probe oligomer comprises a nucleic acid sequence selected from the group consisting of SEQ ID NOs:153 to 165. In some aspects, the in vitro amplification reaction is an isothermal amplification reaction. In some aspects, the in vitro amplification reaction is a TMA reaction.

Further disclosed herein are multiplex methods for determining the presence or absence of a Zika virus nucleic acid in a sample, the method comprising the steps of: (A) contacting a sample with at least two combinations of at least two amplification oligomers, each for amplifying a separate target sequence of a Zika virus target nucleic acid, wherein comprising at least two combinations of at least two amplification oligomers selected from the group consisting of: (1) (i) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with (ii) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence; (2) (i) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with (ii) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; (3) (i) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence, combined with (ii) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; and (4) (i) at least two amplification oligomers for amplifying a target sequence of a Zika virus target nucleic acid, wherein the target sequence consists essentially of SEQ ID NO:189, accounting for complements thereof, RNA equivalents thereof, or both, wherein the first amplification oligomer and the second amplification oligomer are configured to hybridize to opposite ends of the target sequence, to generate amplification products; wherein a first amplification oligomer comprises a target hybridizing sequence that is from 17 to 26 contiguous nucleobases in length, and wherein a second amplification oligomer comprises a target hybridizing sequence that is from 17 to 26 contiguous nucleobases in length and, optionally, joined at its 5' end to a promoter sequence, combined with (ii) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:187, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 19 to 25 contiguous nucleobases in length and, optionally, joined at its 5' end to a promoter sequence, and combined with (iii) at least two amplification oligomers for amplifying a Zika virus nucleic acid in a sample, the oligomer combination comprising: at least two amplification oligomers for amplifying a target sequence of a Zika virus target nucleic acid, wherein the target sequence consists essentially of SEQ ID NO:188, accounting for complements thereof, RNA equivalents thereof, or both, wherein the first amplification oligomer and the second amplification oligomer are configured to hybridize to opposite ends of the target sequence, including complements thereof and/or RNA equivalents thereof, to generate amplification products; wherein a first amplification oligomer comprises a target hybridizing sequence that is from 19 to 23 contiguous nucleobases in length, and wherein a second amplification oligomer comprises a target hybridizing sequence that is from 17 to 23 contiguous nucleobases in length and, optionally, joined at its 5' end to a promoter sequence; (B) performing an in vitro nucleic acid amplification reaction, wherein for (A)(1) the at least two amplification oligomer of (i) and/or (ii) hybridize their respective target sequence present in the sample to generate an amplification product(s); or wherein for (A)(2) the at least two amplification oligomer of (i) and/or (ii) hybridize their respective target sequence present in the sample to generate an amplification product(s); or wherein for (A)(3) the at least two amplification oligomer of (i) and/or (ii) hybridize their respective target sequence present in the sample to generate an amplification product(s); or wherein for (A)(4) the at least two amplification oligomer of (i) and/or (ii) and/or (iii) hybridize their respective target sequence present in the sample to generate an amplification product(s); and (C) detecting the presence or absence of the amplification product(s), thereby determining the presence or absence of the Zika virus nucleic acid in the sample. In some aspects, the detecting step comprises contacting the in vitro amplification reaction with at least one detection probe oligomer, wherein the detection probe oligomer comprises: (i) a target hybridizing sequence configured to hybridize under stringent conditions to a target sequence of a Zika virus nucleic acid, and, optionally, one or more nucleobases that are not complementary to the Zika virus target nucleic acid, and (ii) a detectable label, wherein the Zika virus target nucleic acid sequence is selected from the group consisting of: SEQ ID NO:187, SEQ ID NO:188, & SEQ ID NO:189, including a complement thereof, and/or an RNA equivalent thereof. In some aspects, the detection probe oligomer comprises a target hybridizing sequence that is configured to selectively hybridize a sequence selected from the group consisting of: SEQ ID NO:194, SEQ ID NO:195, SEQ ID NO:196, SEQ ID NO:197, & SEQ ID NO:198, including a complement thereof, and/or an RNA equivalent thereof. In some aspects, the target hybridizing sequence of the detection probe oligomer is from 17 to 23 contiguous nucleobases in length. In some aspects, the target hybridizing sequence of the detection probe oligomer is selected from the group consisting of: SEQ ID NOs:54 to 63 and 66 to 73. In some aspects the combinations of amplification oligomers and detection probe oligomers are: for (A)(1)(i), (A)(2)(i) or (A)(4)(i) the detection probe oligomer comprises a nucleic acid sequence selected from the group consisting of SEQ ID NOs:56, 57, & 64 to 73; for (A)(1)(ii), (A)(3)(i), or (A)(4)(ii) the detection probe oligomer comprises a nucleic acid sequence selected from the group consisting of SEQ ID NOs:54, 55, & 58; or for (A)(2)(ii)m (A)(3)(ii), or (A)(4)(iii) the detection probe oligomer is selected from the group consisting of SEQ ID NOs:59 to 63. In some aspects, the detection probe oligomer is selected from the group consisting of TaqMan detection probes, molecular beacons, and molecular torches. In some aspects, the detectable label is a fluorescent label, a luminescent label, a chromophore label, a radionuclide label, a ligand label, an enzyme label, or a reactive group label. In some aspects, the detectable label is a chemiluminescent label. In some aspects, the detectable label is an acridinium ester. In some aspects, the detectable label is a fluorescent label and wherein the detection probe oligomer further comprises a quenching compound. In some aspects, the amplification step (b) is performed with the detection step (c). In some aspects, before the amplification step (b), the method further comprises purifying the Zika virus target sequence away from one or more components of the sample. In some aspects, the purifying step comprises contacting the sample with at least one capture probe oligomer comprising a target-hybridizing sequence covalently attached to a moiety that binds to an immobilized probe, wherein the target-hybridizing sequence is selected from the group consisting of SEQ ID NOs:166 to 178. In some aspects, the moiety comprises a nucleic acid sequence selected from the group consisting of SEQ ID NO:181 and SEQ ID NO:182; wherein the immobilized probe comprises a nucleic acid sequence consisting of SEQ ID NO:180; or both. In some aspects, the capture probe oligomer comprises a nucleic acid sequence selected from the group consisting of SEQ ID NOs:153 to 165. In some aspects, the in vitro amplification reaction is an isothermal amplification reaction. In some aspects, the in vitro amplification reaction is a TMA reaction. These and other aspects will become evident upon reference to the following detailed description and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain Zika virus or components thereof, such as nucleic acids or fragments of nucleic acids. For the avoidance of doubt, a medium containing a synthetic in vitro transcript comprising a Zika virus nucleic acid is considered a sample. Samples include "biological samples" which include any material derived from a living or dead human that may contain Zika virus or target nucleic acid derived therefrom. Biological samples include, but are not limited to, whole blood, red blood cells, peripheral blood, plasma, serum, lymph node, gastrointestinal tissue (e.g., liver), material collected using a vaginal swab, material collected using a cervical brush, material collected via bronchoscopy, material collected via bronchoaveolar lavage, tissue, sputum, saliva or other body fluids or materials. Also, samples may include processed or purified samples, such as those obtained from passing samples over or through a filtering device, or capturing a nucleic acid of interest in a target capture reaction, or following centrifugation, or by adherence to a medium, matrix, or support.

"Nucleic acid" refers to a multimeric compound comprising two or more covalently bonded nucleosides and/or nucleoside analogs and/or base analogs, linked together by phosphodiester bonds or other linkages to form a polynucleotide. Sugar moieties of the nucleic acid may be ribose and/or deoxyribose. Sugar moieties may comprise substitutions such as, for example, 2'-methoxy substitutions and 2'-halide substitutions (e.g., 2'-F). Synthetic methods for making nucleic acids in vitro are well-known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Synthetic nucleic acids, e.g., DNA, RNA, DNA/RNA chimerics, (including when non-natural nucleotides or analogues are included therein), are typically synthesized "3'-to-5'," i.e., by the addition of nucleotides to the 5'-terminus of a growing nucleic acid.

A "target nucleic acid" as used herein is a nucleic acid comprising a target sequence to be amplified. Target nucleic acids may be DNA or RNA as described herein, and may be either single-stranded or double-stranded. Target nucleic acids may be any of the nucleic acid obtained directly from a sample, a synthetic nucleic acid construct, and a nucleic acid amplification product. The target nucleic acid may include other sequences besides the target sequence, which may not be amplified. For example, a target nucleic acid can be an entire genome, a gene, a region within a genome, an expression product, a chimeric nucleic acid, an amplification product, or a target sequence.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes. Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. A target sequence consisting essentially of a certain SEQ ID NO (e.g., SEQ ID NOs:187, 188 or 189) means that the target sequence may have from 0 to 20 fewer nucleotides on one or both ends of the referenced sequence. Preferably, a target sequence consisting essentially of SEQ ID NO:189 has from 0 to 3 fewer nucleotides on the 5' end and from 0 to 8 fewer nucleotides on the 3' end compared SEQ ID NO:189. Preferably, a target sequence consisting essentially of SEQ ID NO:187 has from 0 to 6 fewer nucleotides on the 5' end compared to SEQ ID NO:187. Preferably, a target sequence consisting essentially of SEQ ID NO:188 has from 0 to 4 fewer nucleotides on the 3' end compared to SEQ ID NO:188.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to various genotypes of Zika virus species isolates. It is understood that other reasons exist for configuring a target-hybridizing sequence to have less than 100% complementarity to a target nucleic acid.

The term "targets a sequence" as used herein in reference to a region of Zika virus nucleic acid refers to a process whereby an oligonucleotide hybridizes to the target sequence in a manner that allows for target capture, amplification and/or detection as described herein. In one preferred embodiment, the oligonucleotide is complementary with the targeted Zika virus nucleic acid sequence and contains no mismatches. In another preferred embodiment, the oligonucleotide is complementary but contains 1, 2, 3, 4, or 5 mismatches with the targeted Zika virus nucleic acid sequence. Preferably, the oligonucleotide that hybridizes to the Zika virus nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing sequence of an amplification oligonucleotide, detection probe, or other oligonucleotide is designed to have a polynucleotide sequence that could target a sequence of the referenced Zika virus target nucleic acid. Such an oligonucleotide is not limited to targeting that sequence only, but is rather useful as a composition, in a kit, or in a method for targeting a Zika virus target nucleic acid. The oligonucleotide is designed to function as a component of an assay for amplification and detection of Zika virus from a sample, and therefore is designed to target Zika virus in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 900 nt residues, including all whole numbers therein. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectable moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same reference sequence (e.g., a primer sequence hybridizing to a target nucleic acid sequence). It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%, including all whole and partial numbers therein. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase "or its complement, or an RNA equivalent, or DNA/RNA chimeric thereof," with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence. Similarly, the phrase "or its complement, or a DNA equivalent or DNA/RNA chimeric thereof," with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. The nucleic acid amplification reaction can be through an extension of the 3' end of the amplification oligomer. The amplification can also be through a promoter sequence attached to the amplification oligomer. Examples of amplification oligomers include, but are not limited to, primers and promoter-based amplification oligomers. Promoter-based amplification oligomers are referred to as promoter primers, promoter providers, T7 amplification oligomers, T7 providers and T7 primers.

As used herein, a "primer" is an amplification oligomer that hybridizes to a target nucleic acid and contains a 3' OH end that is extended by a polymerase in an amplification process.

As used herein, a "promoter-based amplification oligomer," referred to also as "promoter primers," "promoter providers," "T7 amplification oligomers," "T7 providers" and "T7 primers," refers to an oligonucleotide comprising at least first and second regions. The "first region" of a promoter-based amplification oligonucleotide comprises a base sequence that hybridizes to a target sequence (e.g., a target-hybridizing sequence), where the first region is situated 3', but not necessarily adjacent to, a second region that is a promoter sequence. In some instances, the 3' end of the first region is not extended by a polymerase, and the promoter-based amplification oligomer participates in or facilitates amplification by the promoter sequence. In certain instances, there is an intervening sequence or sequences between the target-hybridizing sequence at the 3' end of the amplification oligomer and the promoter sequence at the 5' end of the amplification oligomer. One example of an intervening sequence is a tag sequence that is useful as an added sequence in an amplification product.

As used herein, a "promoter" is a specific nucleic acid sequence that is recognized by a DNA-dependent RNA polymerase ("transcriptase") as a signal to bind to the nucleic acid and begin the transcription of RNA at a specific site.

"Amplification" refers to any known procedure for obtaining multiple copies of a target nucleic acid sequence or its complement or fragments thereof. The multiple copies may be referred to as amplicons or amplification products. Known amplification methods include, for example, replicase-mediated amplification (see, e.g., U.S. Pat. No. 4,786,600), polymerase chain reaction (PCR; see, e.g., U.S. Pat. Nos. 4,683,195; 4,683,202; and 4,800,159), ligase chain reaction (LCR; see, e.g., U.S. Pat. Nos. 5,427,930 and 5,516,663), strand-displacement amplification (SDA; see, e.g., U.S. Pat. Nos. 5,422,252; 5,547,861; and 5,648,211), and transcription-mediated or transcription-associated amplification.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription-associated amplification methods are embodiments of amplification methods used for detection of Zika virus target sequences as described herein. Variations of transcription-associated amplification are well-known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers described herein may comprise non-target specific sequences, such as those added by a tag sequence on an amplification oligomer, and/or modified nucleotides included in the amplification oligomers or in the dNTP mixture. Amplicons can be double-stranded or single-stranded and can include DNA, RNA, or both. For example, DNA-dependent RNA polymerase transcribes single-stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination described herein. Such representation is not meant to limit the amplicon to the representation shown. Skilled artisans in possession of the instant disclosure will use amplification oligomers and polymerase enzymes to generate any of the numerous types of amplicons, all within the spirit and scope of the current disclosure.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers (e.g., the 5' promoter sequence of the amplification oligomer) and molecular beacons and torches (e.g., one or both of the stem members).

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof (e.g., DNA/RNA chimerics) and they may be labeled or unlabeled. Detection probes may further include modifications such as, e.g., 2'-O-methyl linkages. A detection probe may comprise target-specific sequences and other sequences that contribute to the three-dimensional conformation of the probe (see, e.g., U.S. Pat. Nos. 5,118, 801; 5,312,728; 6,849,412; 6,835,542; 6,534,274; and 6,361,945; and US Patent Application Pub. No. 20060068417).

As used herein, a "label" refers to a moiety or compound joined directly or indirectly to a probe that is detected or leads to a detectable signal. Direct labeling can occur through bonds or interactions that link the label to the probe. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay see, e.g., U.S. Pat. Nos. 5,283,174; 5,656,207; and 5,658,737. Labels include chemiluminescent compounds, e.g., acridinium ester ("AE") compounds that include standard AE and derivatives (see, e.g., U.S. Pat. Nos. 5,656,207; 5,658,737; and 5,639,604). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N Y, 1989, Chapter 10, incorporated by reference herein. See also U.S. Pat. Nos. 5,658,737; 5,656,207; 5,547,842; 5,283,174; and 4,581,333). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579).

"Capture probe," "capture oligonucleotide," "target capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a target sequence-binding region (e.g., target-hybridizing sequence) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that directly or indirectly joins a capture oligomer to a solid support. An immobilized probe joined to a solid support facilitates separation of a capture probe bound target from unbound material in a sample. Immobilized probes, solid supports and capture oligomers are described in the literature (e.g., U.S. Pat. No. 6,110,678).

By "complementary" is meant that the nucleotide sequences of similar regions of two single-stranded nucleic acids, or two different regions of the same single-stranded nucleic acid, have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T, or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues that are not complementary. Sufficiently complementary contiguous sequences typically are at least 80% (including all whole and partial numbers from 80% to just less than 100%) complementary to a sequence to which an oligomer is intended to specifically hybridize and that stably hybridize with its target sequence under appropriate hybridization conditions, (see, e.g., Sambrook et al., *Molecular Cloning, A Laboratory Manual,* $2^{nd}$ ed. (Cold Spring Harbor Laboratory Press, Cold Spring Harbor, N.Y., 1989 at §§ 1.90-1.91, 7.37-7.57, 9.47-9.51 and 11.47-11.57, particularly §§ 9.50-9.51, 11.12-11.13, 11.45-11.47 and 11.55-11.57).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized Thus, a probe hybridizes to a target sequence or replicate thereof to a sufficiently greater extent than to a non-target sequence, to enable one having ordinary skill in the art to accurately detect or quantitate RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual,* $2^{nd}$ ed. (Cold Spring Harbor Laboratory Press, Cold Spring Harbor, N Y, 1989 at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

"Sample preparation" refers to any steps or method that treats a sample for subsequent amplification and/or detection of Zika virus nucleic acids present in the sample. Sample preparation may include physical/mechanical disruption and/or chemical lysis of cellular components to release intracellular components into a substantially aqueous or organic phase and removal of debris, such as by using filtration, centrifugation or adsorption. Sample preparation may include use of a target capture oligonucleotide that selectively or non-specifically capture a target nucleic acid and separate it from other sample components (e.g., as described in U.S. Pat. No. 6,110,678 and International Patent Application Pub. No. WO 2008/016988). Sample preparation can include pooling a plurality of samples into a single pooled batch. Preferably for pooling, an aliquot of each sample is pooled into the larger batch. More preferably for pooling, an aliquot of each sample is first lysed and then pooled into the larger batch. The larger batch of pooled samples can be from a plurality of samples wherein the plurality is from 2 to about 200 individual samples.

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

"Sample Transport Solution" generally refers to a solution containing 15 mM sodium phosphate monobasic, 15 mM sodium phosphate dibasic, 1 mM EDTA, 1 mM EGTA, and 110 mM lithium lauryl sulfate (LLS), at pH 6.7.

"Target Capture Reagent" generally refers to a solution containing 250 mM HEPES, 310 mM lithium hydroxide, 1.88 M lithium chloride, 100 mM EDTA, at pH 6.4, and 250 µg/ml of magnetic particles (1 micron SERA-MAG™ MG-CM particles, GE Healthcare Lifesciences) with $dT_{14}$ oligomers covalently bound thereto.

"Wash Solution" generally refers to a solution containing 10 mM HEPES, 150 mM sodium chloride, 6.5 mM sodium hydroxide, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5.

"Probe Reagent" generally refers to a solution containing one or more labeled detection probes in a solution made up of 100 mM lithium succinate, 2% (w/v) LLS, 15 mM mercaptoethanesulfonate, 1.2 M lithium chloride, 20 mM EDTA, and 3% (v/v) ethanol, at pH 4.7.

"Amplification Reagent" generally refers to a concentrated mixture mixed with other reaction components to produce a mixture containing 47.6 mM Na-HEPES, 12.5 mM N-acetyl-L-cysteine, 2.5% TRITON™ X-100, 54.8 mM KCl, 23 mM MgCl2, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM Na2EDTA, 5% v/v glycerol, 2.9% trehalose, 0.225% ethanol, 0.075% methylparaben, 0.015% propylparaben, and 0.002% Phenol Red, at pH 7.5-7.6, although other formulations of amplification reagent may function equally well. Primers may be added to the amplification reagent or added to amplification reactions separate from the amplification reagent. Enzymes in an amplification reagent can include one or more of Moloney Murine Leukemia Virus Reverse Transcriptase (MMLV-RT) and bacteriophage T7 RNA polymerase for which units are functionally defined as: 1 U of MMLV-RT incorporates 1 nmol of dTTP in 10 min at 37° C. using 200-400 micromolar oligo dT-primed poly(A) as template, and 1 U of T7 RNA polymerase incorporates 1 nmol of ATP into RNA in 1 hr at 37° C. using a DNA template containing a T7 promoter.

"Hybridization Reagent" generally refers to a solution made up of 100 mM succinic acid, 2% (w/v) LLS, 100 mM lithium hydroxide, 15 mM aldrithiol-2, 1.2 M lithium chloride, 20 mM EDTA, and 3.0% (v/v) ethanol, at pH 4.7.

"Selection Reagent" generally refers to a solution containing 600 mM boric acid, 182.5 mM sodium hydroxide, 1% (v/v) octoxynol (TRITON® X-100), at pH 8.5.

"Detection Reagents" include "Detect Reagent I," which generally refers to a solution containing 1 mM nitric acid and 32 mM hydrogen peroxide, and "Detect Reagent II," which generally refers to a solution of 1.5 M sodium hydroxide.

DETAILED DESCRIPTION

Described herein are compositions, kits, and methods for amplifying and detecting Zika virus nucleic acid from a sample. Preferably, the samples are biological samples. The compositions, kits, and methods provide oligonucleotide sequences that recognize target sequences of the Zika virus genome. Such oligonucleotides may be used as amplification oligonucleotides. Other oligonucleotides may be used as probes for detecting amplified sequences of Zika virus, or for capture of Zika virus target nucleic acid.

The methods provide for the sensitive and specific detection of Zika virus nucleic acids. The methods include performing a nucleic acid amplification of a Zika virus target nucleic acid and detecting the amplified product by, for example, specifically hybridizing the amplified product with a nucleic acid detection probe that provides a signal to indicate the presence of Zika virus in the sample. The amplification step includes contacting the sample with one or more amplification oligomers specific for a target sequence in a Zika virus target nucleic acid to produce an amplified product if Zika virus nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target sequence, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1).

Preferred compositions described herein are configured to specifically hybridize to Zika virus nucleic acids from one or more Zika virus strains and, preferably with minimal cross-reactivity to other, non-Zika virus nucleic acids suspected of being in a sample (e.g., other blood borne pathogens). In some aspects, the disclosed compositions are configured to specifically hybridize to Zika virus nucleic acid with minimal cross-reactivity to one or more of hepatitis C virus (HCV), human immunodeficiency virus 1 (HIV 1), hepatitis B virus (HBV), Dengue virus *plasmodium, babesia*, and West Nile virus. In one aspect, the compositions are part of a multiplex system that further includes components and methods for detecting one of more of these organisms.

SEQ ID NO: 1. (5' to 3') Gen Bank Accession Number/Version Number/GI Number AY632535.2 GI:226374362.

```
agttgttgatctgtgtgagtcagactgcgacagttcgagtctgaagcgag
agctaacaacagtatcaacaggtttaatttggatttggaaacgagagttt
ctggtcatgaaaaacccaaagaagaaatccggaggatccggattgtcaa
tatgctaaaacgcggagtagcccgtgtaaacccctttgggaggtttgaaga
ggttgccagccggacttctgctgggtcatggacccatcagaatggattgg
cgatactagcctattgagatttacagcaatcaagccatcactgggcctta
tcaacagatggggttccgtgggaaaaaagaggctatggaaataataaag
aagttcaagaaagatcttgctgccatgttgagaataatcaatgctaggaa
agagaggaagagacgtggcgcagacaccagcatcggaatcattggcctcc
tgctgactacagccatggcagcagagatcactagacgcgggagtgcatac
tacatgtacttggataggagcgatgccgggaaggccatttcgtttgctac
cacattgggagtgaacaagtgccacgtacagatcatggacctcgggcaca
tgtgtgacgccaccatgagttatgagtgccctatgctggatgagggagtg
gaaccagatgatgtcgattgctggtgcaacacgacatcaacttgggttgt
gtacggaacctgtcatcacaaaaaaggtgaggcacggcgatctagaagag
ccgtgacgctcccttctcactctacaaggaagttgcaaacgcggtcgcag
acctggttagaatcaagagaatacacgaagcacttgatcaaggttgaaaa
ctggatattcaggaacccgggtttgcgctagtggccgttgccattgcct
ggcttttgggaagctcgacgagccaaaaagtcatatacttggtcatgata
ctgctgattgccccggcatacagtatcaggtgcattggagtcagcaatag
agacttcgtggagggcatgtcaggtgggacctgggttgatgagtcttgga
acatggaggctgcgttaccgtgatggcacaggacaagccaacagtcgaca
tagagttggtcacgacgacggttagtaacatggccgaggtaagatcctat
tgctacgaggcatcgatatcggacatggcttcggacagtcgttgcccaac
acaaggtgaagcctaccttgacaagcaatcagacactcaatatgtctgca
aaagaacattagtggacagaggttgggaaacggttgtggactttttggc
aaagggagcttggtgacatgtgccaagtttacgtgttctaagaagatgac
cgggaagagcattcaaccggaaaatctggagtatcggataatgctatcag
tgcatggctcccagcatagcgggatgattggatatgaaactgacgaagat
agagcgaaagtcgaggttacgcctaattcaccaagagcggaagcaacctt
gggaggctttggaagcttaggacttgactgtgaaccaaggacaggcctt
acttttcagatctgtattacctgaccatgaacaataagcattggttggtg
cacaaagagtggtttcatgacatcccattgccttggcatgctggggcaga
caccggaactccacactggaacaacaaagaggcattggtagaattcaagg
atgcccacgccaagaggcaaaccgtcgtcgttctggggagccaggaagga
gccgttcacacggctctcgctggagctctagaggctgagatggatggtgc
aaagggaaggctgactctggccatttgaaatgccgcctaaaaatggacaa
gcttagattgaagggcgtgtcatattccttgtgcactgcggcattcacat
tcaccaaggtcccagctgaaacactgcatggaacagtcacagtggaggtg
cagtatgcagggacagatggaccctgcaagatcccagtccagatggcggt
ggacatgcagaccctgaccccagaggaaggctgataaccgccaaccccgt
gattactgaaagcactgagaactcaaagatgatgaggagcttgacccacc
atttgggattcttacattgtcataggagttggggacaagaaaatcaccc
accactggcataggagtggtagcaccatcggaaaggcatttgaggccact
gtgagaggcgccaagagaatggcagtcctgggggatacagcctgggactt
cggatcagtcgggggtgtgttcaactcactgggtaagggcattcaccaga
ttttggagcagccttcaaatcactgttttggaggaatgtcctggttctca
cagatcctcataggcacgctgctagtgtggttaggttttgaacacaaagaa
tggatctatctccctcacatgcttggccctgggggagtgatgatcttcc
tctccacggctgtttctgctgacgtggggtgctcagtggacttctcaaaa
aaggaaacgagatgtggcacggggtattcatctataatgatgtttgaagc
ctggagggaccggtacaagtaccatcctgactcccccccgcagattggcag
cagcagtcaagcaggcctgggaagagggatctgtgggatctcatccgtt
tcaagaatggaaaacatcatgtggaaatcagtagaaggggagctcaatgc
tatcctagaggagaatggagttcaactgacagttgagtgggatctgtaaa
aaacccatgtggagaggtccacaaagattgccagtgcctgtgaatgagc
tgcccatggctgaaagcctgggggaaatcgtattttgttagggcggca
aagaccaacaacagttttgttgtcgacggtgacacactgaaggaatgtcc
gcttgagcacagagcatggaatagttttcttgtggaggatcacgggtttg
gagtcttccacaccagtgtctggcttaaggtcagagaagattactcatta
gaatgtgacccagccgtcataggaacagctgttaaggggaaggaggccgc
gcacagtgatctgggctattggattgaaagtgaaaagaatgacacatgga
ggctgaagagggcccacctgattgagatgaaaacatgtgaatggccaaag
tctcacacattgtggacagatggagtagaagaaagtgatcttatcatacc
caagtctttagctggtccactcagccaccacaacaccagagaggttaca
gaacccaagtgaaagggccatggcacagtgaagagcttgaaatccggttt
gaggaatgtccaggcaccaaggtttacgtggaggagacatgcggaactag
aggaccatctctgagatcaactactgcaagtggaagggtcattgaggaat
ggtgctgtagggaatgcacaatgcccccactatcgtttcgagcaaaagac
ggctgctggtatggaatggagataaggcccaggaaagaaccagagagcaa
cttagtgaggtcaatggtgacagcggggtcaaccgatcatatggaccact
tctctcttggagtgcttgtgattctactcatggtgcaggagggttgaag
aagagaatgaccacaaagatcatcatgagcacatcaatggcagtgctggt
agtcatgatcttgggaggattttcaatgagtgacctggccaagcttgtga
tcctgatgggtgctactttcgcagaaatgaacactggaggagatgtagct
cacttggcattggtagcggcatttaaagtcagaccagccttgctggtctc
cttcattttcagagccaattggacaccccgtgagagcatgctgctagccc
```

SEQ ID NO: 1. (5' to 3') Gen Bank Accession
Number/Version Number/GI Number AY632535.2
GI:226374362.

tggcttcgtgtcactgcaaactgcgatctctgctcttgaaggtgacttga
tggtcctcattaatggatttgctaggcctggttggcaattcgagcaatgg
ccgtgccacgcactgacaacatcgctctaccaatcaggctgctctaacac
cactagctcgaggcacactgctcgtggcatggagagcgggcctggctact
tgtggagggatcatgctcctctccctgaaagggaaaggtagtgtgaagaa
gaacctgccatttgtcatggccctgggattgacagctgtgagggtagtag
acccttattaatgtggtaggactactgttactcacaaggagtgggaagcgg
agctggcccccagtgaagttctcacagccgttggcctgatatgtgcact
ggccggagggtttgccaaggcagacattgagtggctggacccatggctg
cagtaggcttgctaattgtcagctatgtggtctcgggaaagagtgtggac
atgtacattgaaagagcaggtgacatcacatgggaaaaggacgcggaagt
cactggaaacagtcctcggcttgacgtggcactgtgatgagagtggtgact
tctccttggtagaggaagatggtccacccatgagagagatcatactcaag
gtggtcctgatggccatctgtggcatgaaccaatagctataccttttgc
tgcaggagcgtggtatgtgtatgtgaagactgggaaaaggagtggcgccc
tctgggacgtgcctgctcccaaagaagtgaagaaaggagagaccacagat
ggagtgtacagagtgatgactcgcagactgctaggttcaacacaggttgg
agtgggagtcatgcaaggaggagtcttccacaccatgtggcacgttacaa
aaggagccgcactgaggagcggtgagggaagacttgatcctactgggggg
gatgtcaagcaggacttggtgtcatactgtgggccttggaagttggatgc
agcttgggatggactcagcgaggtacagcttaggccgtacctcccggaga
gagggccagaaacattcagaccctgcctgaaattcaagacaaaggacg
gggacatcggagcagttgctctggactaccctgcagggacctcaggatct
ccgatcctagacaaatgtgaaagtgataggactctatggcaatgggga
gtgatcaagaatggaagctatgttagtgctataacccaggggaaagaggga
ggaggagactccggttgaatgtttcgaaccctcgatgctgaagaagaaga
agctaactgtcttggatctgcatccaggagccggaaaaaccaggagagtt
cttcctgaaatagtccgtgaagccataaaaaagagactccggacagtgat
caggcaccaactagggttgtcgctgctgagatggaggaggccttgagagg
acttccggtgcgttacatgacaacagcagtcaacgtcacccattctggga
cagaaatcgttgatttgatgtgccatgccactttcacttcacgcttacta
caacccatcagagtccctaattacaatctcaacatcatggatgaagccca
cttcacagacccctcaagtatagctgcaagaggatacatatcaacaaggg
agaaatgggcgaggcggctgccattttatgactgccacaccaccaggaa
cccgtgatgcgtttcctgactctaactcaccaatcatggacacagaagtg
gaagtcccagagagagcctggagctcaggcttttgattgggtgacagacca
ttctgggaaaacagtttggttcgttccaagcgtgagaaacggaaatgaaa
tcgcagcctgtctgacaaaggctgaaagcgggtcatacagctcagcagg
aagacttttgagacagaatttcagaaaacaaaaaaatcaagagtgggact
tgtcataacaactgacatctcagagatgggcgccaacttcaaggctgacc
gggtcatagactctaggagatgcctaaaaccagtcatacttgatggtgag
agagtcatcttggctgggcccatgcctgtcacgcatgctagtgctgctca
gaggagaggacgtataggcaggaaccctaacaaaacctgaagtgagtaca
tgtatggaggtgggtgtgcagagactgatgaaggccatgcacactggctt
gaagcaagaatgcttcttgacaacatctacctccaggatggcctcatagc
ctcgctctatcggcctgaggccgataaggtagccgccattgagggagagt
ttaagctgaggacagagcaaaggaagaccttcgtggaactgtgaagaga
ggagaccttcccgtctggctagcctatcaggttgcatctgccggaataac
ttacacagacagaagatggtgctttgatggcacaaccaacaacaccataa
tggaagacagtgtaccagcagaggtttggacaaagtatggagagaagaga
gtgctcaaaccgagatggatggatgctagggtctgttcagaccatgcggc
cctgaagtcgttcaaagaattcgccgctggaaaagaggagcggcttgg
gagtaatggaggccctgggaacactgccaggacacatgacagagaggttt
caggaagccattgacaacctcgccgtgctcatgcgagcagagactggaag
caggcctatatatcaggcagggacccaactgccggagaccctagagacca
ttatgctcttaggtttgctgggaacagtttcactggggatcttcacgtct
tgatgctggaataaggcatcggggaagatgggctttggaatggtaaccctt
ggggccagtgcatggctcatgtggctacggaaattgaaccagccagaatt
gcatgtgtcctcattgagtgatttattactggtggtgctcatacccagc
cagagaagcaaagatctcccaagataaccaatcagatggcaattatcatcatg
gtggcagtgggccttctaggttggataactgcaaacgaacttggatggct
ggaaagaacaaaaaatgacatagctcatctaatgggaaggagaagaag
gagcaaccatgggattctcaatggacattgatctgcggcagcctccgcc
tgggctatctatgccgcattgacaactctcatcaccccagctgtccaaca
tgcggtaaccacttcatacaacaactactccttaatggcgatggccacac
aagctggagtgctgtaggcatgggcaaaggatgccatttatgcatgggg
accttggagtcccgctgctaatgatgggttgctattcacaattaacaccc
ctgactctgatagtagctatcattctgcttgtggcgcactacatgtactt
gatcccaggcctacaagcggcagcagcgcgtgctgcccagaaaaggacag
cagctggcatcatgaagaatcccgagtggatggaatagtggaatactgaca
ttgacacaatgacaatagaccccaggtggagaagaagatgggacaagtg
ttactcatagcagtagcctccagtgctgtgctgctgcggaccgcctg
gggatggggggaggctggagctctgatcacagcagcgacctccaccttgt
gggaaggctctccaaacaaatactggaactcctctacagccacctcactg
tgcaacatcttcagaggaagctatctggcaggagcttcccttatctatac SEQ ID NO: 1. (5' to 3') Gen Bank Accession
Number/Version Number/GI Number AY632535.2
GI:226374362.

agtgacgagaaacgctggcctggttaagagacgtggaggtgggacgggag
agactctgggagagaagtggaaagctcgtctgaatcagatgtcggccctg
gagttctactcttataaaaagtcaggtatcactgaagtgtgtagagagga
ggctcgccgtgccctcaaggatggagtggccacaggaggacatgccgtat
cccggggaagtgcaaagatcagatggttggaggagagagggatatctgcag
ccctatgggaaggttgttgacctcggatgtggcagggggctggagcta
ttatgcgccaccatccgcaaagtgcaggaggtgagaggatacacaaagg
gaggtcccggtcatgaagaacccatgctggtgcaaagctatgggtggaac
atagttcgtctcaagagtggagtggacgtcttccacatggcggctgagcc
gtgtgacactctgctgtgtgatcataggtgagtcatcatctagtcctgaag
tggaagagacacgaacactcagagtgctctctatggtgggggactggctt
gaaaaaagaccaggggcctctctgtataaaggtgctgtgcccatacaccag
cactatgatggaaaccatggagcgactgcaacgtaggcatggggggaggat
tagtcagagtgccattgtgtcgcaactccacacatgagatgtactgggtc
tctgggcaaagagcaacatcatcataaaaagtgtgtccaccacaagtcagct
cctcctgggacgcatggatggccccaggaggccagtgaaatatgaggagg
atgtgaacctcggctcgggtacacgagctgtggcaagctgtgctgaggct
cctaacatgaaaatcatcggcaggcgcattgagagaatccgcaatgaaca
tgcagaaacatgtttcttgatgaaaaccacccatacaggacatgggcct
accatgggagctacgaagccccacgcaaggatcagcgtcttccctcgtg
aacggggttgttagactcctgtcaaagccttgggacgtggtgactggagt
tacaggaatagccgtgactgacaccaccacatacggccaacaaagagtct
tcaaagaaaaagtggacaccagggtgccagatccccaagaaggcactcgc
caggtaatgaacatagtctcttcctggctgtggaaggagctggggaaacg
caagcggccacgcgtctgcaccaaagaagagtttatcaacaaggtgcgca
gcaatgcagcactgggagcaatattgaagaggaaaagaatggaagacg
gctgtggaagctgtgaatgatccaaggttttgggccctagtggataggga
gagaacacccctgagaggagagtgtcacagctgtgtgtacaacatga
tgggaaaaagaaaagaagcaaggagagttcgggaaagcaaaggtagc
cgcgccatctggtacatgtggttgggagccagattcttggagatgaagcc
cttggattcttgaacgaggaccattggatgggaagagaaaactcaggagg
tggagtcgaagggttaggattgcaaagactggatacattctagaagaaa
tgaatcgggcaccaggaggaaagatgtacgcagatgacactgctggctgg
gacacccgcattagtaagtttgatctggagaatgaagctctgattaccaa
ccaaatggagagggcacagaactctggcgttggccgtgattaaataca
catacaaaacaaagtggtgaaggttctcagaccagctgaaggagggaaaa
acagttatggacatcatttcaagacaagaccagagagggagtggacaagt
tgtcactttatgctctcaacacattcaccaacttggtggtgcagcttatcc
ggaacatggaagctgaggaagtgttagagatgcaagacttatggttgttg
aggaagccagagaaagtgaccagatggttgcagagcaatggatgggatag
actcaaacgaatggcggtcagtggagatgactgcgttgtgaagccaatcg
atgataggtttgcacatgccctcaggttcttgaatgacatgggaaaagtt
aggaaagacacacaggagtggaaaaccctcgactggatgggacaattggga
agaagtcccgttctgctcccaccacttcaacaagctgtacctcaaggatg
ggagatccattgtggtccctttgccgccaccaagatgaactgattggccga
gctcgcgtctcaccaggggcaggatggagcatccgggagactgcctgtct
tgcaaaatcatatcgcgcagatgtggcagctcctttatttccacagaaggg
accttcgactgatgctaatgccatttgctcggctgtgccagttgactgg
gtaccaactgggagaaccacctggtcaatccatggaaagggagaatggat
gaccactgaggacatgctcatggtgtggaatagagtgtggattgaggaga
acgaccatatggaggacaagactcctgtaacaaaatggacagacattccc
tatctaggaaaaaggggaggactattggtgtggatcccttataggggcacag
acccccgccaccacttggctgaaaacatcaaagacacagtcaacatggtgc
gcaggatcataggtgatgaagaaagtacatggactatctatcacccaa
gtccgctacttgggtgaggaagggtccacacccggagtgttgtagcacc
aattttagtgagtcaggcctgctagtcagccacagatggggaaagctgtg
cagcctgtaacccccccaggagaagctgggaaaccaagctcatagtcagg
ccgagaacgccatggcacggaagaagccatgctgcctgtgagccctcag
aggacactgagtcaaaaaaccccacgcgcaggaagcgcaggatgggaaaa
gaaggtggcgaccttccccaccctcaatctggggcctgaactggagact
agctgtgaatctccagcaggggactagtggttagaggagaccccccgga
aaacgcaaaacagcatattgacgtgggaaagaccagagactccatgagtt
tccaccacgctggccgccaggcacagatcgccgaacttcggcggccggtg
tggggaaatccatggtttct In certain aspects of the disclosures herein, a combination of at least two oligomers is provided for determining the presence or absence of Zika virus in a sample. Typically, the oligomer combination includes at least two amplification oligomers for amplifying a target sequence of a Zika virus target nucleic acid corresponding to the sequence within SEQ ID NO:1. In such embodiments, at least one amplification oligomer comprises a target-hybridizing sequence in the sense orientation and at least one amplification oligomer comprises a target-hybridizing sequence in the antisense orientation, where the amplification oligomers are each configured to specifically hybridize to a Zika virus target sequence corresponding to a sequence contained within SEQ ID NO:1 and where the target-hybridizing sequences are selected so that the amplification oligomers are situated to hybridize the ends of the target sequence to be amplified. In some variations, the at least two amplification oligomers are configured to specifically hybridize to a target sequence in one or more of the following nucleic acid sequences SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, and reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194. In some variations, the at least two amplification oligomers are configured to specifically hybridize to a target sequence consisting essentially of: SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, or reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194.

TABLE 1

Exemplary Amplification Oligomer Target-hybridizing Sequences for Amplification of Zika virus Target Sequences

| SEQ ID NO: | Sequence (5' to 3') |
| --- | --- |
| 2 | TCYCTTGGAGTGCTTGTGA |
| 3 | TCYCTTGGAGTGCTTGTGATT |
| 4 | TCYCTTGGAGTGCTTGTGATTYT |
| 5 | TCYCTTGGAGTGCTTGTGATTY |
| 6 | YCCYAAYAAACCTGGAGATGAGTA |
| 7 | AAYAAACCTGGAGATG |
| 8 | YAAYAAACCTGGAGATG |
| 9 | TGGCTTGAAGCAAGAATGCT |
| 10 | GCTTGAAGCAAGAAT |
| 11 | AGGACAGCAGCTGGCATCAT |
| 12 | AGGACGGCAGCTGGCATCAT |

TABLE 1-continued

Exemplary Amplification Oligomer Target-hybridizing Sequences for Amplification of Zika virus Target Sequences

| SEQ ID NO: | Sequence (5' to 3') |
| --- | --- |
| 13 | AGGACAGCAGCTGGCATCATG |
| 14 | AGGACGGCAGCTGGCATCATG |
| 15 | AGGACAGCAGCTGGCATCATGA |
| 16 | AGGACGGCAGCTGGCATCATGA |
| 17 | AGGACAGCAGCTGGCATCATGAA |
| 18 | AGGACGGCAGCTGGCATCATGAA |
| 19 | ACGGCAGCTGGCATCATGAA |
| 20 | GACGGCAGCTGGCATCATGAA |
| 21 | ACAGCAGCTGGCATCATGAAGAA |
| 22 | AGGACAGCAGCTGGCATCATGAAGAA |
| 23 | AGAACAGCAGCTGGCATCATGAAGAA |
| 24 | AGRACRGCAGCTGGCATCATGAAGAA |
| 25 | ACRGCAGCTGGCATCAT |
| 26 | RACRGCAGCTGGCATCATGAA |
| 27 | GTTGTGGATGGAATAGTGGT |
| 28 | TCTCTTGGAGTGCTTGTGATTC |
| 29 | TCTCTTGGAGTGCTTGTGATT |
| 30 | TCTCTTGGAGTGCTTGTGA |
| 31 | TCTCTTGGAGTGCTTGTGATTCT |
| 32 | TCCCTTGGAGTGCTTGTGATTCT |
| 33 | TCCCTTGGAGTGCTTGTGATTC |
| 34 | TCCCTTGGAGTGCTTGTGATT |
| 35 | TCCCTTGGAGTGCTTGTGA |
| 36 | AACAAACCTGGAGATGAGTA |
| 37 | CAACAAACCTGGAGATGAGTA |
| 38 | AACAAACCTGGAGATGAGT |
| 39 | CAACAAACCTGGAGATGAGT |
| 40 | CAATAAACCTGGAGATGAGT |
| 41 | CCCAATAAACCTGGAGATGAGT |
| 42 | CCYAAYAAACCTGGAGATGAGTA |
| 43 | CCCAACAAACCTGGAGATGAGTA |
| 44 | YCCYAAYAAACCTGGAGATG |
| 45 | TCCTAACAAACCTGGAGATG |
| 46 | CCCAACAAACCTGGAGATGAGT |
| 47 | CCYAAYAAACCTGGAGATGAG |
| 48 | CCCAACAAACCTGGAGATGAG |
| 49 | AGRACRGCAGCTGGCATCATGAAGA |

TABLE 1-continued

Exemplary Amplification Oligomer Target-hybridizing Sequences for Amplification of Zika virus Target Sequences

| SEQ ID NO: | Sequence (5' to 3') |
|---|---|
| 50 | AGRACRGCAGCTGGCATCATGAAGAA |
| 51 | AGRACRGCAGCTGGCATCATGA |
| 52 | AGRACRGCAGCTGGCATCAT |
| 53 | AGRACRGCAGCTGGCATCATGAA |
| 111 | TRRCTACCAGCACTGCCAT |
| 112 | GTCWATWGTCATTGTGT |
| 113 | GTCATTGTGTCAATGTCAG |
| 114 | GTCTATTGTCATTGTGT |
| 115 | CTGCTATGAGTAACACTTGTCCCATCTT |
| 116 | TAGCTACCAGCACTGCCAT |
| 117 | CTACCAGCACTGCCATTGATGTGC |
| 118 | CTGCYATGAGTARCACYTGYCCCATCTT |
| 119 | GTCWATWGTCATTGTGTCA |
| 120 | YTGYCCCATCTTYTTYT |
| 121 | GTCWATWGTCATTGTGTCAATGTCAG |
| 122 | TRRCTACCAGCACTGCCATTG |
| 123 | GRAGCATTCTTGCTTCAAGCCA |
| 124 | GTCAAGRAGCATTCTTGCTTCA |
| 125 | GTCATTGTGTCAATGTCAGT |
| 126 | TCATTGTGTCAATGTCAGT |
| 127 | GTCTATTGTCATTGTGTCA |
| 128 | ATTGTCATTGTGTCAATGTCAGT |
| 129 | ATTGTCATTGTGTCAATGTCA |
| 130 | ATTGTCATTGTGTCAATGTC |
| 131 | ATTGTCATTGTGTCAATGT |
| 132 | TTGTCCCATCTTCTTCT |
| 133 | GTAACACTTGTCCCATCTT |
| 134 | GTCTATTGTCATTGTGTCAATGTCAG |
| 135 | CTACCAGCACTGCCATTGATGTGCT |
| 136 | CCAGCACTGCCATTGATGTGCT |
| 137 | CTACCAGCACTGCCATTGATGT |
| 138 | TAGCTACCAGCACTGCCATTG |
| 139 | AGCATTCTTGCTTCAAGCCA |
| 140 | GCATTCTTGCTTCAAGCCA |
| 141 | GGAGCATTCTTGCTTCAAGCCA |
| 142 | GTCAAGAAGCATTCTTGCTTCA |
| 143 | TAGAGCGAGGCTATGAGGCCATC |
| 144 | TAGAGCGAGGCTATGAGGCCAT |
| 145 | TAGAGCGAGGCTATGAGGCCA |
| 146 | TAGAGCGAGGCTATGAGG |
| 147 | TAGAGCGAGGCTATGAG |

In certain embodiments, an amplification oligomer as described herein is a promoter-based amplification oligomer comprising a target-hybridizing sequence and further comprising a promoter sequence located 5' to the target-hybridizing sequence wherein the promoter sequence is non-complementary to the Zika virus target nucleic acid. For example, in some embodiments of an oligomer combination as described herein for amplification of a Zika virus target sequence, an amplification oligomer as described above in Table 1 is a promoter-based amplification oligomer, wherein a target-hybridizing sequence further comprises a 5' promoter sequence. In particular embodiments, the promoter sequence is a T7 RNA polymerase promoter sequence such as, for example, a T7 promoter sequence having the sequence shown in SEQ ID NO:179. In specific variations, the amplification oligomer is a has the nucleotide sequence shown in SEQ ID NOs:74-110.

In some embodiments, an oligomer combination as described herein further comprises at least one capture probe oligomer comprising a target-hybridizing sequence substantially corresponding to a sequence contained in the complement of SEQ ID NO:1, wherein the target-hybridizing sequence is covalently attached to a sequence or moiety that binds to an immobilized probe. In specific variations, the target-hybridizing sequence comprises or consists of a sequence substantially corresponding to, or identical to, a sequence selected from SEQ ID NOs:166-178, including complements, DNA equivalents, and DNA/RNA chimerics thereof. In more specific variations, the capture probe oligomer has a sequence selected from SEQ ID NOs:153-165. An oligomer combination may include at least two capture probe oligomers as above. In more specific embodiments, the at least one capture probe oligomer includes providing the at least one capture probe oligomer in a target capture reaction mixture. In one aspect, each of the at least one capture probe oligomers is provided in the target capture reaction mixture at a concentration from about 3 pmoles/reaction to about 6 pmoles/reaction (inclusive of all whole and partial numbers of the range (e.g., 4, 4.75, 5.12, 5.98, 6)). When a plurality of at least one capture probe oligomer is used in a target capture reaction the concentration of each capture probe oligomer may be equal to the concentration of the others or there may be varied concentrations, as described herein.

In certain variations, an oligomer combination as described herein further comprises at least one detection probe oligomer configured to specifically hybridize to a Zika virus target sequence that is amplifiable using the first and second amplification oligomers (e.g., a Zika virus target sequence that is flanked by the target-hybridizing sequences of the first and second amplification oligomers). Particularly suitable detection probe oligomers include, for example, oligomers comprising a target-hybridizing sequence substantially corresponding to, or identical to, a sequence selected from SEQ ID NOs:54-63 & 66-73, including complements, DNA equivalents, and DNA/RNA chimerics thereof. A detection probe oligomer may contain a 2'-methoxy backbone at one or more linkages in the nucleic acid backbone. In some variations, an oligomer combination includes at least two detection probe oligomers. In more specific embodiments, the at least one detection probe oligomer includes providing the at least one detection probe oligomer in an amplicon detection reaction mixture. In one aspect, each of the at least one detection probe oligomers is provided in the detection reaction mixture at about 2.0 E+06 RLU/reaction to about 6.0 E+06 RLU/reaction (inclusive of all whole and partial numbers of the range (e.g., 2.0 E+06, 2.138 E+06, 3.385 E+06 RLU)). When a plurality of at least one detection probe oligomer is used in a detection reaction the concentration of each detection oligomer may be equal to the concentration of the others or there may be varied concentrations, as described herein.

Typically, a detection probe oligomer further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics), a molecular torch (see, e.g., U.S. Pat. Nos. 6,849,412; 6,835,542; 6,534,274; and 6,361,945), and a "molecular beacon" (see, e.g., Tyagi et al., *Nature Biotechnol.* 16:49-53, 1998; U.S. Pat. Nos. 5,118,801 and 5,312,728). In some embodiments, the detections probe oligomers are molecular torch oligomers comprising a target-hybridizing sequence selected from SEQ ID NOs:54-63 & 66-73, including complements, DNA equivalents, and DNA/RNA chimerics thereof.

In another aspect, the present invention provides methods for determining the presence or absence of Zika virus in a sample using an oligomer combination as described herein. Such a method generally includes (1) contacting the sample with at least two oligomers for amplifying a Zika virus nucleic acid target sequence corresponding to a Zika virus target nucleic acid, where the oligomers include at least two amplification oligomers as described herein; (2) performing an in vitro nucleic acid amplification reaction, where any Zika virus target nucleic acid present in the sample is used as a template for generating an amplification product; and (3) detecting the presence or absence of the amplification product, thereby determining the presence or absence of Zika virus in the sample. A detection method in accordance with the present invention typically further includes the step of obtaining the sample to be contacted with the at least two oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed. In certain embodiments, the sample is contacted with at least two amplification oligomers for amplifying a Zika virus nucleic acid target sequence corresponding to a Zika virus target nucleic acid, where the oligomers include at least two amplification oligomers as described above; (2) performing an in vitro nucleic acid amplification reaction, where any Zika virus target nucleic acid present in the sample is used as a template for generating an amplification product and the amplification product sequence substantially corresponds to, or consists essentially of, or is identical to one or more of the following sequences SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, and reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198. In certain embodiments, an amplification product is contacted with a detection probe oligomer that is configured to specifically hybridize to a target sequence in one or more of the following sequences SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198, and reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194 SEQ ID NO:195, SEQ ID NO:196, SEQ ID NO:197, SEQ ID NO:198.

In certain embodiments, the method further includes purifying the Zika virus target nucleic acid from other components in the sample before the contacting step. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains Zika virus nucleic acid and other sample components.

In some embodiments, a Zika virus target nucleic is selectively separated or purified away from other sample components by specifically hybridizing the Zika virus target nucleic acid to a capture probe oligomer. The capture probe oligomer comprises a target-hybridizing sequence configured to specifically hybridize to a Zika virus target sequence so as to form a target-sequence:capture-probe complex that is separated from sample components. Suitable capture probe target-hybridizing sequences include sequences substantially corresponding to, or identical to, a sequence selected from SEQ ID NOs:166-178, including complements, DNA equivalents, and DNA/RNA chimerics thereof. In a preferred variation, the specific target capture binds the Zika virus target:capture-probe complex to an immobilized probe to form a target:capture-probe-immobilized-probe complex that is separated from the sample and, optionally, washed to remove non-target sample components (see, e.g., U.S. Pat. Nos. 6,110,678; 6,280,952; and 6,534,273). In such variations, the capture probe oligomer further comprises a moiety that binds attaches the capture probe, with its bound target sequence, to an immobilized probe attached to a solid support, thereby permitting the hybridized target nucleic acid to be separated from other sample components. In a preferred embodiment, the immobilized probe is a substantially homopolymeric sequence, in a more preferred embodiment, the immobilized probe is a poly-T sequence. By way of example only, in a preferred embodiment, the immobilized probe is a $dT_{14}$ sequence (SEQ ID NO:180). By way of example only, in a preferred embodiment, the capture probe comprises a moiety that is a nucleic acid sequence, preferably SEQ ID NO:181 or SEQ ID NO:182.

In more specific embodiments, the capture probe oligomer includes a tail portion (e.g., a 3' tail) that is a nucleic acid sequence, wherein the nucleic acid sequence is not complementary to the Zika virus target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. By way of example only, in a preferred embodiment the substantially homopolymeric tail is SEQ ID NO181 or 182 and the immobilized probe is SEQ ID NO:180. For example, in specific embodiments of a capture probe comprising a 3' tail, the capture probe has a sequence selected from SEQ ID NOs:153-165.

Target capture typically occurs in a solution phase mixture that contains one or more capture probe oligomers that hybridize specifically to the Zika virus target sequence under hybridizing conditions, usually at a temperature higher than the $T_m$ of the tail-sequence-immobilized-probe-sequence duplex. For embodiments comprising a capture probe tail, the Zika virus-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:Zika virus-target-sequence may be washed one or more times to further remove other sample components. Preferred embodiments use a particulate solid support, such as paramagnetic beads, so that particles with the attached Zika virus-target:capture-probe-immobilized-probe complex may be suspended in a washing solution and retrieved from the washing solution, preferably by using magnetic attraction. To limit the number of handling steps, the Zika virus target nucleic acid may be amplified by simply mixing the Zika virus target sequence in the complex on the support with amplification oligomers and proceeding with amplification steps.

Amplifying a Zika virus target sequence utilizes an in vitro amplification reaction using at least two amplification oligomers that hybridize a target sequence to be amplified. In particular embodiments, the target sequence to be amplified substantially corresponds to all or a portion of SEQ ID NO:1 from about nucleotide position 3340 to about nucleotide position 3862, or from about nucleotide position 5806 to about nucleotide position 6380, or from about nucleotide position 7132 to about nucleotide position 7641, or a combination thereof. In particular embodiments, the target sequence is contained within a sequence from about nucleotide position 3340 to about nucleotide position 3862 of SEQ ID NO:1, or from about nucleotide position 5806 to about nucleotide position 6380 or SEQ ID NO:1, or from about nucleotide position 7132 to about nucleotide position 7641 of SEQ ID NO:1. In particular embodiments, a target sequence is contained within SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, or reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194. In particular embodiments, a target sequence is contained within a sequence consisting essentially of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, the reverse-complement of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, an RNA equivalents of any one of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194, or reverse-complements of an RNA equivalent of SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:194. Particularly suitable amplification oligomer combinations for amplification of these Zika virus regions are described herein. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art and are readily used in accordance with the methods of the present invention.

For example, some amplification methods that use TMA amplification include the following steps. Briefly, the target nucleic acid that contains the sequence to be amplified is provided as single-stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter-based amplification oligomer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, TMA methods utilize a "reverse" TMA reaction. In such variations, the initial or "forward" amplification oligomer is a priming oligonucleotide that hybridizes to the target nucleic acid in the vicinity of the 3'-end of the target sequence. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target sequence, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. In particular, the amplified product will contain a target sequence in or complementary to a sequence in the Zika virus genomic RNA, and a probe will bind directly or indirectly to a sequence contained in the amplified product to indicate the presence of Zika virus nucleic acid in the tested sample.

Preferred embodiments of detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified Zika virus sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein. In some preferred embodiments of the method for detecting Zika virus sequences, such as in certain embodiments using transcription-mediated amplification (TMA), the detection probe is a linear chemiluminescently labeled probe, more preferably, a linear acridinium ester (AE) labeled probe.

Other embodiments using transcription-mediated amplification utilize a promoter-based amplification oligomer, which comprises a first target-hybridizing sequence and, situated 5' to the first region, a second region comprising a promoter sequence for an RNA polymerase, but which is not modified to prevent the initiation of DNA synthesis from its 3'-terminus. In some embodiments, a promoter primer for use in accordance with the detection method comprises a target-hybridizing sequence having a sequence substantially corresponding to, or identical to, a sequence selected from SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, and SEQ ID NO:111.

Assays for detection of the Zika virus nucleic acid may optionally include a non-Zika virus internal control (IC) nucleic acid that is amplified and detected in the same assay reaction mixtures by using amplification and detection oligomers specific for the IC sequence. IC nucleic acid sequences can be RNA template sequences (e.g., and in vitro transcript), synthetic nucleic acid sequences that are spiked into a sample or the IC nucleic acid sequences may be a cellular component. IC nucleic acid sequences that are cellular components can be from exogenous cellular sources or endogenous cellular sources relative to the specimen. In these instances, an internal control nucleic acid is co-amplified with the Zika virus nucleic acid in the amplification reaction mixtures. The internal control amplification product and the Zika virus target sequence amplification product can be detected independently. Two different internal control systems were employed in the procedures described below.

A first arrangement for internal control systems was useful for monitoring the integrity of amplification and detection reactions that employ paired sets of primers and an oligonucleotide probe that hybridized amplification product at a position between the primer binding sites, or the complements thereof. In a simple application, the internal control template nucleic acid can be distinguished from the analyte template nucleic acid at the sequence of bases serving as the probe binding site. These bases may be scrambled, replaced by an unrelated base sequence, or simply contain a sufficient number of point mutations to result in differential probe binding. In this way, nucleic acid products resulting from amplification of analyte nucleic acid can be detected by an analyte-specific probe, and not by an internal control-specific probe. Likewise, amplicons resulting from amplification of internal control nucleic acid can be detected by an internal control-specific probe, and not by an analyte-specific probe. This configuration allows that both analyte and internal control nucleic acid templates may be amplified using identical primers, or primer sets.

In certain embodiments, amplification and detection of a signal from the amplified IC sequence demonstrates that the assay reagents, conditions, and performance of assay steps were properly used in the assay if no signal is obtained for the intended target Zika virus nucleic acid (e.g., samples that test negative for Zika virus). An IC may also be used as an internal calibrator for the assay when a quantitative result is desired, i.e., the signal obtained from the IC amplification and detection is used to set a parameter used in an algorithm for quantitating the amount of Zika virus nucleic acid in a sample based on the signal obtained for an amplified Zika virus target sequence. ICs are also useful for monitoring the integrity of one or more steps in an assay. A preferred embodiment of a synthetic IC nucleic acid sequence is a randomized sequence that has been derived from a naturally occurring source (e.g., an HIV sequence that has been rearranged in a random manner). Another preferred IC nucleic acid sequence may be an RNA transcript isolated from a naturally occurring source or synthesized in vitro, such as by making transcripts from a cloned randomized sequence such that the number of copies of IC included in an assay may be accurately determined. The primers and probe for the IC target sequence are configured and synthesized by using any well-known method provided that the primers and probe function for amplification of the IC target sequence and detection of the amplified IC sequence using substantially the same assay conditions used to amplify and detect the Zika virus target sequence. In preferred embodiments that include a target capture-based purification step, it is preferred that a target capture probe specific for the IC target be included in the assay in the target capture step so that the IC is treated in the assay in a manner analogous to that for the intended Zika virus analyte in all of the assay steps.

Also provided by the subject invention is a reaction mixture for determining the presence or absence of a Zika virus target nucleic acid in a sample. A reaction mixture in accordance with the present invention at least comprises one or more of the following: an oligomer combination as described herein for amplification of a Zika virus target nucleic acid; a capture probe oligomer as described herein for purifying the Zika virus target nucleic acid; and a detection probe oligomer as described herein for determining the presence or absence of a Zika virus amplification product. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a Zika virus target nucleic acid may or may not be present. In addition, for a reaction mixture that includes a detection probe together with an amplification oligomer combination, selection of amplification oligomers and detection probe oligomers for a reaction mixture are linked by a common target sequence (i.e., the reaction mixture will include a probe that binds to a sequence amplifiable by an amplification oligomer combination of the reaction mixture). Reaction mixtures may be aqueous solutions or dried compositions (e.g., lyophilized compositions, spray dried compositions, etc.). Dried compositions may comprise buffers, bulking agents, and stabilizers. In one embodiment, a bulking agent is present in the dried composition, preferably at a concentration of less than about 5% (w/w). The bulking agent may be a disaccharide form of an amorphous sugar. Preferably, the bulking agent is one or more of mannitol, trehalose sucrose, lactose, sorbitol, raffinose, and glucose.

Also provided by the subject invention are kits for practicing the methods as described herein. A kit in accordance with the present invention at least comprises one or more of the following: an amplification oligomer combination as described herein for amplification of a Zika virus target nucleic acid; a capture probe oligomer as described herein for purifying the Zika virus target nucleic acid; a detection probe oligomer as described herein for determining the presence or absence of a Zika virus amplification product; and a probe protection oligomer as described herein for detuning sensitivity of an assay for detecting the Zika virus target nucleic acid. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target sequence of a Zika virus genome, or it may include amplification oligomers for multiple Zika virus target sequences. In addition, for a kit that includes a detection probe together with an amplification oligomer combination, selection of amplification oligomers and detection probe oligomers for a kit are linked by a common target sequence (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

Order of Steps

Target Capture: Nucleic acids underwent specimen processing and target capture prior to amplification essentially according to the procedures disclosed in published International Patent Application No. PCT/US2000/18685, except that templates were captured using Zika virus target capture oligonucleotides having the target capture oligonucleotide sequences given herein. Notably, capture oligonucleotides do not participate in the amplification or detection reactions of the assay. IVT or Virus-containing samples were combined with a target capture reagent to facilitate nucleic acid release and hybridization to capture oligonucleotides disposed on magnetic beads. Incubation was performed to capture Zika virus nucleic acids from the sample. Following the incubation, the magnetic beads and any capture target nucleic acids were transferred to a magnetic wash station for 10-20 min. for a wash step. Captured target nucleic acids were then assayed in an amplification reaction.

Transcription mediated amplification (TMA) reactions were carried out essentially as described in U.S. Pat. No. 5,399,491 (Kacian et al.). Isolated target nucleic acids were combined with primers in amplification reagent heated to 60° C. for 10 minutes and then cooled to 42° C. to facilitate primer annealing. Enzyme reagent was then added to the mixtures and the amplification reactions were carried out, as will be familiar to those having an ordinary level of skill in the art.

Detection: After a one hour incubation at 42° C., the amplification reaction volumes were subjected to hybridization assays employing probes internally labeled with a chemiluminescent compound using techniques familiar to those having an ordinary level of skill in the art, and then used in amounts equivalent to about 2 E+06 to about 6 E+06 RLU for each probe in the hybridization reaction. (See e.g., U.S. Pat. Nos. 5,585,481 and 5,639,604). Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label linked to unhybridized probe, and cooled briefly to room temperature (i.e., 15-30° C.) prior to reading the hybridization signal. Chemiluminescence due to hybridized probe in each sample was assayed using commercially available instrumentation (Gen-Probe Incorporated; San Diego, Calif.) configured for injection of 1 mM nitric acid and 0.1% (v/v) hydrogen peroxide, followed by injection of a solution containing 1 N sodium hydroxide. Results for the chemiluminescent reactions were measured in relative light units (RLU). In this procedure, the signal/noise value corresponded to the chemiluminescent signal (measured in RLU) generated by label associated with specifically hybridized probe divided by a background signal measured in the absence of a target nucleic acid.

TABLE 2

Zika virus Assay Reagents

| Reagent Name | Description |
|---|---|
| Internal Control Reagent | A HEPES buffered solution containing detergent and an RNA transcript. |
| Target Capture Reagent | A HEPES buffered solution containing detergent, capture oligonucleotides and magnetic microparticles. |
| Amplification Reagent | Primers, dNTPs, NTPs and co-factors in TRIS buffered solution containing ProClin 300 as preservative. |
| Enzyme Reagent | MMLV Reverse Transcriptase and T7 RNA Polymerase in HEPES/TRIS buffered solution containing 0.05% sodium azide as preservative. |
| Probe Reagent | Chemiluminescent oligonucleotide probes in succinate buffered solution containing detergent. |
| IC Buffer | A HEPES buffered solution containing detergent. |

The following are non-limiting examples of Zika virus amplification and detection assays.

Example 1

Numerous sets of amplification and detection oligonucleotides were configured to discriminately amplify and detect a zika virus. In this example, the transcription mediated amplification (TMA) reactions were carried out essentially as described by Kacian et al., in U.S. Pat. No. 5,399,491. Amplification reactions were conducted for various combinations of amplification oligonucleotides using about 5 pmoles per reaction of each T7 primer and nonT7 primer in a 75 uL amplification reaction mixture. Amplification products were detected by hybridization protection assay (HPA) using about 2 10^6 reactive light units (RLU) per reaction of each of an acridinium ester (AE)-labeled detection probe.

A first set of amplification and detection oligonucleotides were configured to amplify a target sequence within a zika virus region, wherein the zika virus region corresponds to nucleobases 7132 to 7641 of SEQ ID NO:1 (zika07k region). The amplification oligomers were: for the nonT7 primers, SEQ ID NOs:11-23 & 27; and for the promoter primers, a target-hybridizing sequence from SEQ ID NOs: 113-115, & 125-134 joined at their 3' ends to the promoter primer sequence SEQ ID NO:179 (SEQ ID NOs:74-76, 78-83, 85-87, & 89). The detection probes were esterase-labeled detection probes, SEQ ID NOs:69-73.

A second set of amplification and detection oligonucleotides were configured to amplify a target sequence within a zika virus region, wherein the zika virus region corresponds to nucleobases 3340 to 3862 of SEQ ID NO:1 (zika03k region). The amplification oligomers were: for the nonT7 primers, SEQ ID NOs:28-35; and for the promoter primers, a target-hybridizing sequence from SEQ ID NOs: 116, 117, & 135-138 joined at their 3' ends to the promoter primer sequence SEQ ID NO:179 (SEQ ID NOs:90-92, 94, 95, & 97). The detection probe was an esterase-labeled detection probe, SEQ ID NO:58.

A third set of amplification and detection oligonucleotides were configured to amplify a target sequence within a zika virus region, wherein the zika virus region corresponds to nucleobases 5806 to 6380 of SEQ ID NO:1 (zika06k region). The amplification oligomers were: for the nonT7 primers, SEQ ID NOs:36-41, 43, 45, 46, & 48; and for the promoter primers, a target-hybridizing sequence from SEQ ID NOs:98-106 joined at their 3' ends to the promoter primer sequence SEQ ID NO:179 (SEQ ID NOs:139-147). The detection probes were esterase-labeled detection probes, SEQ ID NOs:59 & 61-63.

In vitro transcripts (IVTs) were made for testing each set of amplification and detection oligonucleotides (SEQ ID NOs:191-193, respectively). The stock concentration of each IVT was determined and then the stock IVTs were each diluted to about 10 copies per mL. Separate target capture reactions were prepared, as described above, and using the following target capture oligonucleotides: for capture of SEQ ID NO:191, SEQ ID NOs:160-163; for capture of SEQ ID NO:192, SEQ ID NOs:153-156; and for capture of SEQ ID NO:193, SEQ ID NOs:157-159. Captured IVT were then combined with an amplification reaction mixture and an isothermal amplification reaction was performed. Amplification oligomer pairs used for these tests were combinations of the non-T7 primers and the promoter primers listed in each of the above amplification and detection oligomer sets. Amplification product was detected using an esterase-labeled detection probe. The detection probes SEQ ID NOs: 69, 58, and 61 were used to detect amplification products generated from the amplification oligomers of set one, set two, and set three, respectively. Detection probe signal (RLU) was read using a luminometer. The RLU data for each reaction was then calculated against a cutoff value to provide a signal to cutoff value (SCO). Tables 3-5, below, report the SCO data for combinations of amplification and detection oligonucleotides from each of sets one to three.

TABLE 4

Set Two Amplification and Detection Oligonucleotide Combinations Results.

| SCO | SEQ ID NO: 90 | SEQ ID NO: 91 | SEQ ID NO: 92 | SEQ ID NO: 94 | SEQ ID NO: 95 | SEQ ID NO: 97 |
|---|---|---|---|---|---|---|
| SEQ ID NO: 28 | 1.9 | 5.0 | 369.4 | 5.6 | 241.7 | 28.3 |
| SEQ ID NO: 29 | 0.6 | 0.5 | 412.6 | 197.6 | 684.8 | 15.9 |
| SEQ ID NO: 30 | 1.3 | 21.4 | 182.9 | 869.5 | 364.0 | 0.9 |
| SEQ ID NO: 31 | 0.1 | 1.0 | 2930.5 | 934.7 | 1449.6 | 1239.5 |
| SEQ ID NO: 32 | 2.1 | 1.9 | 724.4 | 7.9 | 675.3 | 174.9 |
| SEQ ID NO: 33 | 1.0 | 1.4 | 179.9 | 0.2 | 549.4 | 394.4 |
| SEQ ID NO: 34 | 1.4 | 1.5 | 183.8 | 1.1 | 256.4 | 238.5 |
| SEQ ID NO: 35 | 0.6 | 0.1 | 546.8 | 1.1 | 278.9 | 188.5 |

TABLE 5

Set Three Amplification and Detection Oligonucleotide Combinations Results.

| SCO | SEQ ID NO: 102 | SEQ ID NO: 103 | SEQ ID NO: 104 | SEQ ID NO: 105 | SEQ ID NO: 106 |
|---|---|---|---|---|---|
| SEQ ID NO: 36 | 0.5 | 1.6 | 2.6 | 2.4 | 1.2 |
| SEQ ID NO: 37 | 1.7 | 3.7 | 0.8 | 0.2 | 4.0 |
| SEQ ID NO: 38 | 0.1 | 0.2 | 1.5 | 3.2 | 0.9 |
| SEQ ID NO: 39 | 0.7 | 0.5 | 4.2 | 3.0 | 1.7 |
| SEQ ID NO: 40 | 0.3 | 0.1 | 0.9 | 1.1 | 0.4 |
| SEQ ID NO: 41 | 0.5 | 0.6 | 2.2 | 0.1 | 2.0 |
| SEQ ID NO: 43 | 0.8 | 0.1 | 0.6 | 0.2 | 8.1 |
| SEQ ID NO: 45 | 1.4 | 8.6 | 0.2 | 3.0 | 6.0 |
| SEQ ID NO: 46 | 0.2 | 0.7 | 0.1 | 0.3 | 7.8 |
| SEQ ID NO: 48 | 0.3 | 0.2 | 1.8 | 0.3 | 1.6 |

An SCO greater than 1 indicates that the amplification and detection oligonucleotide combination provided a robust detection signal. A more preferable SCO is greater than 10, and an even more preferable SCO is greater than 100. These results indicate that various combinations of oligonucleotides were effective in providing detectable zika virus IVT amplification product above a cutoff value. A number of

TABLE 3

Set One Amplification and Detection Oligonucleotide Combinations Results.

| SEQ ID NO: 27 | SEQ ID NO: 23 | SEQ ID NO: 22 | SEQ ID NO: 21 | SEQ ID NO: 20 | SEQ ID NO: 19 | SEQ ID NO: 18 | SEQ ID NO: 17 | SEQ ID NO: 16 | SEQ ID NO: 15 | SEQ ID NO: 14 | SEQ ID NO: 13 | SEQ ID NO: 12 | SEQ ID NO: 11 | SCO |
|---|---|---|---|---|---|---|---|---|---|---|---|---|---|---|
| 88.8 | 2941.0 | 531.0 | 1687.1 | 1289.2 | 446.1 | 4304.3 | 374.3 | 725.5 | 337.1 | 978.8 | 469.8 | 408.9 | 296.0 | SEQ ID NO: 74 |
| 366.3 | 1000.6 | 349.4 | 3458.6 | 2993.7 | 174.2 | 0.4 | 380.7 | 692.1 | 0.1 | 1929.4 | 195.6 | 4467.9 | 3328.0 | SEQ ID NO: 75 |
| 439.5 | 824.3 | 257.4 | 452.4 | 88.3 | 292.8 | 88.5 | 139.4 | 344.4 | 119.2 | 203.9 | 722.2 | 173.1 | 832.0 | SEQ ID NO: 76 |
| | 1426.6 | 550.8 | 520.0 | 2965.9 | 396.6 | 233.9 | 617.0 | 239.5 | 1002.6 | 206.1 | 0.3 | 302.2 | 536.5 | SEQ ID NO: 78 |
| | 997.5 | 910.2 | 1269.0 | 121.6 | 179.7 | 196.2 | 1082.9 | 1279.5 | 868.0 | 2519.8 | 2.7 | 3452.4 | 714.1 | SEQ ID NO: 79 |
| | 711.9 | 3103.7 | 342.4 | 714.8 | 424.9 | 1262.0 | 714.2 | 1072.9 | 2047.3 | 740.9 | 578.7 | 604.2 | 378.2 | SEQ ID NO: 80 |
| | 8.0 | 11.9 | 12.0 | 1.0 | 4.6 | 2.4 | 1.2 | 5.0 | 1.1 | 0.4 | 0.1 | 0.3 | 3.3 | SEQ ID NO: 81 |
| | 3.9 | 46.7 | 17.6 | 6.9 | 8.3 | 1.2 | 33.8 | 1.0 | 3.7 | 6.7 | 2.2 | 11.2 | 4.7 | SEQ ID NO: 82 |
| | 77.3 | 2.2 | 619.6 | 166.1 | 1150.8 | 632.8 | 46.5 | 181.1 | 53.4 | 70.1 | 86.2 | 660.1 | 5.4 | SEQ ID NO: 83 |
| | 3.7 | 0.4 | 1.7 | 3.5 | 11.8 | 20.1 | 12.5 | 14.8 | 19.9 | 26.2 | 2.0 | 0.2 | 12.4 | SEQ ID NO: 85 |
| | 1.0 | 437.7 | 131.5 | 191.8 | 1694.7 | 370.5 | 15.3 | 387.1 | 387.7 | 192.4 | 785.5 | 424.6 | 3032.3 | SEQ ID NO: 86 |
| | 363.1 | 433.1 | 1192.5 | 714.9 | 447.0 | 296.6 | 1447.8 | 1034.7 | 1307.1 | 597.1 | 2176.1 | 1073.1 | 333.6 | SEQ ID NO: 87 | these amplification and detection oligonucleotide combinations were used in further testing.

Example 2

This example describes multiplex amplification reactions using various primer sets for amplification of two Zika virus target sequences. The Zika virus assay involved three main steps, which take place in a single tube: sample preparation; Zika virus RNA target amplification by Transcription-Mediated Amplification (TMA); and detection of the amplification products (amplicon) by the Hybridization Protection Assay (HPA), as described above. Table 6 below lists the amplification oligonucleotide combinations used in this assay.

TABLE 6

Zika virus Amplification Oligomers

| Condition | Non T7 | T7 |
| --- | --- | --- |
| 1 | SEQ ID NO: 16; SEQ ID NO: 11; & SEQ ID NO: 30 | SEQ ID NO: 78; SEQ ID NO: 80; & SEQ ID NO: 94 |
| 2 | SEQ ID NO: 16; SEQ ID NO: 11; & SEQ ID NO: 35 | SEQ ID NO: 78; SEQ ID NO: 80; & SEQ ID NO: 92 |
| 3 | SEQ ID NO: 16; SEQ ID NO: 11; & SEQ ID NO: 30 | SEQ ID NO: 78; SEQ ID NO: 75; & SEQ ID NO: 94 |
| 4 | SEQ ID NO: 16; SEQ ID NO: 11; & SEQ ID NO: 35 | SEQ ID NO: 78; SEQ ID NO: 75; & SEQ ID NO: 92 |
| 5 | SEQ ID NO: 12; SEQ ID NO: 17; & SEQ ID NO: 30 | SEQ ID NO: 79; SEQ ID NO: 87; SEQ ID NO: 94; & SEQ ID NO: 95 |

Each of the conditions listed in Table 6 were tested in a transcription-mediated amplification (TMA) reaction using (1) Zika virus in vitro transcripts (IVT represented by SEQ ID NOs:191 & 192) each at 10 and 0 copies per mL of internal control buffer (see example 3, below), and (2) a stock virus P6-740 (available from the Center for Disease Control, Atlanta, Ga.) at 0, 1 e-2 and 3 e-3 plaque forming units per mL of BI0052 (Zika virus negative human serum). Transcription mediated amplification (TMA) reactions were carried out essentially as described by Kacian et al., in U.S. Pat. No. 5,399,491. Amplification reactions were conducted for various primer combinations using about 5 pmoles per reaction of each T7 primer and nonT7 primer in a 75 uL amplification reaction mixture. Amplification products were detected by hybridization protection assay (HPA) using about 2 10^6 reactive light units (RLU) per reaction of each of an AE-labeled detection probe having the nucleobase sequences shown in SEQ ID NOs:58 & 69. Each condition was tested in replicates (5 replicates) for each of the IVT dilutions and each of the stock virus dilutions. Signal-to-noise ratios were calculated for each primer pair by dividing the RLU value observed at 10 copies of Zika virus IVT by the background RLU value observed at 0 copies of Zika virus IVT. Total RLU values for the conditions and dilutions are shown in Table 7 below.

TABLE 7

RLU Values of Zika virus T7/nonT7 Amplification Oligo Combinations

| Target/ Dilution | Condition 1 | Condition 2 | Condition 3 | Condition 4 | Condition 5 |
| --- | --- | --- | --- | --- | --- |
| Stock Virus 0 pfu/mL | 963 | 1,178 | 1,081 | 934 | 1,813 |
| | 814 | 955 | 1,328 | 2,386 | 1,473 |
| | 736 | 878 | 1,019 | 963 | 1,484 |
| | 734 | 853 | 1,300 | 918 | 1,402 |
| | 1,415 | 759 | 861 | 826 | 1,429 |
| Stock Virus 1 e-2 pfu/mL | 2,000,485 | 1,870,648 | 994,460 | 1,355,632 | 1,929,586 |
| | 1,941,247 | 1,927,834 | 1,713,798 | 1,818,677 | 1,957,834 |
| | 1,135,584 | 1,864,776 | 1,696,065 | 1,588,766 | 1,993,748 |
| | 1,930,067 | 1,821,843 | 1,786,136 | 1,802,995 | 1,943,361 |
| | 1,814,498 | 1,732,891 | 1,789,571 | 1,729,585 | 1,838,143 |
| Stock Virus 3 e-3 pfu/mL | 1,529,585 | 1,820,238 | 1,597,110 | 1,233,004 | 2,038,343 |
| | 1,048,528 | 1,920,906 | 1,225,351 | 1,851,168 | 2,026,636 |
| | 1,027,851 | 1,875,564 | 1,091,207 | 1,080,080 | 2,043,965 |
| | 1,854,326 | 1,887,128 | 1,870,477 | 1,711,219 | 2,056,585 |
| | 998,130 | 1,905,529 | 981,560 | 1,253,642 | 2,029,214 |
| IVT 0 copies/mL | 926 | 1,095 | 1,163 | 1,139 | 2,577 |
| | 884 | 2,375 | 1,075 | 994 | 1,350 |
| | 806 | 1,014 | 1,112 | 972 | 1,527 |
| | 850 | 1,398 | 1,061 | 926 | 6,352 |
| | 825 | 846 | 1,007 | 1,052 | 1,741 |
| IVT #1 (SEQ ID NO: 191) 10 copies/mL | 984,644 | 958,137 | 963,564 | 441,459 | 2,079,278 |
| | 1,034,198 | 924,170 | 952,185 | 586,993 | 410,577 |
| | 968,755 | 1,812,164 | 927,418 | 1,606,937 | 643,748 |
| | 945,882 | 907,020 | 896,725 | 133,370 | 1,053,188 |
| | 1,504 | 1,648,693 | 899,610 | 835,627 | 1,093,569 |
| IVT #2 (SEQ ID NO: 192) 10 copies/mL | 1,076 | 746,827 | 28,652 | 359,399 | 2,075 |
| | 978 | 943,480 | 666,687 | 609,472 | 994,794 |
| | 1,022 | 30,263 | 1,128 | 947,261 | 972,426 |
| | 1,133 | 961,979 | 1,120 | 1,198 | 971,269 |
| | 1,228 | 1,174 | 1,163 | 849,962 | 966,070 |

Primer pairs that demonstrated an RLU above 100,000 were considered to be successful for amplification of Zika virus target nucleic acid to at least as low as 10 copies of target nucleic acid per mL. These data show that all of the amplification oligonucleotide combinations performed well to amplify as low as 3 e-3 pfu per mL of stock zika virus and as low as 10 copies per mL of IVT #1 (SEQ ID NO:191). Condition 1 failed to amplify and/or detect 10 copies of IVT #2 (SEQ ID NO:192), and condition 3 successfully amplified and/or detected this target in only 1 out of 5 replicates. Conditions 2, 4, & 5 combinations improved the number of successfully amplified and/or detected replicates, but still none showed 5 of 5 successful amplification and detection reactions. Thus, the combinations of just amplification oligomers SEQ ID NOs:30 and 94 performed poorly in this set of tests (conditions 1 and 3), however, adding SEQ ID NO:95 to the combination resulted in a very good performing assay (condition 5). Similarly, the combination of amplification oligonucleotides SEQ ID NOs:35 & 92 performed well in these tests 3 and 4 out of 5 (conditions 2 and 4). Further combinations were tested.

Example 3

This example describes Zika virus amplification and detection assays performed using different oligomer combinations. Sample and oligonucleotide combinations are listed in Tables 8-9 below. Amplification and detection reactions were performed using the Hologic Panther System (Hologic, Inc., Marlborough, Mass.).

TABLE 8

Zika virus-specific Oligonucleotides

| Condition | Non T7 | T7 |
|---|---|---|
| 1 | SEQ ID NO: 12; SEQ ID NO: 17; & SEQ ID NO: 30 | SEQ ID NO: 79; SEQ ID NO: 87; SEQ ID NO: 94; & SEQ ID NO: 95 |
| 2 | SEQ ID NO: 12; SEQ ID NO: 17; & SEQ ID NO: 30 | SEQ ID NO: 87; SEQ ID NO: 89 SEQ ID NO: 95 |
| 3 | SEQ ID NO: 12; SEQ ID NO: 17; & SEQ ID NO: 30 | SEQ ID NO: 79; SEQ ID NO: 89 SEQ ID NO: 94; & SEQ ID NO: 95 |
| 4 | SEQ ID NO: 16; SEQ ID NO: 11; & SEQ ID NO: 35 | SEQ ID NO: 78; SEQ ID NO: 80; & SEQ ID NO: 92 |
| 5 | SEQ ID NO: 16; SEQ ID NO: 11; & SEQ ID NO: 35 | SEQ ID NO: 78; SEQ ID NO: 89; & SEQ ID NO: 92 |
| 6 | SEQ ID NO: 17; SEQ ID NO: 18; SEQ ID NO: 30; & SEQ ID NO: 35 | SEQ ID NO: 74; & SEQ ID NO: 95 |

TABLE 9

Samples Tested

| Sample Identifier | Sample | Description |
|---|---|---|
| A | IVT#1 (SEQ ID NO: 191) | Zika virus In Vitro Transcript (IVT) in IC buffer (Table 2) |
| B | IVT#2 (SEQ ID NO: 192) | Zika virus In Vitro Transcript (IVT) in IC buffer (Table 2) |
| C | Virus P6-740 | Stock virus in BI0052 serum |
| D | Donated blood | Zika virus spiked blood samples diluted in human plasma |
| E | Clinical Samples | Plasma samples from Zika virus positive donors |

A multiplex TMA amplification and detection reaction was performed to determine the analytical sensitivity of a combination of amplification and detection oligomers. This Zika virus assay involved three main steps, which take place in a single tube: sample preparation; Zika virus RNA target amplification by Transcription-Mediated Amplification (TMA); and detection of the amplification products (amplicon) by the Hybridization Protection Assay (HPA), as described above. Tested samples included in vitro transcripts (IVTs) serially diluted in IC buffer, donated human blood spiked with Zika virus RNA and serially diluted in human plasma, cadaveric plasma or cadaveric serum spiked with Zika virus RNA, and clinical samples determined to be positive for Zika virus. Transcription mediated amplification (TMA) reactions were carried out essentially as described by Kacian et al., in U.S. Pat. No. 5,399,491. Amplification reactions were conducted for various combinations of amplification oligonucleotides using about 5 pmoles per reaction of each T7 primer and nonT7 primer in a 75 uL amplification reaction mixture. Amplification products were detected by hybridization protection assay (HPA) using about 2 10^6 reactive light units (RLU) per reaction of each of an acridinium ester (AE)-labeled detection probe. Each amplification oligonucleotide condition was tested in replicates of 5 on each of the sample dilutions. Amplification oligomer combinations are shown in Table 8, above. Detection reactions were performed using SEQ ID NOs:58 & 69 as AE-labeled detection probe oligomers. Tables 10-12 show the results of these reactions. Table 10 shows the RLU values for conditions 1-5 of amplification oligonucleotides. Table 11 and Table 12 show the analytical sensitivity and clinical sensitivity for condition 6 of amplification oligonucleotides. In Table 11 average means average of the reactive samples unless all samples were non-reactive in which case average means average of all non-reactive samples.

TABLE 10

RLU Values of Zika virus T7/nonT7 Amplification Oligo Combinations

| Sample Type Copies/mL | Condition 1 | Condition 2 | Condition 3 | Condition 4 | Condition 5 |
|---|---|---|---|---|---|
| A 10 copies/mL | 48,757 | 757,559 | 762,192 | 9,523 | 781,594 |
| | 375,358 | 8,702 | 418,044 | 63,009 | 267,402 |
| | 1,078 | 776,747 | 798,691 | 354,815 | 807,916 |
| | 758,423 | 800,552 | 758,118 | 27,867 | 791,362 |
| | 746,033 | 304,704 | 763,195 | 308,653 | 761,598 |
| B 10 copies/mL | 906 | 1,930 | 705,223 | 126,982 | 455,773 |
| | 25,945 | 716,734 | 1,219 | 4,289 | 2,859 |
| | 1,002 | 4,320 | 713,626 | 82,863 | 3,843 |
| | 373,889 | 6,343 | 15,160 | 2,831 | 2,106 |
| | 1,246 | 3,818 | 1,186 | 2,303 | 775 |
| C 1 e-2 pfu/mL | 4,491 | 1,287 | 3,077 | 6,013 | 1,459 |
| | 3,012 | 1,102 | 2,844 | 6,269 | 11,925 |
| | 6,754 | 957 | 2,294 | 1,772 | 4,123 |
| | 7,372 | 1,538 | 1,230 | 682 | 1,237 |
| | 5,139 | 6,444 | 676,451 | 1,352 | 783 |
| C 3 e-3 pfu/mL | 4,058 | 10,823 | 17,014 | 4,723 | 1,134 |
| | 987 | 16,253 | 2,328 | 1,416 | 2,029 |
| | 1,527 | 10,552 | 3,119 | 3,592 | 2,732 |
| | 4,586 | 24,009 | 922,487 | 3,562 | 795 |
| | 1,170 | 6,060 | 3,090 | 744 | 9,447 |
| C 0 pfu/mL | 944 | 1,074 | 1,046 | 4,074 | 5,482 |
| | 11,680 | 880 | 3,649 | 4,061 | 2,660 |
| | 6,761 | 2,365 | 3,059 | 18,396 | 3,426 |
| | 7,895 | 1,186 | 9,854 | 2,312 | 1,513 |
| | 3,503 | 5,757 | 12,162 | 16,504 | 11,853 |

TABLE 11

Analytical Sensitivity of a Multiplexed Amplification and Detection Reaction

| Sample Type(s) Copies/mL | #Reactive/ Tested | % Reactive (95% CI) | SCO Average | % cv |
|---|---|---|---|---|
| A&B 90 Copies/mL | 20/20 | 100 (84-100) | 33.5 | 4.3% |
| A&B 30 Copies/mL | 72/72 | 100 (95-100) | 33.2 | 4.7% |
| A&B 10 Copies/mL | 66/72 | 92 (83-96) | 32.0 | 13.6% |
| A&B 3 Copies/mL | 39/72 | 54 (43-65) | 28.7 | 23.3% |
| A&B 1 Copy/mL | 16/72 | 22 (14-33) | 27.7 | 26.4% |
| A&B 0.3 Copies/mL | 2/72 | 3 (1-10) | 24.5 | 50.7% |
| D 90 Copies/mL | 20/20 | 100 (84-100) | 32.5 | 3.3% |
| D 30 Copies/mL | 72/72 | 100 (95-100) | 32.6 | 4.1% |
| D 10 Copies/mL | 72/72 | 100 (95-100) | 31.5 | 9.7% |
| D 3 Copies/mL | 62/72 | 86 (76-92) | 25.8 | 29.3% |
| D 1 Copy/mL | 27/72 | 38 (27-49) | 24.1 | 37.1% |
| D 0.3 Copies/mL | 14/72 | 19 (12-30) | 17.7 | 32.8% |

TABLE 11-continued

Analytical Sensitivity of a Multiplexed
Amplification and Detection Reaction

| Sample Type(s) Copies/mL | #Reactive/ Tested | % Reactive (95% CI) | SCO Average | % cv |
|---|---|---|---|---|
| D 0.1 Copies/mL | 1/72 | 1 (0-8) | 15.7 | N/A |
| No Template 0 Copies/mL | 0/144 | 0 (0-5) | 0.0 | N/A |

TABLE 12

Clinical Sensitivity of a Multiplexed Amplification and Detection Reaction

| Sample Origin Country | Neat | | | Pooled | | |
|---|---|---|---|---|---|---|
| | # Reactive / Tested | % Reactive | SCO | # Reactive / Tested | % Reactive | SCO |
| Colombia | 1/1 | 100% | 30.5 | 4/4 | 100% | 30.7 |
| Colombia | 1/1 | 100% | 31.3 | 4/4 | 100% | 31.8 |
| Colombia | 1/1 | 100% | 31.3 | 4/4 | 100% | 31.6 |
| Colombia | 1/1 | 100% | 32.5 | 4/4 | 100% | 19.7 |
| Colombia | 1/1 | 100% | 32.8 | 4/4 | 100% | 28.1 |
| Colombia | 1/1 | 100% | 32.5 | 4/4 | 100% | 31.4 |
| Colombia | 1/1 | 100% | 31.2 | 4/4 | 100% | 30.8 |
| Colombia | 1/1 | 100% | 29.8 | 4/4 | 100% | 31.1 |
| Colombia | 1/1 | 100% | 32.1 | 3/4 | 75% | 25.9 |
| Dominican Republic | 1/1 | 100% | 30.9 | 4/4 | 100% | 31.5 |
| Dominican Republic | 1/1 | 100% | 31.8 | 4/4 | 100% | 27.0 |
| Dominican Republic | 1/1 | 100% | 32.3 | 4/4 | 100% | 31.7 |
| Dominican Republic | 1/1 | 100% | 32.1 | 4/4 | 100% | 30.5 |
| Dominican Republic | 1/1 | 100% | 30.6 | 4/4 | 100% | 31.2 |
| Dominican Republic | 1/1 | 100% | 31.8 | 1/4 | 25% | 16.2 |
| Dominican Republic | 1/1 | 100% | 33.4 | 4/4 | 100% | 27.5 |
| Dominican Republic | 1/1 | 100% | 30.3 | 4/4 | 100% | 31.3 |
| Dominican Republic | 1/1 | 100% | 31.0 | 4/4 | 100% | 22.8 |
| Dominican Republic | 1/1 | 100% | 32.1 | 4/4 | 100% | 30.9 |
| Dominican Republic | 1/1 | 100% | 31.7 | 4/4 | 100% | 31.9 |
| Dominican Republic | 1/1 | 100% | 32.0 | 4/4 | 100% | 32.5 |
| Dominican Republic | 1/1 | 100% | 29.6 | 4/4 | 100% | 31.6 |
| Dominican Republic | 1/1 | 100% | 29.8 | 4/4 | 100% | 31.6 |
| Colombia | 1/1 | 100% | 30.3 | 4/4 | 100% | 31.7 |
| Colombia | 1/1 | 100% | 31.7 | 4/4 | 100% | 32.2 |
| Colombia | 1/1 | 100% | 29.6 | 4/4 | 100% | 30.2 |

These data show that conditions 3 and 5 performed well at amplifying as low as 10 copies per mL of IVT #1 (SEQ ID NO:191). Conditions 1, 2 and 4 amplified 2 to 3 of 5 replicates containing 10 copies per mL of SEQ ID NO;191. Conditions 1, 2, 3 & 5 amplifies 1 to 2 out of 5 replicates containing 10 copies per mL of IVT #2 (SEQ ID NO:192). In this experiment, none of the conditions performed well at amplifying target nucleic acid from various pfu/mL of P6-740 virus, with only conditions 3 amplifying 1 of 5 replicates at each concentration. Probit analysis of the multiplexed assay showed detection probabilities in copies/mL (95% fiducial limits) for the IVTA&B and spiked blood donor samples to be (i) 204 (2.0-2.9) for 50% probability and 13.4 (9.9-20.3) for 95% probability, and (ii) 1.0 (0.8-1.2) for 50% probability, and 5.9 (4.3-8.9) for 95% probability. Clinical samples showed 100% (95% CI 87-100%) sensitivity (26 of 26) in neat samples and 96% (95% CI 91-98%) sensitivity (100 of 104) in 1:16 pooled samples. Thus, these amplification oligonucleotide combinations demonstrate very sensitive detection of Zika virus RNA down to about 6 to about 13 copies of Zika virus nucleic acid per mL for an assay specificity of greater than 99.90%.

Sequences

TABLE 13

Exemplary Oligomer Sequences, Reference Sequences, and Regions

| SEQ ID NO: | SEQUENCE (5' TO 3') |
|---|---|
| 1 | AY632535.2 GI:226374362[1] |
| 2 | TCYCTTGGAGTGCTTGTGA |
| 3 | TCYCTTGGAGTGCTTGTGATT |
| 4 | TCYCTTGGAGTGCTTGTGATTYT |
| 5 | TCYCTTGGAGTGCTTGTGATTY |
| 6 | YCCYAAYAAACCTGGAGATGAGTA |
| 7 | AAYAAACCTGGAGATG |
| 8 | YAAYAAACCTGGAGATG |
| 9 | TGGCTTGAAGCAAGAATGCT |

TABLE 13-continued

Exemplary Oligomer Sequences, Reference Sequences, and Regions

| SEQ ID NO: | SEQUENCE (5' TO 3') |
|---|---|
| 10 | GCTTGAAGCAAGAAT |
| 11 | AGGACAGCAGCTGGCATCAT |
| 12 | AGGACGGCAGCTGGCATCAT |
| 13 | AGGACAGCAGCTGGCATCATG |
| 14 | AGGACGGCAGCTGGCATCATG |
| 15 | AGGACAGCAGCTGGCATCATGA |
| 16 | AGGACGGCAGCTGGCATCATGA |
| 17 | AGGACAGCAGCTGGCATCATGAA |
| 18 | AGGACGGCAGCTGGCATCATGAA |
| 19 | ACGGCAGCTGGCATCATGAA |
| 20 | GACGGCAGCTGGCATCATGAA |
| 21 | ACAGCAGCTGGCATCATGAAGAA |
| 22 | AGGACAGCAGCTGGCATCATGAAGAA |
| 23 | AGAACAGCAGCTGGCATCATGAAGAA |
| 24 | AGRACRGCAGCTGGCATCATGAAGAA |
| 25 | ACRGCAGCTGGCATCAT |
| 26 | RACRGCAGCTGGCATCATGAA |
| 27 | GTTGTGGATGGAATAGTGGT |
| 28 | TCTCTTGGAGTGCTTGTGATTC |
| 29 | TCTCTTGGAGTGCTTGTGATT |
| 30 | TCTCTTGGAGTGCTTGTGA |
| 31 | TCTCTTGGAGTGCTTGTGATTCT |
| 32 | TCCCTTGGAGTGCTTGTGATTCT |
| 33 | TCCCTTGGAGTGCTTGTGATTC |
| 34 | TCCCTTGGAGTGCTTGTGATT |
| 35 | TCCCTTGGAGTGCTTGTGA |
| 36 | AACAAACCTGGAGATGAGTA |
| 37 | CAACAAACCTGGAGATGAGTA |
| 38 | AACAAACCTGGAGATGAGT |
| 39 | CAACAAACCTGGAGATGAGT |
| 40 | CAATAAACCTGGAGATGAGT |
| 41 | CCCAATAAACCTGGAGATGAGT |
| 42 | CCYAAYAAACCTGGAGATGAGTA |
| 43 | CCCAACAAACCTGGAGATGAGTA |
| 44 | YCCYAAYAAACCTGGAGATG |
| 45 | TCCTAACAAACCTGGAGATG |
| 46 | CCCAACAAACCTGGAGATGAGT |

TABLE 13-continued

Exemplary Oligomer Sequences, Reference Sequences, and Regions

| SEQ ID NO: | SEQUENCE (5' TO 3') |
|---|---|
| 47 | CCYAAYAAACCTGGAGATGAG |
| 48 | CCCAACAAACCTGGAGATGAG |
| 49 | AGRACRGCAGCTGGCATCATGAAGA |
| 50 | AGRACRGCAGCTGGCATCATGAAGAA |
| 51 | AGRACRGCAGCTGGCATCATGA |
| 52 | AGRACRGCAGCTGGCATCAT |
| 53 | AGRACRGCAGCTGGCATCATGAA |
| 54 | TRAAGAAGAGAATGACCAC |
| 55 | URAAGAAGAGAAUGACCAC |
| 56 | GTTGTGGAKGGAATAGTGGT |
| 57 | GUUGUGGAKGGAAUAGUGGT |
| 58 | UGAAGAAGAGAAUGACCAC |
| 59 | UGUAUGGAGGUGGGUGUGC |
| 60 | CUGGCUUGAAGCAAGAAUGCT |
| 61 | UGGCUUGAAGCAAGAAUGCT |
| 62 | UGGCUUGAAGCAAGAAT |
| 63 | GCUUGAAGCAAGAAUGCT |
| 64 | CATTGACACAATG |
| 65 | ACTGACATTGACACAATGACWAT |
| 66 | ACUGACAUUGACACAAUGACWAT |
| 67 | GACAUUGACACAAUGACWAT |
| 68 | CAUUGACACAAUGACWAT |
| 69 | GUUGUGGAUGGAAUAGUGGT |
| 70 | ACUGACAUUGACACAAUGACAAT |
| 71 | ACUGACAUUGACACAAUG |
| 72 | GACAUUGACACAAUGACAAT |
| 73 | CAUUGACACAAUGACAAT |
| 74 | AATTTAATACGACTCACTATAGGGAGAGTCATTGTGTCAATGTCAG |
| 75 | AATTTAATACGACTCACTATAGGGAGAGTCATTGTGTCAATGTCAGT |
| 76 | AATTTAATACGACTCACTATAGGGAGATCATTGTGTCAATGTCAGT |
| 77 | AATTTAATACGACTCACTATAGGGAGAGTCWATWGTCATTGTGTCA |
| 78 | AATTTAATACGACTCACTATAGGGAGAGTCTATTGTCATTGTGTCA |
| 79 | AATTTAATACGACTCACTATAGGGAGAGTCTATTGTCATTGTGT |
| 80 | AATTTAATACGACTCACTATAGGGAGAATTGTCATTGTGTCAATGTCAGT |
| 81 | AATTTAATACGACTCACTATAGGGAGAATTGTCATTGTGTCAATGTCA |
| 82 | AATTTAATACGACTCACTATAGGGAGAATTGTCATTGTGTCAATGTC |
| 83 | AATTTAATACGACTCACTATAGGGAGAATTGTCATTGTGTCAATGT |

TABLE 13-continued

Exemplary Oligomer Sequences, Reference Sequences, and Regions

| SEQ ID NO: | SEQUENCE (5' TO 3') |
|---|---|
| 84 | AATTTAATACGACTCACTATAGGGAGAYTGYCCCATCTTYTTYT |
| 85 | AATTTAATACGACTCACTATAGGGAGATTGTCCCATCTTCTTCT |
| 86 | AATTTAATACGACTCACTATAGGGAGAGTAACACTTGTCCCATCTT |
| 87 | AATTTAATACGACTCACTATAGGGAGACTGCTATGAGTAACACTTGTCCCATCTT |
| 88 | AATTTAATACGACTCACTATAGGGAGAGTCWATWGTCATTGTGTCAATGTCAG |
| 89 | AATTTAATACGACTCACTATAGGGAGAGTCTATTGTCATTGTGTCAATGTCAG |
| 90 | AATTTAATACGACTCACTATAGGGAGACTACCAGCACTGCCATTGATGTGCT |
| 91 | AATTTAATACGACTCACTATAGGGAGACCAGCACTGCCATTGATGTGCT |
| 92 | AATTTAATACGACTCACTATAGGGAGACTACCAGCACTGCCATTGATGT |
| 93 | AATTTAATACGACTCACTATAGGGAGATRRCTACCAGCACTGCCAT |
| 94 | AATTTAATACGACTCACTATAGGGAGATAGCTACCAGCACTGCCAT |
| 95 | AATTTAATACGACTCACTATAGGGAGACTACCAGCACTGCCATTGATGTGC |
| 96 | AATTTAATACGACTCACTATAGGGAGATRRCTACCAGCACTGCCATTG |
| 97 | AATTTAATACGACTCACTATAGGGAGATAGCTACCAGCACTGCCATTG |
| 98 | AATTTAATACGACTCACTATAGGGAGAAGCATTCTTGCTTCAAGCCA |
| 99 | AATTTAATACGACTCACTATAGGGAGAGCATTCTTGCTTCAAGCCA |
| 100 | AATTTAATACGACTCACTATAGGGAGAGGAGCATTCTTGCTTCAAGCCA |
| 101 | AATTTAATACGACTCACTATAGGGAGAGTCAAGAAGCATTCTTGCTTCA |
| 102 | AATTTAATACGACTCACTATAGGGAGATAGAGCGAGGCTATGAGGCCATC |
| 103 | AATTTAATACGACTCACTATAGGGAGATAGAGCGAGGCTATGAGGCCAT |
| 104 | AATTTAATACGACTCACTATAGGGAGATAGAGCGAGGCTATGAGGCCA |
| 105 | AATTTAATACGACTCACTATAGGGAGATAGAGCGAGGCTATGAGG |
| 106 | AATTTAATACGACTCACTATAGGGAGATAGAGCGAGGCTATGAG |
| 107 | AATTTAATACGACTCACTATAGGGAGAGTCWATWGTCATTGTGT |
| 108 | AATTTAATACGACTCACTATAGGGAGACTGCYATGAGTARCACYTGYCCCATCTT |
| 109 | AATTTAATACGACTCACTATAGGGAGAGRAGCATTCTTGCTTCAAGCCA |
| 110 | AATTTAATACGACTCACTATAGGGAGAGTCAAGRAGCATTCTTGCTTCA |
| 111 | TRRCTACCAGCACTGCCAT |
| 112 | GTCWATWGTCATTGTGT |
| 113 | GTCATTGTGTCAATGTCAG |
| 114 | GTCTATTGTCATTGTGT |
| 115 | CTGCTATGAGTAACACTTGTCCCATCTT |
| 116 | TAGCTACCAGCACTGCCAT |
| 117 | CTACCAGCACTGCCATTGATGTGC |
| 118 | CTGCYATGAGTARCACYTGYCCCATCTT |
| 119 | GTCWATWGTCATTGTGTCA |
| 120 | YTGYCCCATCTTYTTYT |

TABLE 13-continued

Exemplary Oligomer Sequences, Reference Sequences, and Regions

| SEQ ID NO: | SEQUENCE (5' TO 3') |
|---|---|
| 121 | GTCWATWGTCATTGTGTCAATGTCAG |
| 122 | TRRCTACCAGCACTGCCATTG |
| 123 | GRAGCATTCTTGCTTCAAGCCA |
| 124 | GTCAAGRAGCATTCTTGCTTCA |
| 125 | GTCATTGTGTCAATGTCAGT |
| 126 | TCATTGTGTCAATGTCAGT |
| 127 | GTCTATTGTCATTGTGTCA |
| 128 | ATTGTCATTGTGTCAATGTCAGT |
| 129 | ATTGTCATTGTGTCAATGTCA |
| 130 | ATTGTCATTGTGTCAATGTC |
| 131 | ATTGTCATTGTGTCAATGT |
| 132 | TTGTCCCATCTTCTTCT |
| 133 | GTAACACTTGTCCCATCTT |
| 134 | GTCTATTGTCATTGTGTCAATGTCAG |
| 135 | CTACCAGCACTGCCATTGATGTGCT |
| 136 | CCAGCACTGCCATTGATGTGCT |
| 137 | CTACCAGCACTGCCATTGATGT |
| 138 | TAGCTACCAGCACTGCCATTG |
| 139 | AGCATTCTTGCTTCAAGCCA |
| 140 | GCATTCTTGCTTCAAGCCA |
| 141 | GGAGCATTCTTGCTTCAAGCCA |
| 142 | GTCAAGAAGCATTCTTGCTTCA |
| 143 | TAGAGCGAGGCTATGAGGCCATC |
| 144 | TAGAGCGAGGCTATGAGGCCAT |
| 145 | TAGAGCGAGGCTATGAGGCCA |
| 146 | TAGAGCGAGGCTATGAGG |
| 147 | TAGAGCGAGGCTATGAG |
| 148 | CCAGCACTGCCAT |
| 149 | CTACCAGCACTGCCAT |
| 150 | GTCWATWGTCATTGTGTCAATGTCAGT |
| 151 | CTGCYATGAGTARCACYTGYCCCATCTTYTTYTCCACYTGGGGGTCWATWGTCATTGTGTCAATGTCAGT |
| 152 | TRRCTACCAGCACTGCCATTGATGTGC |
| 153 | GCCUUAUCUCCAUUCCAUACCAUUAAAAAAAAAAAAAAAAAAAAAAAAAAAA |
| 154 | GGCCUUAUCUCCAUUCCAUACCAUUUAAAAAAAAAAAAAAAAAAAAAAAAAAAA |
| 155 | ACAUCUCCUCCAGUGUUCAUUUCUUUAAAAAAAAAAAAAAAAAAAAAAAAAAAA |
| 156 | AGCCACAUCUCCUCCAGUGUUCAUUUAAAAAAAAAAAAAAAAAAAAAAAAAAAA |

TABLE 13-continued

Exemplary Oligomer Sequences, Reference Sequences, and Regions

| SEQ ID NO: | SEQUENCE (5' TO 3') |
|---|---|
| 157 | AUGACUCUCUCACCAUCAAGUAUGACUUAAAAAAAAAAAAAAAAAAAAAAAAAAAA |
| 158 | AGCUUGAACUCUCCCUCAAUGGCGGUUUAAAAAAAAAAAAAAAAAAAAAAAAAAAA |
| 159 | CUGUCUUCCAUUAUGGUGUUGUUGGUUUAAAAAAAAAAAAAAAAAAAAAAAAAAAA |
| 160 | CCUGGGAUCAAGUACAUGUAGUGUUUAAAAAAAAAAAAAAAAAAAAAAAAAAAA |
| 161 | CCUGGGAUCAAGUACAUGUAGUUUAAAAAAAAAAAAAAAAAAAAAAAAAAAA |
| 162 | GAGGAGUUCCAGUAUUUGUUUGGUUUAAAAAAAAAAAAAAAAAAAAAAAAAAAA |
| 163 | GAGGAGUUCCAGUAUUUGUUUAAAAAAAAAAAAAAAAAAAAAAAAAAAA |
| 164 | CGGCCAAUCAGUUCAUCUUGGUGGCGGCUUUAAAAAAAAAAAAAAAAAAAAAAAAAAAAAAAAA |
| 165 | CAGCUAGUCUCCAGUUCAGGCCCUUUAAAAAAAAAAAAAAAAAAAAAAAAAAAA |
| 166 | CAGCUAGUCUCCAGUUCAGGCCC |
| 167 | CGGCCAAUCAGUUCAUCUUGGUGGCGGC |
| 168 | GGCCUUAUCUCCAUUCCAUACCA |
| 169 | ACAUCUCCUCCAGUGUUCAUUUC |
| 170 | CCUGGGAUCAAGUACAUGUAG |
| 171 | GCCUUAUCUCCAUUCCAUACCA |
| 172 | AGCCACAUCUCCUCCAGUGUUCA |
| 173 | AUGACUCUCUCACCAUCAAGUAUGACUU |
| 174 | AGCUUGAACUCUCCCUCAAUGGCGG |
| 175 | CUGUCUUCCAUUAUGGUGUUGUUGG |
| 176 | CCUGGGAUCAAGUACAUGUAGUG |
| 177 | GAGGAGUUCCAGUAUUUGUUUGG |
| 178 | GAGGAGUUCCAGUAUUUGUUU |
| 179 | AATTTAATACGACTCACTATAGGGAGA |
| 180 | TTTTTTTTTTTTTT |
| 181 | TTTAAAAAAAAAAAAAAAAAAAAAAAAAAAA |
| 182 | AAAAAAAAAAAAAAAAAAAAAAAAAAAA |
| 183 | AGGACAGCAGCTGGCATCATGAAGAATCCCGTTGTGGATGGAATAGTGGTAACTGACATTGACACAATGACAATAGACCCCCAGGTGGAGAAGAAGATGGGACAAGTGTTACTCATAGCAG |
| 184 | AGGACAGCAGCTGGCATCATGAAGAATCCCGTTGTGGATGGAATAGTGGTAACTGACATTGACACAATGACAATAGAC |
| 185 | CCCTAACAAACCTGGAGATGAGTACATGTATGGAGGTGGGTGTGCAGAGACTGATGAAGGCCATGCACACTGGCTTGAAGCAAGAATGCTTCTTGACAACATCTACCTCCAGGATGGCCTCATAGCCTCGCTCTA |
| 186 | TCTCTTGGAGTGCTTGTGATTCTACTCATGGTGCAGGAGGGGTTGAAGAAGAGAATGACCACAAAGATCATCATGAGCACATCAATGGCAGTGCTGGTAGTCA |
| 187 | TCYCTTGGAGTGCTTGTGATTYTRCTCATGGTGCAGGARGGGYTRAAGAAGAGAATGACCACAAAGATCATCATRAGCACATCAATGGCAGTGCTGGTAGYYA |

TABLE 13-continued

Exemplary Oligomer Sequences, Reference Sequences, and Regions

| SEQ ID NO: | SEQUENCE (5' TO 3') |
|---|---|
| 188 | YCCYAAYAAACCTGGAGATGAGTAYMTGTATGGAGGTGGGTGYGCAGAGACTGAYGA AGRYCAYGCACACTGGCTTGAAGCAAGAATGCTYCTTGACAAYATYTACCTCCARGAT GGCCTCATAGCYTCGCTCTA |
| 189 | AGRACRGCAGCTGGCATCATGAAGAAYCCYGTTGTGGAKGGAATAGTGGTRACTGACA TTGACACAATGACWATWGAC |
| 190 | AGRACRGCAGCTGGCATCATGAAGAAYCCYGTTGTGGAKGGAATAGTGGTRACTGACA TTGACACAATGACWATWGACCCCCARGTGGARAARAAGATGGGRCARGTGYTACTCA TRGCAG |
| 191 | GGGCGAAUUGGGUACCGGGCCCCCCCUCGAGGUCGACGGUAUCGAUAAGCUUGCUGC UAAUGAUGGGUUGCUAUUCACAAUUAACACCCCUGACUCUGAUAGUAGCUAUCAUU CUGCUUGUGGCGCACUACAUGUACUUGAUCCCAGGCCUACAAGCGGCAGCAGCGCGU GCUGCCCAGAAAAGGACAGCAGCUGGCAUCAUGAAGAAUCCCGUUGUGGAUGGAAU AGUGGUAACUGACAUUGACACAAUGACAAUGACCCCCAGGUGGAGAAGAAGAUGG GACAAGUGUUACUCAUAGCAGUAGCCAUCUCCAGUGCUGUGCUGCUGCGGACCGCCU GGGGAUGGGGGAGGCUGGAGCUCUGAUCACAGCAGCGACCUCCACCUUGUGGGAA GGCUCUCCAAACAAAUACUGGAACUCCUCUACAGCCACCUCACUGUGCAACAUCUUC AGAGGAAGCUAUCUGGCAGGAGCUUCCCUUAUCUAUACAGUGACGAGAAACGCUGA AUU |
| 192 | GGGCGAAUUGGGUACCGGGCCCCCCCUCGAGGUCGACGGUAUCGAUAAGCUUGAUA UCGAAUUCCUGCAGCCCGGGGAUCCCACUAUCGUUUCGAGCAAAAGACGGCUGCUG GUAUGGAAUGGAGAUAAGGCCCAGGAAAGAACCAGAGAGCAACUUAGUGAGGUCAA UGGUGACAGCGGGGUCAACCGAUCAUAUGGACCACUUCUCUCUUGGAGUGCUUGUG AUUCUACUCAUGGUGCAGGAGGGGUUGAAGAAGAGAAUGACCACAAAGAUCAUCAU GAGCACAUCAAUGGCAGUGCUGGUAGUCAUGAUCUUGGGAGGAUUUUCAAUGAGUG ACCUGGCCAAGCUUGUGAUCCUGAUGGGUGCUACUUUCGCAGAAAUGAACACUGGA GGAGAUGUAGCUCACUUGGCAUUGGUAGCGGCAUUUAAAGUCAGACCAGCCUUGCU GGUCUCCUUCAUUUUCAGAGCCAAUUGGACACCCCGUGAGAGCAUGCUGCUAGCGGC C |
| 193 | GGGCGAAUUGGGUACCGGGCCCCCCCUCGAGGUCGACGGUAUCGAUAAGCUUGUCAU AGACUCUAGGAGAUGCCUAAAACCAGUCAUACUUGAUGGUGAGAGAGUCAUCUUGG CUGGGCCCAUGCCUGUCACGCAUGCUAGUGCUGCUCAGAGGAGAGGACGUAUAGGC AGGAACCCUAACAAACCUGGAGAUGAGUACAUGUAUGGAGGUGGGUGUGCAGAGAC UGAUGAAGGCCAUGCACACUGGCUUGAAGCAAGAAUGCUUCUUGACAACAUCUACC UCCAGGAUGGCCUCAUAGCCUCGCUCUAUCGGCCUGAGGCCGAUAAGGUAGCCGCCA UUGAGGGAGAGUUUAAGCUGAGGACAGAGCAAAGGAAGACCUUCGUGGAACUCAUG AAGAGAGGAGACCUUCCCGUCUGGCUAGCCUAUCAGGUUGCAUCUGCCGGAAUAAC UUACACAGACAGAAGAUGGUGCUUUGAUGGCACAACCAACAACACCAUAAUGGAAG ACAGCGUACCAGCAGAGGUGUGGACAAAGUAUGGAGAGAAGAGAGUGCUCAAACCG AAUU |
| 194 | AGRACRGCAGCTGGCATCATGAAGAAYCCYGTTGTGGAKGGAATAGTGGTRACTGACA TTGACACAATGAC |
| 195 | YMTGTATGGAGGTGGGTGYGCAGAGACTGAYGAAGRYCAYGCACACTGGCTTGAAGC AAGAATGCTYCTTGACAAYATYTACCTCCAR |
| 196 | RCTCATGGTGCAGGARGGGYTRAAGAAGAGAATGACCACAAAGATCATCATR |
| 197 | YCCYGTTGTGGAKGGAATAGTGGTR |
| 198 | YCCYGTTGTGGAKGGAATAGTGGTRACTGACATTGACACAATGACWATWGACCCCCA RGTGGA |

[1] SEQ ID NO: 1 is referenced to its GenBank Accession Number and Version.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A combination of at least two amplification oligomers for amplifying a Zika virus nucleic acid in a sample, the oligomer combination comprising:
at least two amplification oligomers configured to amplify a target sequence corresponding to a Zika virus target nucleic acid, wherein the target sequence consists of SEQ ID NO:187, the RNA equivalent of SEQ ID NO:187, or the DNA or RNA complement of SEQ ID NO:187, wherein the first amplification oligomer and the second amplification oligomer are configured to hybridize to opposite ends of the target sequence to generate amplification products;

wherein the first amplification oligomer comprises a target-hybridizing sequence that is from 19 to 23 contiguous nucleobases in length, and wherein the second amplification oligomer comprises a target-hybridizing sequence selected from the group consisting of SEQ ID NO:117 and SEQ ID NO:137, wherein the second amplification oligomer target -hybridizing sequence is joined at its 5' end to a T7 promoter sequence.

2. The combination of claim 1, wherein the first amplification oligomer target-hybridizing sequence consists of from 19 to 23 contiguous nucleobases of SEQ ID NO:4.

3. The combination of claim 2, wherein said contiguous nucleobases of SEQ ID NO:4 include SEQ ID NO:2.

4. The combination of claim 3, wherein the first amplification oligomer target-hybridizing sequence is selected from the group consisting of SEQ ID NO:28, SEQ ID NO:29, SEQ ID NO:30, SEQ ID NO:31, SEQ ID NO:32, SEQ ID NO:33, SEQ ID NO:34, and SEQ ID NO:35.

5. The combination of claim 1, wherein the T7 promoter sequence consists of SEQ ID NO:179.

6. An amplification reaction mixture, comprising the at least two amplification oligomers of claim 1, wherein (i) the mixture is a buffered aqueous solution; or (ii) the mixture is a dried composition.

7. A kit comprising the at least two amplification oligomers of claim 1.

8. A method for determining the presence or absence of a Zika virus nucleic acid in a sample, the method comprising the steps of:

(A) contacting a sample with a combination of at least two amplification oligomers configured to amplify a target sequence corresponding to a Zika virus target nucleic acid, wherein the target sequence consists of SEQ ID NO:187, the RNA equivalent of SEQ ID NO:187, or the DNA or RNA complement of SEQ ID NO:187, wherein the first amplification oligomer and the second amplification oligomer are configured to hybridize to opposite ends of the target sequence to generate amplification products;

wherein the first amplification oligomer comprises a target-hybridizing sequence that is from 19 to 23 contiguous nucleobases in length, and wherein the second amplification oligomer comprises a target-hybridizing sequence selected from the group consisting of SEQ ID NO:117 and SEQ ID NO:137, wherein the second amplification oligomer target-hybridizing sequence is joined at its 5' end to a T7 promoter sequence;

(B) performing an in vitro nucleic acid amplification reaction, wherein any Zika virus target nucleic acid present in the sample is used as a template for generating an amplification product; and (C) detecting the presence or absence of the amplification product, thereby determining the presence or absence of the Zika virus nucleic acid in the sample.

9. The method of claim 8, wherein the first amplification oligomer target-hybridizing sequence consists of from 19 to 23 contiguous nucleobases of SEQ ID NO:4.

10. The method of claim 9, wherein said contiguous nucleobases of SEQ ID NO:4 include SEQ ID NO:2.

11. The method of claim 10, wherein the first amplification oligomer target-hybridizing sequence is selected from the group consisting of SEQ ID NO:28, SEQ ID NO:29, SEQ ID NO:30, SEQ ID NO:31, SEQ ID NO:32, SEQ ID NO:33, SEQ ID NO:34, and SEQ ID NO:35.

12. The method of claim 8, wherein the nucleotide sequence of the second amplification oligomer is selected from the group consisting of SEQ ID NO:92 and SEQ ID NO:95.

13. The combination of claim 1, wherein the second amplification oligomer target-hybridizing sequence is SEQ ID NO:117.

14. The combination of claim 13, wherein the nucleotide sequence of the second amplification oligomer is SEQ ID NO:95.

15. The combination of claim 13, wherein the first amplification oligomer target-hybridizing sequence is selected from the group consisting of SEQ ID NO:29, SEQ ID NO:31, SEQ ID NO:32, and SEQ ID NO:33.

16. The combination of claim 14, wherein the first amplification oligomer target-hybridizing sequence is selected from the group consisting of SEQ ID NO:29, SEQ ID NO:31, SEQ ID NO:32, and SEQ ID NO:33.

17. The combination of claim 1, wherein the second amplification oligomer target-hybridizing sequence is SEQ ID NO:137.

18. The combination of claim 17, wherein the nucleotide sequence of the second amplification oligomer is SEQ ID NO:92.

19. The combination of claim 17, wherein the first amplification oligomer target-hybridizing sequence is selected from the group consisting of SEQ ID NO:31, SEQ ID NO:32, and SEQ ID NO:35.

20. The combination of claim 18, wherein the first amplification oligomer target-hybridizing sequence is selected from the group consisting of SEQ ID NO:31, SEQ ID NO:32, and SEQ ID NO:35.

* * * * *

UNITED STATES PATENT AND TRADEMARK OFFICE
CERTIFICATE OF CORRECTION

PATENT NO. : 11,821,046 B2
APPLICATION NO. : 17/032310
DATED : November 21, 2023
INVENTOR(S) : Gao et al.

Page 1 of 3

It is certified that error appears in the above-identified patent and that said Letters Patent is hereby corrected as shown below:

In the Specification

1. In Column 2, Lines 24-25, delete "SEQ I DNO:16" and insert -- SEQ ID NO:16 --, therefor.
2. In Column 2, Line 37, delete "SEQ I DNO:53" and insert -- SEQ ID NO:53 --, therefor.
3. In Column 2, Line 41, delete "SEQ I DNO:18" and insert -- SEQ ID NO:18 --, therefor.
4. In Column 3, Lines 31-32, delete "SEQ ID NO113," and insert -- SEQ ID NO:113, --, therefor.
5. In Column 4, Lines 33-34, delete "SEQ ID NO:95" and insert -- SEQ ID NO:95; --, therefor.
6. In Column 4, Line 35, delete "vi)" and insert -- (vi) --, therefor.
7. In Column 13, Line 48, delete "SEQ I DNO:16" and insert -- SEQ ID NO:16 --, therefor.
8. In Column 13, Line 61, delete "SEQ I DNO:53" and insert -- SEQ ID NO:53 --, therefor.
9. In Column 13, Line 65, delete "SEQ I DNO:18" and insert -- SEQ ID NO:18 --, therefor.
10. In Column 14, Line 54, delete "SEQ ID NO113," and insert -- SEQ ID NO:113, --, therefor.
11. In Column 15, Line 41, delete "SEQ I DNO:16" and insert -- SEQ ID NO:16 --, therefor.
12. In Column 15, Lines 53-54, delete "SEQ I DNO:53" and insert -- SEQ ID NO:53 --, therefor.
13. In Column 15, Line 57, delete "SEQ I DNO:18" and insert -- SEQ ID NO:18 --, therefor.
14. In Column 16, Line 48, delete "SEQ ID NO113," and insert -- SEQ ID NO:113, --, therefor.
15. In Column 25, Line 38, delete "bronchoaveolar" and insert -- bronchoalveolar --, therefor.
16. In Column 26, Line 15, delete "processes." and insert -- process. --, therefor.
17. In Column 26, Line 28, delete "compared" and insert -- compared to --, therefor.
18. In Column 31, Line 29, delete "(See," and insert -- See, --, therefor.
19. In Column 31, Line 31, delete "N Y," and insert -- N.Y., --, therefor.
20. In Column 32, Line 20, delete "(see," and insert -- see, --, therefor.
21. In Column 32, Line 30, delete "minimized" and insert -- minimized. --, therefor.
22. In Column 32, Line 38, delete "(see," and insert -- see, --, therefor.
23. In Column 32, Line 40, delete "N Y," and insert -- N.Y., --, therefor.
24. In Column 33, Line 30, delete "RNAse" and insert -- RNase --, therefor.
25. In Column 33, Line 33, delete "RNAse"" and insert -- RNase" --, therefor.
26. In Column 33, Line 36, delete "RNAse is RNAse" and insert -- RNase is RNase --, therefor.
27. In Column 33, Line 37, delete "RNAse" and insert -- RNase --, therefor.
28. In Column 33, Line 38, delete "RNAses" and insert -- RNases --, therefor.

Signed and Sealed this
Ninth Day of January, 2024

*Katherine Kelly Vidal*

Katherine Kelly Vidal
*Director of the United States Patent and Trademark Office*

29. In Column 33, Line 40, delete "RNAse" and insert -- RNase --, therefor.
30. In Column 34, Line 12, delete "methyl paraben," and insert -- methylparaben, --, therefor.
31. In Column 34, Line 12, delete "propyl paraben," and insert -- propylparaben, --, therefor.
32. In Column 35, Line 67, delete "one of more" and insert -- one or more --, therefor.
33. In Column 36, Line 2, delete "Gen Bank" and insert -- GenBank --, therefor.
34. In Column 37, Line 2, delete "Gen Bank" and insert -- GenBank --, therefor.
35. In Column 38, Line 2, delete "Gen Bank" and insert -- GenBank --, therefor.
36. In Column 42, Line 31, delete "is a has" and insert -- is a --, therefor.
37. In Column 44, Line 22, delete "SEQ ID NO:194" and insert -- SEQ ID NO:194, --, therefor.
38. In Column 44, Line 27, delete "SEQ ID NO:194" and insert -- SEQ ID NO:194, --, therefor.
39. In Column 44, Line 32, delete "SEQ ID NO:194" and insert -- SEQ ID NO:194, --, therefor.
40. In Column 44, Line 37, delete "SEQ ID NO:194" and insert -- SEQ ID NO:194, --, therefor.
41. In Column 44, Line 45, delete "NO:194" and insert -- NO:194, --, therefor.
42. In Column 44, Line 49, delete "SEQ ID NO:194" and insert -- SEQ ID NO:194, --, therefor.
43. In Column 44, Line 54, delete "SEQ ID NO:194" and insert -- SEQ ID NO:194, --, therefor.
44. In Column 44, Line 59, delete "SEQ ID NO:194" and insert -- SEQ ID NO:194, --, therefor.
45. In Column 45, Line 23, delete "target:capture-probe-immobilized-probe" and insert -- target:capture-probe: immobilized-probe --, therefor.
46. In Column 45, Line 28, delete "binds attaches" and insert -- binds --, therefor.
47. In Column 45, Lines 56-57, delete "SEQ ID NO181" and insert -- SEQ ID NO:181 --, therefor.
48. In Column 45, Line 65, delete "tail-sequence-immobilized-probe-sequence" and insert -- tail-sequence: immobilized-probe-sequence --, therefor.
49. In Column 46, Line 9, delete "virus-target:capture-probe-" and insert -- virus-target:capture-probe: --, therefor.
50. In Column 48, Line 11, delete "used a" and insert -- used as a --, therefor.
51. In Column 49, Line 21, delete "and in" and insert -- an in --, therefor.
52. In Column 51, Line 41, delete "capture" and insert -- captured --, therefor.
53. In Column 52, Line 47, delete "reactive light units (RLU)" and insert -- relative light units (RLU) --, therefor.
54. In Column 55, Line 58, delete "reactive light units (RLU)" and insert -- relative light units (RLU) --, therefor.
55. In Column 57, in TABLE 8, Line 8, delete "SEQ ID NO: 89" and insert -- SEQ ID NO: 89; --, therefor.
56. In Column 57, in TABLE 8, Line 9, delete "SEQ ID NO: 95" and insert -- SEQ ID NO: 94; & SEQ ID NO: 95 --, therefor.
57. In Column 57, in TABLE 8, Line 11, delete "SEQ ID NO: 89" and insert -- SEQ ID NO: 89; --, therefor.
58. In Column 57, Line 61, delete "reactive light units (RLU)" and insert -- relative light units (RLU) --, therefor.
59. In Column 58, in TABLE 11, Line 4, delete "% cv" and insert -- % CV --, therefor.
60. In Column 59, in TABLE 11-continued, Line 4, delete "% cv" and insert -- % CV --, therefor.
61. In Column 60, Line 29, delete "conditions 3" and insert -- condition 3 --, therefor.

In the Claims

62. In Column 149, Lines 60-61, in Claim 1, delete "target -hybridizing" and insert -- target-hybridizing --, therefor.
63. In Column 151, Lines 4-5, in Claim 8, delete "target -hybridizing" and insert
-- target-hybridizing --, therefor.

SEQUENCE LISTING

<160> NUMBER OF SEQ ID NOS: 198

<210> SEQ ID NO 1
<211> LENGTH: 10794
<212> TYPE: DNA
<213> ORGANISM: Zika Virus strain MR 766
<300> PUBLICATION INFORMATION:
<308> DATABASE ACCESSION NUMBER: AY632535.2
<309> DATABASE ENTRY DATE: 2009-04-06
<313> RELEVANT RESIDUES IN SEQ ID NO: (1)..(10794)

<400> SEQUENCE: 1

| | | | | | |
|---|---|---|---|---|---|
| agttgttgat | ctgtgtgagt | cagactgcga | cagttcgagt | ctgaagcgag | agctaacaac | 60 |
| agtatcaaca | ggtttaattt | ggatttggaa | acgagagttt | ctggtcatga | aaaaccccaa | 120 |
| agaagaaatc | cggaggatcc | ggattgtcaa | tatgctaaaa | cgcggagtag | cccgtgtaaa | 180 |
| cccccttggga | ggtttgaaga | ggttgccagc | cggacttctg | ctgggtcatg | acccatcag | 240 |
| aatggttttg | gcgatactag | ccttttttgag | atttacagca | atcaagccat | cactgggcct | 300 |
| tatcaacaga | tggggttccg | tggggaaaaa | agaggctatg | gaaataataa | gaagttcaa | 360 |
| gaaagatctt | gctgccatgt | tgagaataat | caatgctagg | aaagagagga | agagacgtgg | 420 |
| cgcagacacc | agcatcggaa | tcattggcct | cctgctgact | acagccatgg | cagcagagat | 480 |
| cactagacgc | gggagtgcat | actacatgta | cttggatagg | agcgatgccg | ggaaggccat | 540 |
| ttcgtttgct | accacattgg | gagtgaacaa | gtgccacgta | cagatcatgg | acctcgggca | 600 |
| catgtgtgac | gccaccatga | gttatgagtg | ccctatgctg | gatgagggag | tggaaccaga | 660 |
| tgatgtcgat | tgctggtgca | acacgacatc | aacttgggtt | gtgtacggaa | cctgtcatca | 720 |
| caaaaaggt | gaggcacggc | gatctagaag | agccgtgacg | ctcccttctc | actctacaag | 780 |
| gaagttgcaa | acgcggtcgc | agacctggtt | agaatcaaga | gaatacacga | agcacttgat | 840 |
| caaggttgaa | aactggatat | tcaggaaccc | cgggttgcg | ctagtggccg | ttgccattgc | 900 |
| ctggcttttg | ggaagctcga | cgagccaaaa | agtcatatac | ttggtcatga | tactgctgat | 960 |
| tgccccggca | tacagtatca | ggtgcattgg | agtcagcaat | agagacttcg | tggagggcat | 1020 |
| gtcaggtggg | acctgggttg | atgttgtctt | ggaacatgga | ggctgcgtta | ccgtgatggc | 1080 |
| acaggacaag | ccaacagtcg | catagagtt | ggtcacgacg | acggttagta | acatggccga | 1140 |
| ggtaagatcc | tattgctacg | aggcatcgat | atcggacatg | gcttcggaca | gtcgttgccc | 1200 |
| aacacaaggt | gaagcctacc | ttgacaagca | atcagacact | caatatgtct | gcaaaagaac | 1260 |
| attagtggac | agaggttggg | gaaacggttg | tggactttttt | ggcaaaggga | gcttggtgac | 1320 |
| atgtgccaag | tttacgtgtt | ctaagaagat | gaccgggaag | agcattcaac | cggaaaatct | 1380 |
| ggagtatcgg | ataatgctat | cagtgcatgg | ctcccagcat | agcgggatga | ttggatatga | 1440 |
| aactgacgaa | gatagagcga | aagtcgaggt | tacgcctaat | tcaccaagag | cggaagcaac | 1500 |
| cttgggaggc | tttggaagct | taggacttga | ctgtgaacca | aggacaggcc | ttgactttttc | 1560 |
| agatctgtat | tacctgacca | tgaacaataa | gcattggttg | gtgcacaaag | agtggtttca | 1620 |
| tgacatccca | ttgccttggc | atgctgggc | agacaccgga | actccacact | ggaacaacaa | 1680 |
| agaggcattg | gtagaattca | aggatgccca | cgccaagagg | caaaccgtcg | tcgttctggg | 1740 |
| gagccaggaa | ggagccgttc | acacggctct | cgctggagct | ctagaggctg | agatggatgg | 1800 |
| tgcaaaggga | aggctgttct | ctggccattt | gaaatgccgc | ctaaaaatgg | acaagcttag | 1860 |
| attgaagggc | gtgtcatatt | ccttgtgcac | tgccggcattc | acattccca | aggtcccagc | 1920 |
| tgaaacactg | catggaacag | tcacagtgga | ggtgcagtat | gcagggacag | atggaccctg | 1980 |

```
caagatccca gtccagatgg cggtggacat gcagaccctg accccagttg gaaggctgat    2040
aaccgccaac cccgtgatta ctgaaagcac tgagaactca agatgatgt tggagcttga     2100
cccaccattt ggggattctt acattgtcat aggagttggg gacaagaaaa tcacccacca    2160
ctggcatagg agtggtagca ccatcggaaa ggcatttgag gccactgtga gaggcgccaa    2220
gagaatggca gtcctggggg atacagcctg ggacttcgga tcagtcgggg gtgtgttcaa    2280
ctcactgggt aagggcattc accagatttt tggagcagcc ttcaaatcac tgtttggagg    2340
aatgtcctgg ttctcacaga tcctcatagg cacgctgcta gtgtggttag gtttgaacac    2400
aaagaatgga tctatctccc tcacatgctt ggccctgggg ggagtgatga tcttcctctc    2460
cacggctgtt tctgctgacg tggggtgctc agtggacttc tcaaaaaagg aaacgagatg    2520
tggcacgggg gtattcatct ataatgatgt tgaagcctgg agggaccggt acaagtacca    2580
tcctgactcc ccccgcagat tggcagcagc agtcaagcag gcctgggaag aggggatctg    2640
tgggatctca tccgtttcaa gaatggaaaa catcatgtgg aaatcagtag aaggggagct    2700
caatgctatc ctagaggaga atggagttca actgacagtt gttgtgggat ctgtaaaaaa    2760
ccccatgtgg agaggtccac aaagattgcc agtgcctgtg aatgagctgc cccatggctg    2820
gaaagcctgg gggaaatcgt attttgttag ggcggcaaag accaacaaca gttttgttgt    2880
cgacggtgac acactgaagg aatgtccgct tgagcacaga gcatggaata gtttctcttgt    2940
ggaggatcac gggtttggag tcttccacac cagtgtctgg cttaaggtca gagaagatta    3000
ctcattagaa tgtgacccag ccgtcatagg aacagctgtt aagggaaggg aggccgcgca    3060
cagtgatctg ggctattgga ttgaaagtga aagaatgac acatggaggc tgaagagggc     3120
ccacctgatt gagatgaaaa catgtgaatg ccaaagtct cacacattgt ggacagatgg      3180
agtagaagaa agtgatctta tcatcccaa gtctttagct ggtccactca gccaccacaa      3240
caccagagag ggttacagaa cccaagtgaa agggccatgg cacagtgaag agcttgaaat    3300
ccggtttgag gaatgtccag gcaccaaggt ttacgtggag gagacatgcg gaactagagg    3360
accatctctg agatcaacta ctgcaagtgg aagggtcatt gaggaatggt gctgtaggga    3420
atgcacaatg cccccactat cgtttcgagc aaaagacggc tgctggtatg gaatggagat    3480
aaggcccagg aaagaaccag agagcaactt agtgaggtca atggtgacag cggggtcaac    3540
cgatcatatg gaccacttct ctcttggagt gcttgtgatt ctactcatgg tgcaggaggg    3600
gttgaagaag agaatgacca caaagatcat catgagcaca tcaatggcag tgctggtagt    3660
catgatcttg ggaggatttt caatgagtga cctggccaag cttgtgatcc tgatgggtgc    3720
tactttcgca gaaatgaaca ctggaggaga tgtagctcac ttggcattgg tagcggcatt    3780
taaagtcaga ccagccttgc tggtctcctt cattttcaga gccaattgga cacccgtga    3840
gagcatgctg ctagccctgg cttcgtgtct tctgcaaact gcgatctctg ctcttgaagg    3900
tgacttgatg gtcctcatta tggatttgc tttggcctgg ttggcaattc gagcaatggc    3960
cgtgccacgc actgacaaca tcgctctacc aatcttggct gctctaacac cactagctcg    4020
aggcacactg ctcgtggcat ggagagcggg cctggctact tgtggaggga tcatgctcct    4080
ctccctgaaa gggaaggta gtgtgaagaa gaacctgcca tttgtcatgg ccctgggatt     4140
gacagctgtg agggtagtag accctattaa tgtggtagga ctactgttac tcacaaggag    4200
tgggaagcgg agctggcccc ctagtgaagt tctcacagcc gttggcctga tatgtgcact    4260
ggccggaggg tttgccaagg cagacattga gatggctgga cccatggctg cagtaggctt    4320
gctaattgtc agctatgtgg tctcgggaaa gagtgtggac atgtacattg aaagagcagg    4380
```

```
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta tacctttgc   4560
tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga agttggatgc   4860
agcttgggat ggactcagcg aggtacagct tttggccgta cctcccggag agagggccag   4920
aaacattcag accctgcctg gaatattcaa gacaaaggac ggggacatcg gagcagttgc   4980
tctggactac cctgcaggga cctcaggatc tccgatccta gacaaatgtg aagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
gcagctaact gtcttggatc tgcatccagg agccggaaaa accaggagag ttcttcctga   5220
aatagtccgt gaagccataa aaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gacccctcaa gtatagctgc aagaggatac atatcaacaa gggttgaaat   5520
gggcgaggcg gctgccattt tatgactgc cacaccacca ggaacccgtg atgcgtttcc   5580
tgactctaac tcaccaatca tggacacaga agtggaagtc ccagagagag cctggagctc   5640
aggctttgat tgggtgacag accattctgg gaaaacagtt tggttcgttc aagcgtgag   5700
aaacggaaat gaaatcgcag cctgtctgac aaaggctgga aagcgggtca tacagctcag   5760
caggaagact tttgagacag aatttcagaa aacaaaaat caagagtggg actttgtcat   5820
aacaactgac atctcagaga tgggcgccaa cttcaaggct gaccgggtca tagactctag   5880
gagatgccta aaaccagtca tacttgatgg tgagagagtc atcttggctg ggcccatgcc   5940
tgtcacgcat gctagtgctg ctcagaggag aggacgtata ggcaggaacc ctaacaaacc   6000
tggagatgag tacatgtatg gaggtgggtg tgcagagact gatgaaggcc atgcacactg   6060
gcttgaagca agaatgcttc ttgacaacat ctacctccag gatggcctca gcctcgct   6120
ctatcggcct gaggccgata aggtagccgc cattgaggga gagtttaagc tgaggacaga   6180
gcaaaggaag accttcgtgg aactcatgaa gagaggagac cttcccgtct ggctagccta   6240
tcaggttgca tctgccggaa taacttacac agacagaaga tggtgctttg atggcacaac   6300
caacaacacc ataatggaag acagtgtacc agcagaggtt tggacaaagt atggagagaa   6360
gagagtgctc aaaccgagat ggatggatgc tagggtctgt tcagaccatg cggccctgaa   6420
gtcgttcaaa gaattcgccg ctggaaaaag aggagcggct ttgggagtaa tggaggccct   6480
gggaacactg ccaggacaca tgacagagag gtttcaggaa gccattgaca acctcgccgt   6540
gctcatgcga gcagagactg aagcaggcc ttataaggca gcggcagccc aactgccgga   6600
gaccctagag accattatgc tcttaggttt gctgggaaca gtttcactgg ggatcttctt   6660
cgtcttgatg cggaataagg gcatcggaaa gatgggcttt ggaatggtaa cccttgggc   6720
cagtgcatgg ctcatgtggc tttcggaaat tgaaccagcc agaattgcat gtgtcctcat   6780
```

-continued

```
tgttgtgttt ttattactgg tggtgctcat acccgagcca gagaagcaaa gatctcccca   6840
agataaccag atggcaatta tcatcatggt ggcagtgggc cttctaggtt tgataactgc   6900
aaacgaactt ggatggctgg aaagaacaaa aaatgacata gctcatctaa tgggaaggag   6960
agaagaagga gcaaccatgg gattctcaat ggacattgat ctgcggccag cctccgcctg   7020
ggctatctat gccgcattga caactctcat cacccccagct gtccaacatg cggtaaccac   7080
ttcatacaac aactactcct taatggcgat ggccacacaa gctggagtgc tgtttggcat   7140
gggcaaaggg atgccattta tgcatgggga ccttggagtc ccgctgctaa tgatgggttg   7200
ctattcacaa ttaaccccc tgactctgat agtagctatc attctgcttg tggcgcacta   7260
catgtacttg atcccaggcc tacaagcggc agcagcgcgt gctgcccaga aaggacagc   7320 agctggcatc atgaagaatc ccgttgtgga tggaatagtg gtaactgaca ttgacacaat   7380
gacaatagac ccccaggtgg agaagaagat gggacaagtg ttactcatag cagtagccat   7440
ctccagtgct gtgctgctgc ggaccgcctg gggatggggg gaggctggag ctctgatcac   7500
agcagcgacc tccaccttgt gggaaggctc tccaaacaaa tactgaaact cctctacagc   7560
cacctcactg tgcaacatct tcagaggaag ctatctggca ggagcttccc ttatctatac   7620
agtgacgaga aacgctggcc tggttaagag acgtggaggt gggacgggag agactctggg   7680
agagaagtgg aaagctcgtc tgaatcagat gtcggccctg gagttctact cttataaaaa   7740
gtcaggtatc actgaagtgt gtagagagga ggctcgccgt gccctcaagg atggagtggc   7800
cacaggagga catgccgtat cccgggggaag tgcaaagatc agatggttgg aggagagagg   7860
atatctgcag ccctatggga aggttgttga cctcggatgt ggcagagggg gctggagcta   7920
ttatgccgcc accatccgca aagtgcagga ggtgagagga tacacaaagg gaggtcccgg   7980
tcatgaagaa cccatgctgg tgcaaagcta gggtggaac atagttcgtc tcaagagtgg   8040
agtggacgtc ttccacatgg cggctgagcc gtgtgacact ctgctgtgtg acataggtga   8100
gtcatcatct agtcctgaag tggaagagac acgaacactc agagtgctct ctatggtggg   8160
ggactggctt gaaaaaagac caggggcctt ctgtataaag gtgctgtgcc catacaccag   8220
cactatgatg gaaaccatgg agcgactgca acgtaggcat gggggaggat tagtcagagt   8280
gccattgtgt cgcaactcca cacatgagat gtactgggtc tctggggcaa agagcaacat   8340
cataaaaagt gtgtccacca caagtcagct cctcctggga cgcatggatg cccccaggag   8400
gccagtgaaa tatgaggagg atgtgaacct cggctcgggt acacgagctg tggcaagctg   8460
tgctgaggct cctaacatga aaatcatcgg caggcgcatt gagagaatcc gcaatgaaca   8520
tgcagaaaca tggtttcttg atgaaaacca cccatacagg acatgggcct accatgggag   8580
ctacgaagcc cccacgcaag gatcagcgtc ttccctcgtg aacggggttg ttagactcct   8640
gtcaaagcct tgggacgtgg tgactggagt tacaggaata gccatgactg acaccacacc   8700
atacggccaa caaagagtct tcaaagaaaa agtggacacc agggtgccag atccccaaga   8760
aggcactcgc caggtaatga acatagtctc ttcctggctg tggaaggagc tggggaaacg   8820
caagcggcca cgcgtctgca ccaaagaaga gtttatcaac aaggtgcgca gcaatgcagc   8880
actgggagca atatttgaag aggaaaaaga atggaagacg gctgtggaag ctgtgaatga   8940
tccaaggttt tgggcctag tggatagggga gagagaacac cacctgagag gagagtgtca   9000
cagctgtgtg tacaacatga tgggaaaaag agaaaagaag caaggagagt tcggaaagc   9060 aaaaggtagc cgcgccatct ggtacatgtg gttgggagcc agattcttgg agtttgaagc   9120
ccttggattc ttgaacgagg accattggat gggaagagaa aactcaggag gtggagtcga   9180
```

```
agggttagga ttgcaaagac ttggatacat tctagaagaa atgaatcggg caccaggagg    9240
aaagatgtac gcagatgaca ctgctggctg ggacacccgc attagtaagt ttgatctgga    9300
gaatgaagct ctgattacca accaaatgga ggaagggcac agaactctgg cgttggccgt    9360
gattaaatac ataccaaa acaaagtggt gaaggttctc agaccagctg aaggaggaaa     9420
aacagttatg gacatcattt caagacaaga ccagagaggg agtggacaag ttgtcactta    9480
tgctctcaac acattcacca acttggtggt gcagcttatc cggaacatgg aagctgagga    9540
agtgttagag atgcaagact tatggttgtt gaggaagcca gagaaagtga ccagatggtt    9600
gcagagcaat ggatgggata gactcaaacg aatggcggtc agtggagatg actgcgttgt    9660
gaagccaatc gatgataggt ttgcacatgc cctcaggttc ttgaatgaca tgggaaaagt    9720
taggaaagac acacaggagt ggaaaccctc gactggatgg agcaattggg aagaagtccc    9780
gttctgctcc caccacttca acaagctgta cctcaaggat gggagatcca ttgtggtccc    9840
ttgccgccac caagatgaac tgattggccg agctcgcgtc tcaccagggg caggatggag    9900
catccgggag actgcctgtc ttgcaaaatc atatgcgcag atgtggcagc tcctttattt    9960
ccacagaaga gaccttcgac tgatggctaa tgccatttgc tcggctgtgc cagttgactg   10020
ggtaccaact gggagaacca cctggtcaat ccatggaaag ggagaatgga tgaccactga   10080
ggacatgctc atggtgtgga atagagtgtg gattgaggag aacgaccata tggaggacaa   10140
gactcctgta acaaaatgga cagacattcc ctatctagga aaaagggagg acttatggtg   10200
tggatccctt atagggcaca gaccccgcac cacttgggct gaaaacatca agacacagt    10260 caacatggtg cgcaggatca taggtgatga agaaaagtac atggactatc tatccaccca   10320
agtccgctac ttgggtgagg aagggtccac acccggagtg ttgtaagcac caattttagt   10380
gttgtcaggc ctgctagtca gccacagttt ggggaaagct gtgcagcctg taacccccc     10440 aggagaagct gggaaaccaa gctcatagtc aggccgagaa cgccatggca cggaagaagc   10500
catgctgcct gtgagcccct cagaggacac tgagtcaaaa accccacgc gcttggaagc    10560 gcaggatggg aaaagaaggt ggcgaccttc cccaccctc aatctggggc ctgaactgga    10620
gactagctgt gaatctccag cagagggact agtggttaga ggagaccccc cggaaaacgc   10680
aaaacagcat attgacgtgg gaaagaccag agactccatg agtttccacc acgctggccg   10740
ccaggcacag atcgccgaac ttcggcggcc ggtgtgggga aatccatggt ttct           10794
```

```
<210> SEQ ID NO 2
<211> LENGTH: 19
<212> TYPE: DNA
<213> ORGANISM: Artificial Sequence
<220> FEATURE:
<223> OTHER INFORMATION: Oligonucleotide

<400> SEQUENCE: 2
tcycttggag tgcttgtga                                                    19

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide

<400> SEQUENCE: 3
tcycttggag tgcttgtgat t                                                 21
```

```
<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
tcycttggag tgcttgtgat tyt                                              23

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide

<400> SEQUENCE: 5
tcycttggag tgcttgtgat ty                                               22

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide

<400> SEQUENCE: 6
yccyaayaaa cctggagatg agta                                             24

<210> SEQ ID NO 7
<211> LENGTH: 16
<212> TYPE: DNA
<213> ORGANISM: Artificial Sequence
<220> FEATURE:
<223> OTHER INFORMATION: Oligonucleotide

<400> SEQUENCE: 7
aayaaacctg gagatg                                                      16

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide

<400> SEQUENCE: 8
yaayaaacct ggagatg                                                     17

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
tggcttgaag caagaatgct                                                  20

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide
```

```
<400> SEQUENCE: 10
gcttgaagca agaat                                                    15

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
aggacagcag ctggcatcat                                               20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
aggacggcag ctggcatcat                                               20

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide

<400> SEQUENCE: 13
aggacagcag ctggcatcat g                                             21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide

<400> SEQUENCE: 14
aggacggcag ctggcatcat g                                             21

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
aggacagcag ctggcatcat ga                                            22

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide

<400> SEQUENCE: 16
aggacggcag ctggcatcat ga                                            22
```

```
<210> SEQ ID NO 17
<211> LENGTH: 23
<212> TYPE: DNA
<213> ORGANISM: Artificial Sequence
<220> FEATURE:
<223> OTHER INFORMATION: Oligonucleotide

<400> SEQUENCE: 17
aggacagcag ctggcatcat gaa                                              23

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide

<400> SEQUENCE: 18
aggacggcag ctggcatcat gaa                                              23

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
acggcagctg gcatcatgaa                                                  20

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide

<400> SEQUENCE: 20
gacggcagct ggcatcatga a                                                21

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide

<400> SEQUENCE: 21
acagcagctg gcatcatgaa gaa                                              23

<210> SEQ ID NO 22
<211> LENGTH: 26
<212> TYPE: DNA
<213> ORGANISM: Artificial Sequence
<220> FEATURE:
<223> OTHER INFORMATION: Oligonucleotide

<400> SEQUENCE: 22
aggacagcag ctggcatcat gaagaa                                           26

<210> SEQ ID NO 23
<211> LENGTH: 26
<212> TYPE: DNA
<213> ORGANISM: Artificial Sequence
<220> FEATURE:
<223> OTHER INFORMATION: Oligonucleotide
```

```
<400> SEQUENCE: 23
agaacagcag ctggcatcat gaagaa                                    26

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide

<400> SEQUENCE: 24
agracrgcag ctggcatcat gaagaa                                    26

<210> SEQ ID NO 25
<211> LENGTH: 17
<212> TYPE: DNA
<213> ORGANISM: Artificial Sequence
<220> FEATURE:
<223> OTHER INFORMATION: Oligonucleotide

<400> SEQUENCE: 25
acrgcagctg gcatcat                                              17

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide

<400> SEQUENCE: 26
racrgcagct ggcatcatga a                                         21

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
gttgtggatg gaatagtggt                                           20

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide

<400> SEQUENCE: 28
tctcttggag tgcttgtgat tc                                        22

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide

<400> SEQUENCE: 29
tctcttggag tgcttgtgat t                                         21
```

```
<210> SEQ ID NO 30
<211> LENGTH: 19
<212> TYPE: DNA
<213> ORGANISM: Artificial Sequence
<220> FEATURE:
<223> OTHER INFORMATION: Oligonucleotide

<400> SEQUENCE: 30
tctcttggag tgcttgtga                                              19

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide

<400> SEQUENCE: 31
tctcttggag tgcttgtgat tct                                         23

<210> SEQ ID NO 32
<211> LENGTH: 23
<212> TYPE: DNA
<213> ORGANISM: Artificial Sequence
<220> FEATURE:
<223> OTHER INFORMATION: Oligonucleotide

<400> SEQUENCE: 32
tcccttggag tgcttgtgat tct                                         23

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide

<400> SEQUENCE: 33
tcccttggag tgcttgtgat tc                                          22

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide

<400> SEQUENCE: 34
tcccttggag tgcttgtgat t                                           21

<210> SEQ ID NO 35
<211> LENGTH: 19
<212> TYPE: DNA
<213> ORGANISM: Artificial Sequence
<220> FEATURE:
<223> OTHER INFORMATION: Oligonucleotide

<400> SEQUENCE: 35
tcccttggag tgcttgtga                                              19

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide
```

<400> SEQUENCE: 36
aacaaacctg gagatgagta                                              20

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide

<400> SEQUENCE: 37
caacaaacct ggagatgagt a                                            21

<210> SEQ ID NO 38
<211> LENGTH: 19
<212> TYPE: DNA
<213> ORGANISM: Artificial Sequence
<220> FEATURE:
<223> OTHER INFORMATION: Oligonucleotide

<400> SEQUENCE: 38
aacaaacctg gagatgagt                                               19

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39
caacaaacct ggagatgagt                                              20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
caataaacct ggagatgagt                                              20

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide

<400> SEQUENCE: 41
cccaataaac ctggagatga gt                                           22

<210> SEQ ID NO 42
<211> LENGTH: 23
<212> TYPE: DNA
<213> ORGANISM: Artificial Sequence
<220> FEATURE:
<223> OTHER INFORMATION: Oligonucleotide

<400> SEQUENCE: 42
ccyaayaaac ctggagatga gta                                          23

```
<210> SEQ ID NO 43
<211> LENGTH: 23
<212> TYPE: DNA
<213> ORGANISM: Artificial Sequence
<220> FEATURE:
<223> OTHER INFORMATION: Oligonucleotide

<400> SEQUENCE: 43
cccaacaaac ctggagatga gta                                              23

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
yccyaayaaa cctggagatg                                                  20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide

<400> SEQUENCE: 45
tcctaacaaa cctggagatg                                                  20

<210> SEQ ID NO 46
<211> LENGTH: 22
<212> TYPE: DNA
<213> ORGANISM: Artificial Sequence
<220> FEATURE:
<223> OTHER INFORMATION: Oligonucleotide

<400> SEQUENCE: 46
cccaacaaac ctggagatga gt                                               22

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide

<400> SEQUENCE: 47
ccyaayaaac ctggagatga g                                                21

<210> SEQ ID NO 48
<211> LENGTH: 21
<212> TYPE: DNA
<213> ORGANISM: Artificial Sequence
<220> FEATURE:
<223> OTHER INFORMATION: Oligonucleotide

<400> SEQUENCE: 48
cccaacaaac ctggagatga g                                                21

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide
```

```
<400> SEQUENCE: 49
agracrgcag ctggcatcat gaaga                                         25

<210> SEQ ID NO 50
<211> LENGTH: 26
<212> TYPE: DNA
<213> ORGANISM: Artificial Sequence
<220> FEATURE:
<223> OTHER INFORMATION: Oligonucleotide

<400> SEQUENCE: 50
agracrgcag ctggcatcat gaagaa                                        26

<210> SEQ ID NO 51
<211> LENGTH: 22
<212> TYPE: DNA
<213> ORGANISM: Artificial Sequence
<220> FEATURE:
<223> OTHER INFORMATION: Oligonucleotide

<400> SEQUENCE: 51
agracrgcag ctggcatcat ga                                            22

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
agracrgcag ctggcatcat                                               20

<210> SEQ ID NO 53
<211> LENGTH: 23
<212> TYPE: DNA
<213> ORGANISM: Artificial Sequence
<220> FEATURE:
<223> OTHER INFORMATION: Oligonucleotide

<400> SEQUENCE: 53
agracrgcag ctggcatcat gaa                                           23

<210> SEQ ID NO 54
<211> LENGTH: 19
<212> TYPE: DNA
<213> ORGANISM: Artificial Sequence
<220> FEATURE:
<223> OTHER INFORMATION: Oligonucleotide

<400> SEQUENCE: 54
traagaagag aatgaccac                                                19

<210> SEQ ID NO 55
<211> LENGTH: 19
<212> TYPE: DNA
<213> ORGANISM: Artificial Sequence
<220> FEATURE:
<223> OTHER INFORMATION: Oligonucleotide

<400> SEQUENCE: 55
uraagaagag aaugaccac                                                19
```

```
<210> SEQ ID NO 56
<211> LENGTH: 20
<212> TYPE: DNA
<213> ORGANISM: Artificial Sequence
<220> FEATURE:
<223> OTHER INFORMATION: Oligonucleotide

<400> SEQUENCE: 56
gttgtggakg gaatagtggt                                               20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide

<400> SEQUENCE: 57
guuguggakg gaauaguggt                                               20

<210> SEQ ID NO 58
<211> LENGTH: 19
<212> TYPE: DNA
<213> ORGANISM: Artificial Sequence
<220> FEATURE:
<223> OTHER INFORMATION: Oligonucleotide

<400> SEQUENCE: 58
ugaagaagag aaugaccac                                                19

<210> SEQ ID NO 59
<211> LENGTH: 19
<212> TYPE: DNA
<213> ORGANISM: Artificial Sequence
<220> FEATURE:
<223> OTHER INFORMATION: Oligonucleotide

<400> SEQUENCE: 59
uguauggagg ugggugugc                                                19

<210> SEQ ID NO 60
<211> LENGTH: 21
<212> TYPE: DNA
<213> ORGANISM: Artificial Sequence
<220> FEATURE:
<223> OTHER INFORMATION: Oligonucleotide

<400> SEQUENCE: 60
cuggcuugaa gcaagaaugc t                                             21

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide

<400> SEQUENCE: 61
uggcuugaag caagaaugct                                               20

<210> SEQ ID NO 62
<211> LENGTH: 17
<212> TYPE: DNA
<213> ORGANISM: Artificial Sequence
<220> FEATURE:
<223> OTHER INFORMATION: Oligonucleotide
```

```
<400> SEQUENCE: 62
uggcuugaag caagaat                                              17

<210> SEQ ID NO 63
<211> LENGTH: 18
<212> TYPE: DNA
<213> ORGANISM: Artificial Sequence
<220> FEATURE:
<223> OTHER INFORMATION: Oligonucleotide

<400> SEQUENCE: 63
gcuugaagca agaaugct                                             18

<210> SEQ ID NO 64
<211> LENGTH: 13
<212> TYPE: DNA
<213> ORGANISM: Artificial Sequence
<220> FEATURE:
<223> OTHER INFORMATION: Oligonucleotide

<400> SEQUENCE: 64
cattgacaca atg                                                  13

<210> SEQ ID NO 65
<211> LENGTH: 23
<212> TYPE: DNA
<213> ORGANISM: Artificial Sequence
<220> FEATURE:
<223> OTHER INFORMATION: Oligonucleotide

<400> SEQUENCE: 65
actgacattg acacaatgac wat                                       23

<210> SEQ ID NO 66
<211> LENGTH: 23
<212> TYPE: DNA
<213> ORGANISM: Artificial Sequence
<220> FEATURE:
<223> OTHER INFORMATION: Oligonucleotide

<400> SEQUENCE: 66
acugacauug acacaaugac wat                                       23

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
gacauugaca caaugacwat                                           20

<210> SEQ ID NO 68
<211> LENGTH: 18
<212> TYPE: DNA
<213> ORGANISM: Artificial Sequence
<220> FEATURE:
<223> OTHER INFORMATION: Oligonucleotide

<400> SEQUENCE: 68
cauugacaca augacwat                                             18
```

```
<210> SEQ ID NO 69
<211> LENGTH: 20
<212> TYPE: DNA
<213> ORGANISM: Artificial Sequence
<220> FEATURE:
<223> OTHER INFORMATION: Oligonucleotide

<400> SEQUENCE: 69 guguggaug gaauaguggt                                                  20

<210> SEQ ID NO 70
<211> LENGTH: 23
<212> TYPE: DNA
<213> ORGANISM: Artificial Sequence
<220> FEATURE:
<223> OTHER INFORMATION: Oligonucleotide

<400> SEQUENCE: 70
acugacauug acacaaugac aat                                             23

<210> SEQ ID NO 71
<211> LENGTH: 18
<212> TYPE: DNA
<213> ORGANISM: Artificial Sequence
<220> FEATURE:
<223> OTHER INFORMATION: Oligonucleotide

<400> SEQUENCE: 71
acugacauug acacaaug                                                   18

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide

<400> SEQUENCE: 72
gacauugaca caaugacaat                                                 20

<210> SEQ ID NO 73
<211> LENGTH: 18
<212> TYPE: DNA
<213> ORGANISM: Artificial Sequence
<220> FEATURE:
<223> OTHER INFORMATION: Oligonucleotide

<400> SEQUENCE: 73
cauugacaca augacaat                                                   18

<210> SEQ ID NO 74
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 74
aatttaatac gactcactat agggagagtc attgtgtcaa tgtcag                    46

<210> SEQ ID NO 75
<211> LENGTH: 47
<212> TYPE: DNA
<213> ORGANISM: Artificial Sequence
```

```
<220> FEATURE:
<223> OTHER INFORMATION: Oligonucleotide
<220> FEATURE:
<221> NAME/KEY: promoter
<222> LOCATION: (1)..(27)

<400> SEQUENCE: 75
aatttaatac gactcactat agggagagtc attgtgtcaa tgtcagt         47

<210> SEQ ID NO 76
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 76
aatttaatac gactcactat agggagatca ttgtgtcaat gtcagt          46

<210> SEQ ID NO 77
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 77
aatttaatac gactcactat agggagagtc watwgtcatt gtgtca          46

<210> SEQ ID NO 78
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 78
aatttaatac gactcactat agggagagtc tattgtcatt gtgtca          46

<210> SEQ ID NO 79
<211> LENGTH: 44
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 79
aatttaatac gactcactat agggagagtc tattgtcatt gtgt            44

<210> SEQ ID NO 80
<211> LENGTH: 50
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 80
aatttaatac gactcactat agggagaatt gtcattgtgt caatgtcagt              50

<210> SEQ ID NO 81
<211> LENGTH: 48
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 81
aatttaatac gactcactat agggagaatt gtcattgtgt caatgtca                48

<210> SEQ ID NO 82
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 82
aatttaatac gactcactat agggagaatt gtcattgtgt caatgtc                 47

<210> SEQ ID NO 83
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 83
aatttaatac gactcactat agggagaatt gtcattgtgt caatgt                  46

<210> SEQ ID NO 84
<211> LENGTH: 44
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 84
aatttaatac gactcactat agggagaytg ycccatctty ttyt                    44

<210> SEQ ID NO 85
<211> LENGTH: 44
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 85
aatttaatac gactcactat agggagattg tcccatcttc ttct                    44

<210> SEQ ID NO 86
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 86
aatttaatac gactcactat agggagagta acacttgtcc catctt                  46

<210> SEQ ID NO 87
<211> LENGTH: 55
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 87
aatttaatac gactcactat agggagactg ctatgagtaa cacttgtccc atctt         55

<210> SEQ ID NO 88
<211> LENGTH: 53
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 88
aatttaatac gactcactat agggagagtc watwgtcatt gtgtcaatgt cag           53

<210> SEQ ID NO 89
<211> LENGTH: 53
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 89
aatttaatac gactcactat agggagagtc tattgtcatt gtgtcaatgt cag           53

<210> SEQ ID NO 90
<211> LENGTH: 52
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 90
aatttaatac gactcactat agggagacta ccagcactgc cattgatgtg ct            52

<210> SEQ ID NO 91
<211> LENGTH: 49
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 91
aatttaatac gactcactat agggagacca gcactgccat tgatgtgct               49

<210> SEQ ID NO 92
<211> LENGTH: 49
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 92
aatttaatac gactcactat agggagacta ccagcactgc cattgatgt               49

<210> SEQ ID NO 93
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 93
aatttaatac gactcactat agggagatrr ctaccagcac tgccat                  46

<210> SEQ ID NO 94
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 94
aatttaatac gactcactat agggagatag ctaccagcac tgccat                  46

<210> SEQ ID NO 95
<211> LENGTH: 51
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 95
aatttaatac gactcactat agggagacta ccagcactgc cattgatgtg c          51

<210> SEQ ID NO 96
<211> LENGTH: 48
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 96
aatttaatac gactcactat agggagatrr ctaccagcac tgccattg              48

<210> SEQ ID NO 97
<211> LENGTH: 48
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 97
aatttaatac gactcactat agggagatag ctaccagcac tgccattg              48

<210> SEQ ID NO 98
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 98
aatttaatac gactcactat agggagaagc attcttgctt caagcca               47

<210> SEQ ID NO 99
<211> LENGTH: 46
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 99
aatttaatac gactcactat agggagagca ttcttgcttc aagcca                46

<210> SEQ ID NO 100
<211> LENGTH: 49
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 100
aatttaatac gactcactat agggagagga gcattcttgc ttcaagcca        49

<210> SEQ ID NO 101
<211> LENGTH: 49
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 101
aatttaatac gactcactat agggagagtc aagaagcatt cttgcttca        49

<210> SEQ ID NO 102
<211> LENGTH: 50
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 102
aatttaatac gactcactat agggagatag agcgaggcta tgaggccatc        50

<210> SEQ ID NO 103
<211> LENGTH: 49
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 103
aatttaatac gactcactat agggagatag agcgaggcta tgaggccat        49

<210> SEQ ID NO 104
<211> LENGTH: 48
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 104
aatttaatac gactcactat agggagatag agcgaggcta tgaggcca         48

<210> SEQ ID NO 105
<211> LENGTH: 45
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 105
aatttaatac gactcactat agggagatag agcgaggcta tgagg          45

<210> SEQ ID NO 106
<211> LENGTH: 44
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 106
aatttaatac gactcactat agggagatag agcgaggcta tgag           44

<210> SEQ ID NO 107
<211> LENGTH: 44
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 107
aatttaatac gactcactat agggagagtc watwgtcatt gtgt           44

<210> SEQ ID NO 108
<211> LENGTH: 55
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 108
aatttaatac gactcactat agggagactg cyatgagtar cacytgyccc atctt    55

<210> SEQ ID NO 109
<211> LENGTH: 49
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 109
aatttaatac gactcactat agggagagra gcattcttgc ttcaagcca          49

<210> SEQ ID NO 110
<211> LENGTH: 49
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: promoter
<222> LOCATION: (1)..(27)

<400> SEQUENCE: 110
aatttaatac gactcactat agggagagtc aagragcatt cttgcttca                49

<210> SEQ ID NO 111
<211> LENGTH: 19
<212> TYPE: DNA
<213> ORGANISM: Artificial Sequence
<220> FEATURE:
<223> OTHER INFORMATION: Oligonucleotide

<400> SEQUENCE: 111
trrctaccag cactgccat                                                 19

<210> SEQ ID NO 112
<211> LENGTH: 17
<212> TYPE: DNA
<213> ORGANISM: Artificial Sequence
<220> FEATURE:
<223> OTHER INFORMATION: Oligonucleotide

<400> SEQUENCE: 112
gtcwatwgtc attgtgt                                                   17

<210> SEQ ID NO 113
<211> LENGTH: 19
<212> TYPE: DNA
<213> ORGANISM: Artificial Sequence
<220> FEATURE:
<223> OTHER INFORMATION: Oligonucleotide

<400> SEQUENCE: 113
gtcattgtgt caatgtcag                                                 19

<210> SEQ ID NO 114
<211> LENGTH: 17
<212> TYPE: DNA
<213> ORGANISM: Artificial Sequence
<220> FEATURE:
<223> OTHER INFORMATION: Oligonucleotide

<400> SEQUENCE: 114
gtctattgtc attgtgt                                                   17

<210> SEQ ID NO 115
<211> LENGTH: 28
<212> TYPE: DNA
<213> ORGANISM: Artificial Sequence
<220> FEATURE:
<223> OTHER INFORMATION: Oligonucleotide

<400> SEQUENCE: 115
ctgctatgag taacacttgt cccatctt                                       28

<210> SEQ ID NO 116
<211> LENGTH: 19
<212> TYPE: DNA
<213> ORGANISM: Artificial Sequence
<220> FEATURE:
<223> OTHER INFORMATION: Oligonucleotide
```

<400> SEQUENCE: 116
tagctaccag cactgccat                                              19

<210> SEQ ID NO 117
<211> LENGTH: 24
<212> TYPE: DNA
<213> ORGANISM: Artificial Sequence
<220> FEATURE:
<223> OTHER INFORMATION: Oligonucleotide

<400> SEQUENCE: 117
ctaccagcac tgccattgat gtgc                                        24

<210> SEQ ID NO 118
<211> LENGTH: 28
<212> TYPE: DNA
<213> ORGANISM: Artificial Sequence
<220> FEATURE:
<223> OTHER INFORMATION: Oligonucleotide

<400> SEQUENCE: 118
ctgcyatgag tarcacytgy cccatctt                                    28

<210> SEQ ID NO 119
<211> LENGTH: 19
<212> TYPE: DNA
<213> ORGANISM: Artificial Sequence
<220> FEATURE:
<223> OTHER INFORMATION: Oligonucleotide

<400> SEQUENCE: 119
gtcwatwgtc attgtgtca                                              19

<210> SEQ ID NO 120
<211> LENGTH: 17
<212> TYPE: DNA
<213> ORGANISM: Artificial Sequence
<220> FEATURE:
<223> OTHER INFORMATION: Oligonucleotide

<400> SEQUENCE: 120 ytgyccatc ttyttyt                                                 17

<210> SEQ ID NO 121
<211> LENGTH: 26
<212> TYPE: DNA
<213> ORGANISM: Artificial Sequence
<220> FEATURE:
<223> OTHER INFORMATION: Oligonucleotide

<400> SEQUENCE: 121
gtcwatwgtc attgtgtcaa tgtcag                                      26

<210> SEQ ID NO 122
<211> LENGTH: 21
<212> TYPE: DNA
<213> ORGANISM: Artificial Sequence
<220> FEATURE:
<223> OTHER INFORMATION: Oligonucleotide

<400> SEQUENCE: 122
trrctaccag cactgccatt g                                           21

```
<210> SEQ ID NO 123
<211> LENGTH: 22
<212> TYPE: DNA
<213> ORGANISM: Artificial Sequence
<220> FEATURE:
<223> OTHER INFORMATION: Oligonucleotide

<400> SEQUENCE: 123
gragcattct tgcttcaagc ca                                              22

<210> SEQ ID NO 124
<211> LENGTH: 22
<212> TYPE: DNA
<213> ORGANISM: Artificial Sequence
<220> FEATURE:
<223> OTHER INFORMATION: Oligonucleotide

<400> SEQUENCE: 124
gtcaagragc attcttgctt ca                                              22

<210> SEQ ID NO 125
<211> LENGTH: 20
<212> TYPE: DNA
<213> ORGANISM: Artificial Sequence
<220> FEATURE:
<223> OTHER INFORMATION: Oligonucleotide

<400> SEQUENCE: 125
gtcattgtgt caatgtcagt                                                 20

<210> SEQ ID NO 126
<211> LENGTH: 19
<212> TYPE: DNA
<213> ORGANISM: Artificial Sequence
<220> FEATURE:
<223> OTHER INFORMATION: Oligonucleotide

<400> SEQUENCE: 126
tcattgtgtc aatgtcagt                                                  19

<210> SEQ ID NO 127
<211> LENGTH: 19
<212> TYPE: DNA
<213> ORGANISM: Artificial Sequence
<220> FEATURE:
<223> OTHER INFORMATION: Oligonucleotide

<400> SEQUENCE: 127
gtctattgtc attgtgtca                                                  19

<210> SEQ ID NO 128
<211> LENGTH: 23
<212> TYPE: DNA
<213> ORGANISM: Artificial Sequence
<220> FEATURE:
<223> OTHER INFORMATION: Oligonucleotide

<400> SEQUENCE: 128
attgtcattg tgtcaatgtc agt                                             23

<210> SEQ ID NO 129
<211> LENGTH: 21
<212> TYPE: DNA
<213> ORGANISM: Artificial Sequence
<220> FEATURE:
<223> OTHER INFORMATION: Oligonucleotide
```

<400> SEQUENCE: 129
attgtcattg tgtcaatgtc a                                              21

<210> SEQ ID NO 130
<211> LENGTH: 20
<212> TYPE: DNA
<213> ORGANISM: Artificial Sequence
<220> FEATURE:
<223> OTHER INFORMATION: Oligonucleotide

<400> SEQUENCE: 130
attgtcattg tgtcaatgtc                                                20

<210> SEQ ID NO 131
<211> LENGTH: 19
<212> TYPE: DNA
<213> ORGANISM: Artificial Sequence
<220> FEATURE:
<223> OTHER INFORMATION: Oligonucleotide

<400> SEQUENCE: 131
attgtcattg tgtcaatgt                                                 19

<210> SEQ ID NO 132
<211> LENGTH: 17
<212> TYPE: DNA
<213> ORGANISM: Artificial Sequence
<220> FEATURE:
<223> OTHER INFORMATION: Oligonucleotide

<400> SEQUENCE: 132
ttgtcccatc ttcttct                                                   17

<210> SEQ ID NO 133
<211> LENGTH: 19
<212> TYPE: DNA
<213> ORGANISM: Artificial Sequence
<220> FEATURE:
<223> OTHER INFORMATION: Oligonucleotide

<400> SEQUENCE: 133
gtaacacttg tcccatctt                                                 19

<210> SEQ ID NO 134
<211> LENGTH: 26
<212> TYPE: DNA
<213> ORGANISM: Artificial Sequence
<220> FEATURE:
<223> OTHER INFORMATION: Oligonucleotide

<400> SEQUENCE: 134
gtctattgtc attgtgtcaa tgtcag                                         26

<210> SEQ ID NO 135
<211> LENGTH: 25
<212> TYPE: DNA
<213> ORGANISM: Artificial Sequence
<220> FEATURE:
<223> OTHER INFORMATION: Oligonucleotide

<400> SEQUENCE: 135
ctaccagcac tgccattgat gtgct                                          25

```
<210> SEQ ID NO 136
<211> LENGTH: 22
<212> TYPE: DNA
<213> ORGANISM: Artificial Sequence
<220> FEATURE:
<223> OTHER INFORMATION: Oligonucleotide

<400> SEQUENCE: 136
ccagcactgc cattgatgtg ct                                              22

<210> SEQ ID NO 137
<211> LENGTH: 22
<212> TYPE: DNA
<213> ORGANISM: Artificial Sequence
<220> FEATURE:
<223> OTHER INFORMATION: Oligonucleotide

<400> SEQUENCE: 137
ctaccagcac tgccattgat gt                                              22

<210> SEQ ID NO 138
<211> LENGTH: 21
<212> TYPE: DNA
<213> ORGANISM: Artificial Sequence
<220> FEATURE:
<223> OTHER INFORMATION: Oligonucleotide

<400> SEQUENCE: 138
tagctaccag cactgccatt g                                               21

<210> SEQ ID NO 139
<211> LENGTH: 20
<212> TYPE: DNA
<213> ORGANISM: Artificial Sequence
<220> FEATURE:
<223> OTHER INFORMATION: Oligonucleotide

<400> SEQUENCE: 139
agcattcttg cttcaagcca                                                 20

<210> SEQ ID NO 140
<211> LENGTH: 19
<212> TYPE: DNA
<213> ORGANISM: Artificial Sequence
<220> FEATURE:
<223> OTHER INFORMATION: Oligonucleotide

<400> SEQUENCE: 140
gcattcttgc ttcaagcca                                                  19

<210> SEQ ID NO 141
<211> LENGTH: 22
<212> TYPE: DNA
<213> ORGANISM: Artificial Sequence
<220> FEATURE:
<223> OTHER INFORMATION: Oligonucleotide

<400> SEQUENCE: 141
ggagcattct tgcttcaagc ca                                              22

<210> SEQ ID NO 142
<211> LENGTH: 22
<212> TYPE: DNA
<213> ORGANISM: Artificial Sequence
<220> FEATURE:
<223> OTHER INFORMATION: Oligonucleotide
```

<400> SEQUENCE: 142
gtcaagaagc attcttgctt ca    22

<210> SEQ ID NO 143
<211> LENGTH: 23
<212> TYPE: DNA
<213> ORGANISM: Artificial Sequence
<220> FEATURE:
<223> OTHER INFORMATION: Oligonucleotide

<400> SEQUENCE: 143
tagagcgagg ctatgaggcc atc    23

<210> SEQ ID NO 144
<211> LENGTH: 22
<212> TYPE: DNA
<213> ORGANISM: Artificial Sequence
<220> FEATURE:
<223> OTHER INFORMATION: Oligonucleotide

<400> SEQUENCE: 144
tagagcgagg ctatgaggcc at    22

<210> SEQ ID NO 145
<211> LENGTH: 21
<212> TYPE: DNA
<213> ORGANISM: Artificial Sequence
<220> FEATURE:
<223> OTHER INFORMATION: Oligonucleotide

<400> SEQUENCE: 145
tagagcgagg ctatgaggcc a    21

<210> SEQ ID NO 146
<211> LENGTH: 18
<212> TYPE: DNA
<213> ORGANISM: Artificial Sequence
<220> FEATURE:
<223> OTHER INFORMATION: Oligonucleotide

<400> SEQUENCE: 146
tagagcgagg ctatgagg    18

<210> SEQ ID NO 147
<211> LENGTH: 17
<212> TYPE: DNA
<213> ORGANISM: Artificial Sequence
<220> FEATURE:
<223> OTHER INFORMATION: Oligonucleotide

<400> SEQUENCE: 147
tagagcgagg ctatgag    17

<210> SEQ ID NO 148
<211> LENGTH: 13
<212> TYPE: DNA
<213> ORGANISM: Artificial Sequence
<220> FEATURE:
<223> OTHER INFORMATION: Oligonucleotide

<400> SEQUENCE: 148
ccagcactgc cat    13

```
<210> SEQ ID NO 149
<211> LENGTH: 16
<212> TYPE: DNA
<213> ORGANISM: Artificial Sequence
<220> FEATURE:
<223> OTHER INFORMATION: Oligonucleotide

<400> SEQUENCE: 149
ctaccagcac tgccat                                                        16

<210> SEQ ID NO 150
<211> LENGTH: 27
<212> TYPE: DNA
<213> ORGANISM: Artificial Sequence
<220> FEATURE:
<223> OTHER INFORMATION: Oligonucleotide

<400> SEQUENCE: 150
gtcwatwgtc attgtgtcaa tgtcagt                                            27

<210> SEQ ID NO 151
<211> LENGTH: 70
<212> TYPE: DNA
<213> ORGANISM: Artificial Sequence
<220> FEATURE:
<223> OTHER INFORMATION: Oligonucleotide

<400> SEQUENCE: 151
ctgcyatgag tarcacytgy cccatcttyt tytccacytg ggggtcwatw gtcattgtgt        60
caatgtcagt                                                               70

<210> SEQ ID NO 152
<211> LENGTH: 27
<212> TYPE: DNA
<213> ORGANISM: Artificial Sequence
<220> FEATURE:
<223> OTHER INFORMATION: Oligonucleotide

<400> SEQUENCE: 152
trrctaccag cactgccatt gatgtgc                                            27

<210> SEQ ID NO 153
<211> LENGTH: 55
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (23)..(55)
<223> OTHER INFORMATION: capture probe tail

<400> SEQUENCE: 153
gccuuaucuc cauuccauac catttaaaaa aaaaaaaaaa aaaaaaaaaa aaaaa             55

<210> SEQ ID NO 154
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail
```

```
<400> SEQUENCE: 154
ggccuuaucu ccauuccaua ccatttaaaa aaaaaaaaaa aaaaaaaaaa aaaaaa            56

<210> SEQ ID NO 155
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail

<400> SEQUENCE: 155
acauccccuc caguguucau uuctttaaaa aaaaaaaaaa aaaaaaaaaa aaaaaa            56

<210> SEQ ID NO 156
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail

<400> SEQUENCE: 156
agccacaucu ccuccagugu ucatttaaaa aaaaaaaaaa aaaaaaaaaa aaaaaa            56

<210> SEQ ID NO 157
<211> LENGTH: 58
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (29)..(58)
<223> OTHER INFORMATION: capture probe tail

<400> SEQUENCE: 157
augacucucu caccaucaag uaugacttaa aaaaaaaaaa aaaaaaaaaa aaaaaaaa          58

<210> SEQ ID NO 158
<211> LENGTH: 58
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (26)..(58)
<223> OTHER INFORMATION: capture probe tail

<400> SEQUENCE: 158
agcuugaacu cucccucaau ggcggtttaa aaaaaaaaaa aaaaaaaaaa aaaaaaaa          58

<210> SEQ ID NO 159
<211> LENGTH: 58
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (26)..(58)
<223> OTHER INFORMATION: capture probe tail
```

```
<400> SEQUENCE: 159
cugucuucca uuauggguguu guuggutuaa aaaaaaaaaa aaaaaaaaaa aaaaaaaa        58

<210> SEQ ID NO 160
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail

<400> SEQUENCE: 160
ccugggauca aguacaugua gugtttaaaa aaaaaaaaaa aaaaaaaaaa aaaaaa           56

<210> SEQ ID NO 161
<211> LENGTH: 54
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (22)..(54)
<223> OTHER INFORMATION: capture probe tail

<400> SEQUENCE: 161
ccugggauca aguacaugua gtttaaaaaa aaaaaaaaaa aaaaaaaaaa aaaa             54

<210> SEQ ID NO 162
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail

<400> SEQUENCE: 162
gaggaguucc aguauuuguu uggtttaaaa aaaaaaaaaa aaaaaaaaaa aaaaaa           56

<210> SEQ ID NO 163
<211> LENGTH: 51
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (22)..(51)
<223> OTHER INFORMATION: capture probe tail

<400> SEQUENCE: 163
gaggaguucc aguauuuguu uaaaaaaaaa aaaaaaaaaa aaaaaaaaaa a                51

<210> SEQ ID NO 164
<211> LENGTH: 61
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (28)..(61)
<223> OTHER INFORMATION: capture probe tail
```

<400> SEQUENCE: 164
cggccaauca guucaucuug guggcggctt taaaaaaaaa aaaaaaaaaa aaaaaaaaaa    60
a                                                                   61

<210> SEQ ID NO 165
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (24)..(56)
<223> OTHER INFORMATION: capture probe tail

<400> SEQUENCE: 165
cagcuagucu ccaguucagg ccctttaaaa aaaaaaaaa aaaaaaaaa aaaaaa          56

<210> SEQ ID NO 166
<211> LENGTH: 23
<212> TYPE: DNA
<213> ORGANISM: Artificial Sequence
<220> FEATURE:
<223> OTHER INFORMATION: Oligonucleotide

<400> SEQUENCE: 166
cagcuagucu ccaguucagg ccc                                           23

<210> SEQ ID NO 167
<211> LENGTH: 28
<212> TYPE: DNA
<213> ORGANISM: Artificial Sequence
<220> FEATURE:
<223> OTHER INFORMATION: Oligonucleotide

<400> SEQUENCE: 167
cggccaauca guucaucuug guggcggc                                      28

<210> SEQ ID NO 168
<211> LENGTH: 23
<212> TYPE: DNA
<213> ORGANISM: Artificial Sequence
<220> FEATURE:
<223> OTHER INFORMATION: Oligonucleotide

<400> SEQUENCE: 168
ggccuuaucu ccauuccaua cca                                           23

<210> SEQ ID NO 169
<211> LENGTH: 23
<212> TYPE: DNA
<213> ORGANISM: Artificial Sequence
<220> FEATURE:
<223> OTHER INFORMATION: Oligonucleotide

<400> SEQUENCE: 169
acaucuccuc caguguucau uuc                                           23

<210> SEQ ID NO 170
<211> LENGTH: 21
<212> TYPE: DNA
<213> ORGANISM: Artificial Sequence
<220> FEATURE:
<223> OTHER INFORMATION: Oligonucleotide

```
<400> SEQUENCE: 170
ccugggauca aguacaugua g                                              21

<210> SEQ ID NO 171
<211> LENGTH: 22
<212> TYPE: DNA
<213> ORGANISM: Artificial Sequence
<220> FEATURE:
<223> OTHER INFORMATION: Oligonucleotide

<400> SEQUENCE: 171
gccuuaucuc cauuccauac ca                                             22

<210> SEQ ID NO 172
<211> LENGTH: 23
<212> TYPE: DNA
<213> ORGANISM: Artificial Sequence
<220> FEATURE:
<223> OTHER INFORMATION: Oligonucleotide

<400> SEQUENCE: 172
agccacaucu ccuccagugu uca                                            23

<210> SEQ ID NO 173
<211> LENGTH: 28
<212> TYPE: DNA
<213> ORGANISM: Artificial Sequence
<220> FEATURE:
<223> OTHER INFORMATION: Oligonucleotide

<400> SEQUENCE: 173
augacucucu caccaucaag uaugactt                                       28

<210> SEQ ID NO 174
<211> LENGTH: 25
<212> TYPE: DNA
<213> ORGANISM: Artificial Sequence
<220> FEATURE:
<223> OTHER INFORMATION: Oligonucleotide

<400> SEQUENCE: 174
agcuugaacu cucccucaau ggcgg                                          25

<210> SEQ ID NO 175
<211> LENGTH: 25
<212> TYPE: DNA
<213> ORGANISM: Artificial Sequence
<220> FEATURE:
<223> OTHER INFORMATION: Oligonucleotide

<400> SEQUENCE: 175
cugucuucca uuaugguguu guugg                                          25

<210> SEQ ID NO 176
<211> LENGTH: 23
<212> TYPE: DNA
<213> ORGANISM: Artificial Sequence
<220> FEATURE:
<223> OTHER INFORMATION: Oligonucleotide

<400> SEQUENCE: 176
ccugggauca aguacaugua gug                                            23
```

```
<210> SEQ ID NO 177
<211> LENGTH: 23
<212> TYPE: DNA
<213> ORGANISM: Artificial Sequence
<220> FEATURE:
<223> OTHER INFORMATION: Oligonucleotide

<400> SEQUENCE: 177
gaggaguucc aguauuuguu ugg                                                 23

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
gaggaguucc aguauuuguu u                                                   21

<210> SEQ ID NO 179
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: promoter
<222> LOCATION: (1)..(27)

<400> SEQUENCE: 179
aatttaatac gactcactat agggaga                                             27

<210> SEQ ID NO 180
<211> LENGTH: 14
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(14)
<223> OTHER INFORMATION: immobilized probe

<400> SEQUENCE: 180
tttttttttt tttt                                                           14

<210> SEQ ID NO 181
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(33)
<223> OTHER INFORMATION: capture probe tail

<400> SEQUENCE: 181
tttaaaaaaa aaaaaaaaaa aaaaaaaaaa aaa                                      33

<210> SEQ ID NO 182
<211> LENGTH: 30
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: misc_feature
<222> LOCATION: (1)..(30)
<223> OTHER INFORMATION: capture probe tail

<400> SEQUENCE: 182
aaaaaaaaaa aaaaaaaaaa aaaaaaaaaa                                    30

<210> SEQ ID NO 183
<211> LENGTH: 121
<212> TYPE: DNA
<213> ORGANISM: Artificial Sequence
<220> FEATURE:
<223> OTHER INFORMATION: amplicon

<400> SEQUENCE: 183
aggacagcag ctggcatcat gaagaatccc gttgtggatg aatagtggt aactgacatt    60 gacacaatga caatagaccc ccaggtggag aagaagatgg gacaagtgtt actcatagca   120
g                                                                  121

<210> SEQ ID NO 184
<211> LENGTH: 78
<212> TYPE: DNA
<213> ORGANISM: Artificial Sequence
<220> FEATURE:
<223> OTHER INFORMATION: amplicon

<400> SEQUENCE: 184
aggacagcag ctggcatcat gaagaatccc gttgtggatg aatagtggt aactgacatt    60 gacacaatga caatagac                                                 78

<210> SEQ ID NO 185
<211> LENGTH: 135
<212> TYPE: DNA
<213> ORGANISM: Artificial Sequence
<220> FEATURE:
<223> OTHER INFORMATION: amplicon

<400> SEQUENCE: 185
ccctaacaaa cctggagatg agtacatgta tggaggtggg tgtgcagaga ctgatgaagg    60
ccatgcacac tggcttgaag caagaatgct tcttgacaac atctacctcc aggatggcct   120
catagcctcg ctcta                                                   135

<210> SEQ ID NO 186
<211> LENGTH: 103
<212> TYPE: DNA
<213> ORGANISM: Artificial Sequence
<220> FEATURE:
<223> OTHER INFORMATION: amplicon

<400> SEQUENCE: 186
tctcttggag tgcttgtgat tctactcatg gtgcaggagg ggttgaagaa gagaatgacc    60
acaaagatca tcatgagcac atcaatggca gtgctggtag tca                    103

<210> SEQ ID NO 187
<211> LENGTH: 103
<212> TYPE: DNA
<213> ORGANISM: Artificial Sequence
<220> FEATURE:
<223> OTHER INFORMATION: amplicon
```

```
<400> SEQUENCE: 187
tcycttggag tgcttgtgat tytrctcatg gtgcaggarg ggytraagaa gagaatgacc    60
acaaagatca tcatragcac atcaatggca gtgctggtag yya                    103

<210> SEQ ID NO 188
<211> LENGTH: 135
<212> TYPE: DNA
<213> ORGANISM: Artificial Sequence
<220> FEATURE:
<223> OTHER INFORMATION: amplicon

<400> SEQUENCE: 188
yccyaayaaa cctggagatg agtaymtgta tggaggtggg tgygcagaga ctgaygaagr    60
ycaygcacac tggcttgaag caagaatgct ycttgacaay atytacctcc argatggcct   120
catagcytcg ctcta                                                    135

<210> SEQ ID NO 189
<211> LENGTH: 78
<212> TYPE: DNA
<213> ORGANISM: Artificial Sequence
<220> FEATURE:
<223> OTHER INFORMATION: amplicon

<400> SEQUENCE: 189
agracrgcag ctggcatcat gaagaayccy gttgtggakg gaatagtggt ractgacatt    60
gacacaatga cwatwgac                                                 78

<210> SEQ ID NO 190
<211> LENGTH: 121
<212> TYPE: DNA
<213> ORGANISM: Artificial Sequence
<220> FEATURE:
<223> OTHER INFORMATION: amplicon

<400> SEQUENCE: 190
agracrgcag ctggcatcat gaagaayccy gttgtggakg gaatagtggt ractgacatt    60
gacacaatga cwatwgaccc ccargtggar aaraagatgg grcargtgyt actcatrgca   120
g                                                                   121

<210> SEQ ID NO 191
<211> LENGTH: 511
<212> TYPE: DNA
<213> ORGANISM: Artificial Sequence
<220> FEATURE:
<223> OTHER INFORMATION: in vitro transcript

<400> SEQUENCE: 191
gggcgaauug gguaccgggc cccccucga ggucgacggu aucgauaagc uugcugcuaa     60
ugauggguug cuauucacaa uuaacacccc ugacucugau aguagcuauc auucugcuug   120
uggcgcacua caugugacuug aucccaggcc uacaagcggc agcagcgcgu gcugcccaga   180
aaaggacagc agcuggcauc augaagaauc ccguugugga uggaauagug guaacugaca   240
uugacacaau gacaauagac ccccaggugg agaagaagau gggacaagug uuacucauag   300
caguagccau cuccagugcu gugcugcugc ggaccgccug gggauggggg gaggcuggag   360
cucugaucac agcagcgacc uccaccuugu gggaaggcuc uccaaacaaa uacuggaacu   420
ccucuacagc caccucacug ugcaacaucu ucagaggaag cuaucuggca ggagcuuccc   480
uuaucuauac agugacgaga aacgcugaau u                                  511
```

<210> SEQ ID NO 192
<211> LENGTH: 507
<212> TYPE: DNA
<213> ORGANISM: Artificial Sequence
<220> FEATURE:
<223> OTHER INFORMATION: in vitro transcript

<400> SEQUENCE: 192

```
gggcgaauug gguaccgggc cccccucga ggucgacggu aucgauaagc uugauaucga      60
auccugcag cccggggau cccacuaucg uuucgagcaa agacggcug cugguaugga       120
auggagauaa ggcccaggaa agaaccagag agcaacuuag ugaggucaau ggugacagcg    180
ggucaaccg aucauaugga ccacuucucu cuuggagugc uugugauucu acucauggug     240
caggaggggu ugaagaagag aaugaccaca aagaucauca ugagcacauc aauggcagug    300
cugguaguca ugaucuuggg aggauuuuca augagugacc uggccaagcu ugugauccug    360
auggggcua cuuucgcaga aaugaacacu ggaggagaug uagcucacuu ggcauuggua    420
gcggcauuua aagucagacc agccuugcug gucuccuuca uuucagagc caauuggaca    480
ccccgugaga gcaugcugcu agcggcc                                       507
```

<210> SEQ ID NO 193
<211> LENGTH: 566
<212> TYPE: DNA
<213> ORGANISM: Artificial Sequence
<220> FEATURE:
<223> OTHER INFORMATION: in vitro transcript

<400> SEQUENCE: 193

```
gggcgaauug gguaccgggc cccccucga ggucgacggu aucgauaagc uugucauaga      60
cucuaggaga ugccuaaaac cagucauacu ugauggugag agagucaucu uggcugggcc   120
caugccuguc acgcaugcua gugcugcuca gaggagagga cguauaggca ggaacccuaa   180
caaaccugga gaugaguaca uguauggagg uggguguggca gagacugaug aaggccaugc  240
acacuggcuu gaagcaagaa ugcuucuuga caacaucuac cuccaggaug ccucauagc    300
cucgcucuau cggccugagg ccgauaaggu agccgccauu gagggagagu uuaagcugag   360
gacagagcaa aggaagaccu ucguggaacu caugaagaga ggagaccuuc cgucuggcu    420
agccuaucag guugcaucug ccggaauaac uuacacagac agaagauggu gcuuugaugg   480
cacaaccaac aacaccauaa uggaagacag cguaccagca gaggugugga caaaguaugg   540
agagaagaga gugcucaaac cgaauu                                        566
```

<210> SEQ ID NO 194
<211> LENGTH: 71
<212> TYPE: DNA
<213> ORGANISM: Artificial Sequence
<220> FEATURE:
<223> OTHER INFORMATION: amplicon

<400> SEQUENCE: 194

```
agracrgcag ctggcatcat gaagaayccy gttgtggakg gaatagtggt ractgacatt      60
gacacaatga c                                                          71
```

<210> SEQ ID NO 195
<211> LENGTH: 88
<212> TYPE: DNA
<213> ORGANISM: Artificial Sequence
<220> FEATURE:
<223> OTHER INFORMATION: amplicon

```
<400> SEQUENCE: 195
ymtgtatgga ggtgggtgyg cagagactga ygaagrycay gcacactggc ttgaagcaag      60
aatgctyctt gacaayatyt acctccar                                        88

<210> SEQ ID NO 196
<211> LENGTH: 52
<212> TYPE: DNA
<213> ORGANISM: Artificial Sequence
<220> FEATURE:
<223> OTHER INFORMATION: amplicon

<400> SEQUENCE: 196
rctcatggtg caggargggy traagaagag aatgaccaca aagatcatca tr             52

<210> SEQ ID NO 197
<211> LENGTH: 25
<212> TYPE: DNA
<213> ORGANISM: Artificial Sequence
<220> FEATURE:
<223> OTHER INFORMATION: amplicon

<400> SEQUENCE: 197
yccygttgtg gakggaatag tggtr                                           25

<210> SEQ ID NO 198
<211> LENGTH: 63
<212> TYPE: DNA
<213> ORGANISM: Artificial Sequence
<220> FEATURE:
<223> OTHER INFORMATION: amplicon

<400> SEQUENCE: 198
yccygttgtg gakggaatag tggtractga cattgacaca atgacwatwg acccccargt     60
gga                                                                   63
```